United States Patent
Hazan et al.

(10) Patent No.: US 10,588,911 B2
(45) Date of Patent: *Mar. 17, 2020

(54) COMPOSITIONS COMPRISING TRITERPENOIDS

(71) Applicant: REGENERA PHARMA LTD., Ness Ziona (IL)

(72) Inventors: Zadik Hazan, Zikron Yaakov (IL); Konstantin Adamsky, Gedera (IL); Andre C. B. Lucassen, Rehovot (IL); Nurit Novak, Ness Ziona (IL)

(73) Assignee: REGENERA PHARMA LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/359,068

(22) Filed: Mar. 20, 2019

(65) Prior Publication Data

US 2019/0209582 A1 Jul. 11, 2019

Related U.S. Application Data

(63) Continuation of application No. 15/761,759, filed as application No. PCT/IL2016/051057 on Sep. 22, 2016, now Pat. No. 10,285,996.

(60) Provisional application No. 62/222,976, filed on Sep. 24, 2015.

(51) Int. Cl.
| | | |
|---|---|---|
| *A61K 31/56* | (2006.01) | |
| *A61K 45/06* | (2006.01) | |
| *A61K 31/569* | (2006.01) | |
| *A61K 31/575* | (2006.01) | |
| *A61K 31/745* | (2006.01) | |
| *A61K 36/22* | (2006.01) | |
| *A61K 31/122* | (2006.01) | |

(52) U.S. Cl.
CPC ............ *A61K 31/56* (2013.01); *A61K 31/122* (2013.01); *A61K 31/569* (2013.01); *A61K 31/575* (2013.01); *A61K 31/745* (2013.01); *A61K 36/22* (2013.01); *A61K 45/06* (2013.01)

(58) Field of Classification Search
None
See application file for complete search history.

(56) References Cited

U.S. PATENT DOCUMENTS 7,048,943 B2   5/2006  Barenholz et al.
2014/0329791 A1  11/2014  Jinwal et al.

FOREIGN PATENT DOCUMENTS

| CA | 2804789 A1 | 1/2012 |
|---|---|---|
| CN | 103360456 A | 10/2013 |
| WO | 03/092712 A1 | 11/2003 |
| WO | 2005/094837 A1 | 10/2005 |
| WO | 2005/112967 A2 | 12/2005 |
| WO | 2010/032123 A1 | 3/2010 |
| WO | 2010/100650 A2 | 9/2010 |
| WO | 2010/100651 A2 | 9/2010 |
| WO | 2012/032523 A2 | 3/2012 |
| WO | 2015/135474 A1 | 9/2015 |

OTHER PUBLICATIONS

Ahmed et al., (2011) "Chemical Characterization of a Commercial Commiphora wightii Resin Sample and Chemical Profiling to Assess for Authenticity", Planta Med 77(9): 945-950.
Barton and Seoane, (1956) 801. "Triterpenoids. Part XXII. The Constitution and Stereochemistry of Masticadienonic Acid", J. Chem. Soc. 0: 4150-4157.
Chen et al., (2001) "Therapeutic Benefit of Intravenous Administration of Bone Marrow Stromal Cells After Cerebral Ischemia in Rats", Stroke 32(4): 1005-1011.
Domingo et al., (2009) "Enantioselective Total Synthesis of the Potent Anti-inflammatory (+)-Myrrhanol A", J. Org. Chem. 74(16): 6151-6156.
Domingo et al., (2013) "First Synthesis of (+)-myrrhanol C, an anti-prostate cancer lead", Org. Biomol. Chem. 11(4): 559-562.
Giner-Larza et al., (2002) "Anti-inflammatory Triterpenes from Pistacia terebinthus Galls", Planta Med 68(4): 311-315.
Justicia et al., (2004) "Titanocene-Catalyzed Cascade Cyclization of Epoxypolyprenes: Straightforward Synthesis of Terpenoids by Free-Radical Chemistry", Chemistry 10(7): 1778-1788.
Lemaire et al., (1994) "CCK-A and CCK-B selective receptor agonists and antagonists modulate olfactory recognition in male rats", Psychopharmacology (Bell) 115(4): 435-440.
Marner et al., (1991) "Triterpenoids from Gum Mastic, the Resin of Pistacia lentiscus", Phytochemistry 30(11): 3709-3712.
Paraschos et al., (2007) "In Vitro and In Vivo Activities of Chios Mastic Gum Extracts and Constituents Against Helicobacter pylori", Antimicrob Agents Chemother 51(2): 551-559.
Parmar et al., (2013) "Neuropharmacological effects of triterpenoids", Phytopharmacology 4(2): 354-372.
Porsolt et al., (1995) "Animal Models of Dementia", Drug Dev. Res. 35(4): 214-229.
Schmid-Elsaesser et al., (1998) "A Critical Reevaluation of the Intraluminal Thread Model of Focal Cerebral Ischemia: Evidence of Inadvertent Premature Reperfusion and Subarachnoid Hemorrhage in Rats by Laser-Doppler Flowmetry", Stroke 29(10): 2162-2170.
Watanabe et al., (2006) "Cilostazol Protects Against Brain White Matter Damage and Cognitive Impairment in a Rat Model of Chronic Cerebral Hypoperfusion", Stroke 37(6): 1539-1545.

*Primary Examiner* — Brian J Davis

(74) *Attorney, Agent, or Firm* — Rothwell, Figg, Ernst & Manbeck, P.C.

(57) ABSTRACT

The invention relates to compositions and formulations comprising at least one triterpenoic acid and at least one neutral triterpenoid and uses thereof for treating for use in treating a condition selected from Alzheimer's disease (AD), Parkinson's Diseases (PD) and vascular dementia (VD).

21 Claims, 11 Drawing Sheets

COMPOSITIONS COMPRISING TRITERPENOIDS

CROSS REFERENCE TO RELATED APPLICATION

This application is a continuation of U.S. patent application Ser. No. 15/761,759, filed Mar. 20, 2018, which is a 35 U.S.C. 371 National Phase Entry Application from PCT/IL2016/051057, filed Sep. 22, 2016, which claims the benefit of U.S. Provisional Patent Application No. 62/222,976 filed on Sep. 24, 2015, the disclosures of which are incorporated herein in their entirety by reference.

FIELD OF THE INVENTION

The invention relates to compositions comprising triterpenoids, and uses thereof for treating Alzheimer's disease (AD), Parkinson's Diseases (PD) and/or vascular dementia (VD).

BACKGROUND OF THE INVENTION

Various drug entities derived from plants and plant products have been disclosed over the years, for various therapeutic applications.

For example, Paraschos et al disclose preparation of a total mastic extract without polymer (TMEWP) by polar solvent extraction of crude mastic, removal of the insoluble polymer poly-β-myrcene therefrom, and separation of acidic and neutral fractions from TMEWP (Paraschos et al (2007) Antimicrob. Agents Chemother. 51(2):551-559).

International Patent Application Publication No. WO 2005/112967 is directed to the anticancer activity of mastic gum.

International Patent Application Publication No. WO 2010/100650 of some of the inventors of the present invention, is directed to therapeutic uses of mastic gum fractions.

International Patent Application Publication No. WO 2010/100651 of some of the inventors of the present invention, is directed to compositions of polymeric myrcene.

International Patent Application Publication NO. WO 2012/032523 of some of the inventors of the present invention, is directed to acidic compositions of mastic gum.

International Patent Application Publication No. WO 2005/094837 is directed to Use of masticadienonic acid as inhibitor of DNA polymerase-beta, used for treating cancers, tumors and neurodegenerative diseases.

Marner et al (1991) disclose identification of various triterpenoids from gum mastic of *P. lentiscus* (Marner et al (1991) Phytochemistry, 30, 3709-3712).

Giner-Larza et al (2002) disclose anti-inflammatory triterpenes from *pistacia terebinthus* galls (Planta Med (2002), 68, 311-315).

Neurodegenerative disorders, such as Alzheimer's disease (AD), Parkinson's Diseases (PD) and vascular dementia (VD) are adult onset, chronic, progressive and irreversible severely disabling diseases.

Vascular dementia (VD) is a subtype of dementia with a prevalence that is second only to that of Alzheimer's disease in westernized societies. VD causes many neuropsychiatric and physical problems, and represents a significant economic burden. Brain imaging has revealed obvious changes in the cerebral cortex and white matter, and these lesions are thought to be the core pathology for cognitive declines in patients with vascular dementia.

Alzheimer's disease (AD) is characterized by progressive mental and cognitive deterioration with consequent formation of amyloid plaques, neurofibrillary tangles, gliosis and neuronal loss. The disease occurs in both genetic and sporadic forms whose clinical course and pathological features are quite similar.

Parkinson's disease (PD) is a chronic and progressive neurodegenerative disease caused by a selective degeneration of dopaminergic neurons in the substantia nigra pars compacta of the brain; 80% of the neurons die of an unknown cause before the symptoms appear. Symptoms include intermittent tremor in the limbs, poor balance and difficulty in initiating movement. PD has a characteristic clinical syndrome of bradykinesia, tremor, rigidity, and postural instability. Degenerative parkinsonian disorders can be inherited or sporadic, but are all characterized by neuronal loss in selective populations of vulnerable neurons. The common denominator of all degenerative parkinsonian disorders is loss of dopaminergic neurons of the substantia nigra that project to the putamen (i.e., dopaminergic nigrostriatal pathway). Five main separate Parkinson-plus syndromes have been identified Multiple system atrophy (MSA), Progressive supranuclear palsy (PSP), Parkinsonism-dementia-amyotrophic lateral sclerosis complex, Corticobasal ganglionic degeneration (CBD) and Dementia with Lewy bodies (DLB). Additional Parkinson-plus syndromes include Pick's disease and olivopontocerebellar Atrophy (OPCA).

There remains an unmet need for safe, versatile and effective compounds and compositions, which may be obtained from plants by reproducible, highly efficient and cost-effective methods, for use in the treatment of Alzheimer's disease (AD), Parkinson's Diseases (PD) and/or vascular dementia (VD).

SUMMARY OF THE INVENTION

The following embodiments and aspects thereof are described and illustrated in conjunction with systems, tools and methods which are meant to be exemplary and illustrative, not limiting in scope.

In some embodiments, there are provided combinations of triterpenoid compounds, compositions comprising the same and uses thereof for the treatment of various health related conditions, such as, such as Alzheimer's disease (AD), Parkinson's Diseases (PD) and/or vascular dementia (VD).

In some embodiments, there are provided combinations of triterpenoid compounds, compositions comprising the same and uses thereof for the wound healing and rejuvenation of a large number of cells and tissues. In some embodiments, there is provided a composition comprising a combination of at least one triterpenoic acid and at least one neutral triterpenoid; and a pharmaceutically acceptable carrier.

In some embodiments, there is provided a composition comprising a combination of a triterpenoic acid and a neutral triterpenoid; and a pharmaceutically acceptable carrier.

In some embodiments, there is provided a composition comprising or consisting of at least one triterpenoic acid, at least one neutral triterpenoid and a pharmaceutically acceptable carrier.

In some embodiments, the triterpenoic acid may be selected from at least one of masticadienonic acid (MDA), isomasticadienonic acid (IMDA), masticadienolic acid (MLA), isomasticadienolic acid (IMLA), 3-O-acetyl masticadienolic acid, 3-O-acetyl epimasticadienolic acid, 3-O-acetyl isomasticadienolic acid, 3-O-acetyl epi-isomasticadienolic acid, oleanonic acid (OA) and moronic acid (MA), or any combination thereof. Each possibility is a separate embodiment. In some embodiments, the triterpenoic acid comprises or consists of at least one of masticadienonic acid (MDA), isomasticadienonic acid (IMDA), masticadienolic acid (MLA), isomasticadienolic acid (IMLA), 3-O-acetyl masticadienolic acid, 3-O-acetyl epimasticadienolic acid, 3-O-acetyl isomasticadienolic acid, 3-O-acetyl epi-isomasticadienolic acid, oleanonic acid (OA) and moronic acid (MA), or any combination thereof.

In some embodiments, the composition comprises or consists of at least two triterpenoic acids. In some embodiments, the composition comprises or consists of at least three triterpenoic acids. In some embodiments, the composition comprises or consists of at least four triterpenoic acids. In some embodiments, the composition comprises or consists of at least five triterpenoic acids. In some embodiments, the composition comprises or consists of at least six triterpenoic acids. In some embodiments, the composition comprises or consists of at least seven triterpenoic acids. In some embodiments, the composition comprises or consists of at least eight triterpenoic acids. In some embodiments, the composition comprises or consists of at least nine triterpenoic acids. In some embodiments, the composition comprises or consists of at least ten triterpenoic acids. In some embodiments, the composition comprises or consists of not more than two triterpenoic acids. In some embodiments, the composition comprises or consists of not more than three triterpenoic acids. In some embodiments, the composition comprises or consists of not more than four triterpenoic acids. In some embodiments, the composition comprises or consists of not more than five triterpenoic acids. In some embodiments, the composition comprises or consists of not more than six triterpenoic acids. In some embodiments, the composition comprises or consists of not more than seven triterpenoic acids. In some embodiments, the composition comprises or consists of not more than eight triterpenoic acids. In some embodiments, the composition comprises or consists of not more than nine triterpenoic acids. In some embodiments, the composition comprises or consists not more than ten triterpenoic acids.

In some embodiments, the at least one triterpenoic acid(s) comprises or consists of at least MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA. Each possibility is a separate embodiment. In some embodiments, the triterpenoic acid(s) comprises or consists of at least MDA, IMDA, MLA, IMLA, 3-O-acetyl masticadienolic acid, 3-O-acetyl isomasticadienolic acid, OA and MA. In some embodiments, the triterpenoic acid(s) comprises or consists of at least MDA, IMDA, MLA and IMLA. In some embodiments, the triterpenoic acid comprises or consists of at least MDA and IMDA. In some embodiments, the triterpenoic acid comprises or consists of at least MDA. In some embodiments, the triterpenoic acid comprises at least IMDA.

In some embodiments, the triterpenoic acid is selected from MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA. Each possibility is a separate embodiment. In some embodiments, the triterpenoic acid is selected from MDA, IMDA, MLA, IMLA, 3-O-acetyl masticadienolic acid, 3-O-acetyl isomasticadienolic acid, OA and MA. In some embodiments, the triterpenoic acid is selected from MDA, IMDA, MLA and IMLA. In some embodiments, the triterpenoic acid is selected from MDA and IMDA.

In some embodiments, the triterpenoic acid consists of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA. Each possibility is a separate embodiment. In some embodiments, the triterpenoic acid consists of MDA, IMDA, MLA, IMLA, 3-O-acetyl masticadienolic acid, 3-O-acetyl isomasticadienolic acid, OA and MA. In some embodiments, the triterpenoic acid consists of MDA, IMDA, MLA and IMLA. In some embodiments, the triterpenoic acid consists of MDA and IMDA.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, 20-hydroxydammar-24-en-3-one (NF-P) is not present in the pharmaceutical composition.

In some embodiments, the neutral triterpenoid comprises or consists of at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment.

In some embodiments, the neutral triterpenoid comprises or consists of at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment.

In some embodiments, the neutral triterpenoid does not comprise 20-hydroxydammar-24-en-3-one (NF-P).

In some embodiments, the neutral triterpenoid does not consist of 20-hydroxydammar-24-en-3-one (NF-P).

In some embodiments the neutral triterpenoid comprises or consists of at least two neutral triterpenoids. In some embodiments the neutral triterpenoid comprises or consists of at least three neutral triterpenoids. In some embodiments the neutral triterpenoid comprises or consists of at least four neutral triterpenoids. In some embodiments the neutral triterpenoid comprises or consists of at least five neutral triterpenoids. In some embodiments the neutral triterpenoid comprises or consists of at least six neutral triterpenoids. In some embodiments the neutral triterpenoid comprises or consists of at least seven neutral triterpenoids. In some embodiments the neutral triterpenoid comprises or consists of not more than two neutral triterpenoids. In some embodiments the neutral triterpenoid comprises or consists of not more than three neutral triterpenoids. In some embodiments the neutral triterpenoid comprises or consists of not more than four neutral triterpenoids. In some embodiments the neutral triterpenoid comprises or consists of not more than five neutral triterpenoids. In some embodiments the neutral triterpenoid comprises or consists of not more than six neutral triterpenoids. In some embodiments the neutral triterpenoid comprises or consists of not more than seven neutral triterpenoids.

In some embodiments, the neutral triterpenoid comprises at least NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the neutral triterpenoid comprises at least NF-1, NF-2, NF-3, NF-4, NF-A, NF-B and NF-P. In some embodiments, the neutral triterpenoid comprises at least NF-1, NF-2, NF-3, NF-4, NF-A and NF-B. In some embodiments, the neutral triterpenoid comprises at least NF-1, NF-2, NF-3 and NF-4. In some embodiments, the neutral triterpenoid comprises at least NF-1, NF-2 and NF-3. In some embodiments, the neutral triterpenoid comprises at least NF-1, NF-2 and NF-4. In some embodiments, the neutral triterpenoid comprises at least NF-1, NF-3 and NF-4. In some embodiments, the neutral triterpenoid comprises at least NF-2, NF-3 and NF-4. In some embodiments, the neutral triterpenoid comprises at least NF-1 and NF-2. In some embodiments, the neutral triterpenoid comprises at least NF-1. In some embodiments, the neutral triterpenoid comprises at least NF-2. In some embodiments, the neutral triterpenoid comprises at least NF-3. In some embodiments, the neutral triterpenoid comprises at least NF-4. In some embodiments, the neutral triterpenoid comprises at least NF-A. In some embodiments, the neutral triterpenoid comprises at least NF-B.

In some embodiments, the neutral triterpenoid is selected from NF-1, NF-2, NF-3, NF-4, NF-A, NF-B, NF-P, 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment.

In some embodiments, the neutral triterpenoid comprises at least NF-1, NF-2, NF-3, NF-4, NF-A, NF-B and NF-P. In some embodiments, the neutral triterpenoid comprises at least NF-1, NF-2, NF-3, NF-4, NF-A and NF-B. In some embodiments, the neutral triterpenoid comprises at least NF-1, NF-2, NF-3 and NF-4. In some embodiments, the neutral triterpenoid comprises at least NF-1, NF-2 and NF-3. In some embodiments, the neutral triterpenoid comprises at least NF-1, NF-2 and NF-4. In some embodiments, the neutral triterpenoid comprises at least NF-1, NF-3 and NF-4. In some embodiments, the neutral triterpenoid comprises at least NF-2, NF-3 and NF-4. In some embodiments, the neutral triterpenoid comprises at least NF-1 and NF-2. In some embodiments, the neutral triterpenoid comprises at least NF-1. In some embodiments, the neutral triterpenoid comprises at least NF-2. In some embodiments, the neutral triterpenoid comprises at least NF-3. In some embodiments, the neutral triterpenoid comprises at least NF-4. In some embodiments, the neutral triterpenoid comprises at least NF-A. In some embodiments, the neutral triterpenoid comprises at least NF-B.

In some embodiments, the neutral triterpenoid is selected from NF-1, NF-2, NF-3, NF-4, NF-A, NF-B and NF-P. In some embodiments, the neutral triterpenoid is selected from NF-1, NF-2, NF-3, NF-4, NF-A and NF-B. In some embodiments, the neutral triterpenoid is selected from NF-1, NF-2, NF-3 and NF-4. In some embodiments, the neutral triterpenoid is selected from NF-1, NF-2 and NF-3. In some embodiments, the neutral triterpenoid is selected from NF-1, NF-2 and NF-4. In some embodiments, the neutral triterpenoid is selected from NF-1 and NF-2.

In some embodiments, the neutral triterpenoid consists of NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the neutral triterpenoid consists of NF-1, NF-2, NF-3, NF-4, NF-A, NF-B and NF-P. In some embodiments, the neutral triterpenoid consists of NF-1, NF-2, NF-3 and NF-4. In some embodiments, the neutral triterpenoid consists of NF-1 and NF-2.

In some embodiments, there is provided a pharmaceutical composition comprising pharmaceutically active ingredients comprising or consisting essentially of MA, OA, MDA, IMDA 3-O-acetyl masticadienolic acid, 3-O-acetyl isomasticadienolic acid, MLA, IMLA, NF-1, NF-2, NF-3 and NF-4; and a pharmaceutically acceptable carrier.

In some embodiments, there is provided a pharmaceutical composition comprising pharmaceutically active ingredients comprising or consisting essentially of MDA, IMDA, MLA, IMLA, NF-1, NF-2, NF-3, NF-4, NF-A and NF-B; and a pharmaceutically acceptable carrier.

In some embodiments, there is provided a pharmaceutical composition comprising pharmaceutically active ingredients comprising or consisting essentially of MDA, IMDA, MLA, IMLA, NF-1, NF-2, NF-3, NF-4, NF-P, NF-A and NF-B; and a pharmaceutically acceptable carrier.

In some embodiments, there is provided a pharmaceutical composition comprising pharmaceutically active ingredients comprising or consisting essentially of MDA, IMDA, NF-1, NF-2, NF-3 and NF-4; and a pharmaceutically acceptable carrier.

In some embodiments, there is provided a pharmaceutical composition comprising pharmaceutically active ingredients comprising or consisting essentially of MDA, IMDA, NF-1 and NF-2; and a pharmaceutically acceptable carrier.

In some embodiments, there is provided a pharmaceutical composition comprising pharmaceutically active ingredients comprising or consisting essentially of MDA, IMDA, NF-1, NF-2, NF-3 and NF-4; and a pharmaceutically acceptable carrier.

In some embodiments, there is provided a pharmaceutical composition comprising pharmaceutically active ingredients comprising or consisting essentially of MA, OA, MDA, IMDA, 3-O-acetyl masticadienolic acid, 3-O-acetyl isomasticadienolic acid, MLA, IMLA, NF-1, NF-2, NF-3, NF-4, NF-P, NF-A and NF-B as the sole pharmaceutically active ingredients; and a pharmaceutically acceptable carrier.

In some embodiments, there is provided a pharmaceutical composition comprising pharmaceutically active ingredients comprising or consisting essentially of MA, OA, MDA, IMDA, 3-O-acetyl masticadienolic acid, 3-O-acetyl isomasticadienolic acid, MLA, IMLA, NF-1, NF-2, NF-3, NF-4, NF-A and NF-B as the sole pharmaceutically active ingredients; and a pharmaceutically acceptable carrier.

In some embodiments, there is provided a pharmaceutical composition comprising pharmaceutically active ingredients comprising or consisting essentially of MDA, IMDA, NF-1, NF-2, NF-3, NF-4, NF-P, NF-A and NF-B as the sole pharmaceutically active ingredients; and a pharmaceutically acceptable carrier.

In some embodiments, there is provided a pharmaceutical composition comprising pharmaceutically active ingredients comprising or consisting essentially of MDA, IMDA, NF-1, NF-2, NF-3, NF-4, NF-A and NF-B as the sole pharmaceutically active ingredients; and a pharmaceutically acceptable carrier.

In some embodiments, there is provided a pharmaceutical composition comprising pharmaceutically active ingredients consisting essentially of MA, OA, MDA, IMDA, 3-O-acetyl masticadienolic acid, 3-O-acetyl isomasticadienolic acid, NF-1, NF-2, NF-3, NF-4, NF-A and NF-B; and a pharmaceutically acceptable carrier.

In some embodiments, there is provided a pharmaceutical composition comprising pharmaceutically active ingredients consisting essentially of MA, OA, MDA, IMDA, 3-O-acetyl masticadienolic acid, 3-O-acetyl isomasticadienolic acid, NF-1, NF-2, NF-3 and NF-4; and a pharmaceutically acceptable carrier.

In some embodiments, there is provided a pharmaceutical composition comprising pharmaceutically active ingredients consisting essentially of OA, MDA, IMDA, 3-O-acetyl masticadienolic acid, 3-O-acetyl isomasticadienolic acid, NF-1, NF-2, NF-3, NF-4, NF-A and NF-B; and a pharmaceutically acceptable carrier.

In some embodiments, there is provided a pharmaceutical composition comprising pharmaceutically active ingredients consisting essentially of OA, MDA, IMDA, 3-O-acetyl masticadienolic acid, 3-O-acetyl isomasticadienolic acid, NF-1, NF-2, NF-3 and NF-4; and a pharmaceutically acceptable carrier.

In some embodiments, there is provided a pharmaceutical composition comprising pharmaceutically active ingredients consisting essentially of MDA, IMDA, NF-1, NF-2; and a pharmaceutically acceptable carrier.

In some embodiments, there is provided a pharmaceutical composition comprising pharmaceutically active ingredients consisting essentially of MDA, IMDA, NF-1, NF-2, NF-3, NF-4, NF-A and NF-B as the sole pharmaceutically active ingredients; and a pharmaceutically acceptable carrier.

In some embodiments, there is provided a pharmaceutical composition comprising pharmaceutically active ingredients consisting essentially of MDA, IMDA, NF-1, NF-2, NF-3 and NF-4 as the sole pharmaceutically active ingredients; and a pharmaceutically acceptable carrier.

In some embodiments, there is provided a pharmaceutical composition comprising pharmaceutically active ingredients consisting essentially of MDA, IMDA, NF-1 and NF-2 as the sole pharmaceutically active ingredients; and a pharmaceutically acceptable carrier.

In some embodiments, there is provided a composition comprising a combination of at least one triterpenoic acid and at least one neutral triterpenoid, and a pharmaceutically acceptable carrier, wherein the triterpenoic acid is selected from MDA, IMDA or both, wherein the neutral triterpenoid is selected from NF-1, NF-2, or both.

In some embodiments the composition further comprises at least one additional triterpenoic acid. In some embodiments, the additional triterpenoic acid is selected from the group consisting of MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA, MA and combinations thereof.

In some embodiments, the composition further comprises at least one additional neutral triterpenoid. In some embodiments, the additional neutral triterpenoid is selected from the group consisting of NF-3, NF-4, NF-A, NF-B, NF-P and combinations thereof.

In some embodiments, the composition further comprises at least one additional neutral triterpenoid. In some embodiments, the additional neutral triterpenoid is selected from the group consisting of NF-3, NF-4, NF-A, NF-B and combinations thereof.

In some embodiments, the composition further comprises NF-P.

In some embodiments, at least one of the additional neutral triterpenoids is selected from NF-3 and NF-4.

In some embodiments, the composition comprises at least two additional neutral triterpenoids.

In some embodiments, the triterpenoic acid(s) may be obtained from a plant source. In some embodiments, any one of the triterpenoic acids may be obtained from a plant source. In some embodiments, at least one triterpenoic acid may be obtained from a plant source. In some embodiments, the neutral triterpenoid(s) may be obtained from a plant source. In some embodiments, any one of the neutral triterpenoids may be obtained from a plant source. In some embodiments, at least one neutral triterpenoid may be obtained from a plant source. In some embodiments, the plant source may include mastic gum.

In some embodiments, the triterpenoic acid(s) may be obtained via a chemical synthesis. In some embodiments, any one of the triterpenoic acids may be obtained via a chemical synthesis. In some embodiments, at least one triterpenoic acid may be obtained via a chemical synthesis.

In some embodiments, the neutral triterpenoid(s) may be obtained via a chemical synthesis. In some embodiments, any one of the neutral triterpenoids may be obtained via a chemical synthesis. In some embodiments, at least one neutral triterpenoid may be obtained via a chemical synthesis.

In some embodiments, the compositions and/or combinations of compounds, as disclosed herein, unexpectedly exhibit a variety of beneficial biological activities, which are exploited for therapeutic applications in a surprisingly efficient manner. More specifically, the compositions and combinations disclosed herein are shown to be active and useful in treating conditions such as Alzheimer's disease (AD), Parkinson's Diseases (PD) and vascular dementia (VD). In some embodiments, the treating of Alzheimer's disease (AD), Parkinson's Diseases (PD) and vascular dementia (VD) may be associated with reversal of the condition. In some embodiments, the treating Alzheimer's disease (AD), Parkinson's Diseases (PD) and vascular dementia (VD) may be associated with reducing or eliminating side effects caused by the condition.

In some embodiments, the compositions and/or combinations of compounds, as disclosed herein, unexpectedly exhibit a variety of beneficial biological activities, which are exploited for therapeutic applications in a surprisingly efficient manner. More specifically, the compositions and combinations disclosed herein are shown to be active and useful in treating conditions such as Multi System Athrophy (MSA) and Progressive Supranuclear Palsy. In some embodiments, the treating of Multi System Athrophy (MSA) and Progressive Supranuclear Palsy may be associated with reversal of the condition. In some embodiments, the treating of Multi System Athrophy (MSA) and Progressive Supranuclear Palsy may be associated with reducing or eliminating side effects caused by the condition.

In some embodiments, the compositions and/or combinations of compounds, as disclosed herein, unexpectedly exhibit a variety of beneficial biological activities, which are exploited for therapeutic applications in a surprisingly efficient manner. More specifically, the compositions and combinations disclosed herein are shown to be active and useful in treating conditions such as tauopathic diseases and conditions. In some embodiments, the treating of tauopathic diseases and conditions and vascular dementia (VD) may be associated with reversal of the condition. In some embodiments, the treating tauopathic diseases and conditions may be associated with reducing or eliminating side effects caused by the condition.

In some embodiments, there is provided a method of treating Alzheimer's disease (AD), Parkinson's Diseases (PD) and/or vascular dementia (VD), comprising administering to a subject a composition as disclosed herein. In some embodiments, there is provided a method of treating Alzheimer's disease (AD), Parkinson's Diseases (PD) and/or vascular dementia (VD) in a subject in need thereof, comprising administering to a subject a therapeutically effective amount of a composition as disclosed herein. In some embodiments, the method is for treating Alzheimer's disease (AD). In some embodiments, the method is for treating Parkinson's Diseases (PD). In some embodiments, the method is for treating vascular dementia (VD).

In some embodiments, there is provided a method of treating Multi System Atrophy (MSA) and Progressive Supranuclear Palsy (PSP), comprising administering to a subject a composition as disclosed herein. In some embodiments, there is provided a method of treating Multi System Atrophy (MSA) and Progressive Supranuclear Palsy (PSP), in a subject in need thereof, comprising administering to a subject a therapeutically effective amount of a composition as disclosed herein. In some embodiments, the method is for treating Multi System Atrophy (MSA). In some embodiments, the method is for treating Progressive Supranuclear Palsy (PSP).

In some embodiments, there is provided a method of treating tauopathic diseases and conditions, comprising administering to a subject a composition as disclosed herein. In some embodiments, there is provided a method of treating tauopathic diseases and conditions, in a subject in need thereof, comprising administering to a subject a therapeutically effective amount of a composition as disclosed herein.

In some embodiments, there is provided a method of treating primary age-related tauopathy (PART), comprising administering to a subject a composition as disclosed herein. In some embodiments, there is provided a method of treating primary age-related tauopathy (PART), in a subject in need thereof, comprising administering to a subject a therapeutically effective amount of a composition as disclosed herein.

In some embodiments, the composition is used for inducing or promoting life span extension in animals. In some embodiments, the animals are selected from the group of humans, non-human mammals, birds and fish.

In some embodiments, there is provided a kit comprising a pharmaceutical composition as disclosed herein.

In some embodiments, there is provided a kit comprising: (a) a pharmaceutical composition comprising at least one triterpenoic acid and a pharmaceutically acceptable carrier; (b) a pharmaceutical composition comprising at least one neutral triterpenoid and a pharmaceutically acceptable carrier.

In some embodiments, there is provided a use of at least one triterpenoic acid and at least one neutral triterpenoid in the preparation of a composition for treating Alzheimer's disease (AD), Parkinson's Diseases (PD) and/or vascular dementia (VD).

In some embodiments, there is provided a use of at least one triterpenoic acid and at least one neutral triterpenoid in the preparation of a composition for treating Multi System Atrophy (MSA) and Progressive Supranuclear Palsy (PSP).

In some embodiments, there is provided a use of at least one triterpenoic acid and at least one neutral triterpenoid in the preparation of a composition for treating tauopathic diseases and conditions.

In some embodiments, there is provided a use of at least one triterpenoic acid and at least one neutral triterpenoid in the preparation of a composition for treating tauopathic diseases and conditions.

In some embodiments, the composition is a pharmaceutical composition.

In some embodiments, the composition may be in a form suitable for administration by a route selected from the group consisting of parenteral, transdermal, oral and topical. In some embodiments, the composition may be in a form suitable for administration by injection. In some embodiments, the composition is a parenteral formulation for administration by a route selected from the group consisting of subcutaneous, intravenous, intramuscular, intradermal, intraperitoneal, intraarterial, intracerebral, intracerebroventricular, intraosseus and intrathecal.

In some embodiments, the subject to be treated with the compositions disclosed herein may be selected from the group of humans and non-human mammals.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 3A-shows cytolysis kinetic curves normalized on the 72 h data point (just before glutamate treatment. FIG. 3B shows areas under curves (AUC) of the cytolysis kinetics calculated from the 72 h time point to the end of the kinetics. *: $p<0.05$, **: $p<0.01$ compared to the vehicle-treated group, One-Way ANOVA followed by Dunnett's post hoc test.

FIG. 4A—shows cytolysis kinetic curves normalized on the 72 h data point (just before glutamate treatment. FIG. 4B shows areas under curves (AUC) of the cytolysis kinetics calculated from the 72 h time point to the end of the kinetics. *: $p<0.05$, **: $p<0.01$ compared to the vehicle-treated group, One-Way ANOVA followed by Dunnett's post hoc test.

DETAILED DESCRIPTION OF THE INVENTION

Figure 1:
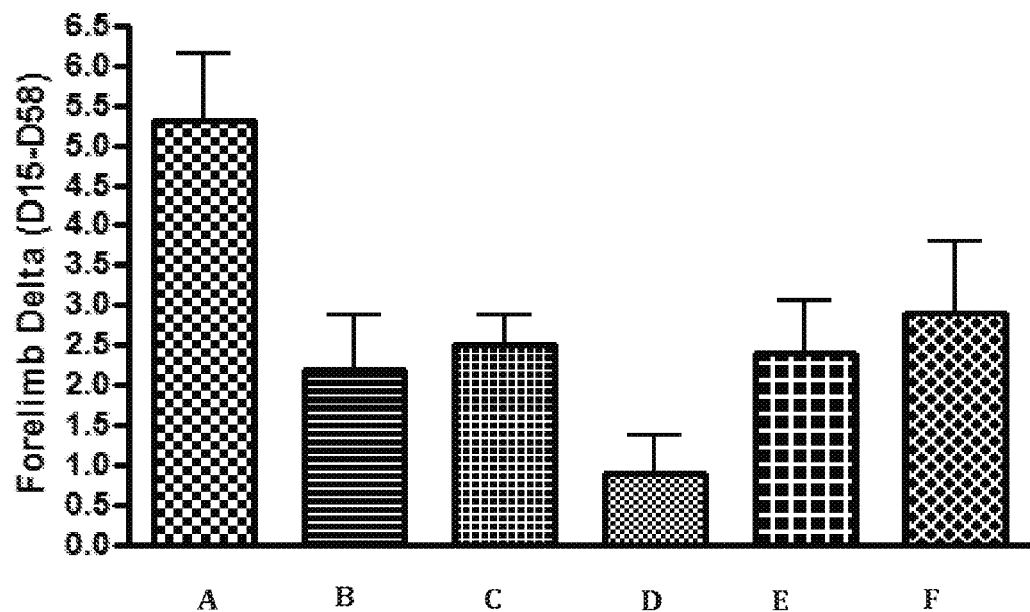
FIG. 1 displays bar graphs showing the forelimb placement delta score in Groups A-F (Respective Entries nr. 4 (group-A); 27 (group B); 31 (Group C); 2 (Group E); 26 (Group F) of Table 1A) of the forelimb-placing test in a tMCAO stroke model in rats. Group D is placebo control.

As disclosed herein, it has been surprisingly found that combinations of triterpenoic acids and neutral triterpenoid compounds show high activity in treating a condition selected from Alzheimer's disease (AD), Parkinson's Diseases (PD) and vascular dementia (VD).

It has further been surprisingly found that combinations of triterpenoic acids and neutral triterpenoid compounds show high activity in treating a condition selected from Multi System Atrophy (MSA), Progressive Supranuclear Palsy (PSP) and tauopathic conditions and diseases.

Specific combinations of triterpenoic acids and neutral terpenoid compounds surprisingly show enhanced therapeutic efficacy.

Definitions

As used herein the term "plurality" refers to more than one, preferably more than two. As used herein the term "synergistic" means more than additive.

As used herein, the term "acid-base extraction" refers to a procedure in which an organic solvent solution containing organic acidic (typically, organic carboxylic acids) and organic non-acidic components is treated/extracted with one or more basic aqueous solution(s). As a result, the organic acidic components are deprotonated and thus converted into their corresponding deprotonated ionic salt forms (typically, organic anionic carboxylates) and as a result will dissolve in the said basic aqueous solution. The non-acidic organic components will not deprotonate, thus will stay behind in the original organic solution phase. The deprotonated acids may also form an intermediate oily and/or emulsion layer, especially when multigram amounts are being extracted. The basic aqueous solution containing the deprotonated salt forms of the acidic components, together with the oily and/or emulsion layer (if present), is acidified, resulting in the reformation of the protonated acid forms of the organic acidic components. These protonated acid forms (acidic fraction) can be removed from the acidified aqueous solution in several ways depending on the properties of the acidic compounds. One option for removing the acidic fraction from the acidified solution is by reextraction into a suitable organic solvent. Examples 1A and 1B hereinbelow describe a non-limiting example of an acid-base extraction as described above. Depending on the solubility and physical form of the acidic compounds (e.g. if the acidic fraction typically comprises a separated/precipitated solid) in the acidified aqueous solution, the acidic fraction may be isolated via filtration of the acidified aqueous solution.

As stated above, the original organic solution phase remaining after extraction with basic aqueous solution(s) contains the non-acidic organic components. In the case of mastic gum these non-acidic components consist of neutral triterpenoids and the mixture is referred to as a neutral fraction. Examples 1A and 1B below describe a particular (but non-limiting) method for the isolation of a certain acidic and a certain neutral fraction from mastic gum.

From the isolated acidic fraction and neutral fraction, the individual triterpenoic acids and neutral triterpenoids can be isolated using methods known in the art such as column chromatography and HPLC. Several references presented in the introduction of the current application contain examples of separation methods for triterpenoic acids and neutral triterpenoids from mastic gum.

Instead of using a basic aqueous solution for the acid-base extraction, basic forms of ion-exchange resins can be used as well. In these cases, upon contact with the ion-exchange resin the acidic organic components (acidic fraction-typically, organic carboxylic acids) are captured in their deprotonated anionic form (typically, organic anionic carboxylates) by the resin. The resin is subsequently removed from the initial solution, leaving non-acidic components behind. The acidic components (acidic fraction) are subsequently released from the resin by treatment of the resin with a suitable acidic solution. The use of ion-exchange resins for acid-base extractions is especially suitable for process scale up and can be used for the development of (semi)continuous extraction processes.

Examples of the above acid-base extractions and other variations can be found in many textbooks and other publications, and are considered common knowledge to those skilled in the art. An example of a useful textbook is "Vogel's Textbook of Practical Organic Chemistry", $5^{th}$ Edition, 1989, (p. 162-163).

As used herein, the term "degree of purity" refers to the content of a specified chemical compound in a preparation, expressed as a percentage on a weight per weight basis of the specified chemical compound relative to other chemical compounds in the preparation.

As used herein, "terpene compounds" refers to isoprene-containing hydrocarbons, having isoprene units ($CH_2C(CH_3)CHCH_2$) in a head-to-tail orientation. Terpene hydrocarbons in general, have the molecular formula $(C_5H_8)_n$, and include hemiterpenes, (C5), monoterpenes (C10), sesquiterpenes (C15), diterpenes (C20), triterpenes (C30), and tetraterpenes (C40) which respectively have 1, 2, 3, 4, 6 and 8 isoprene units. Terpenes may be further classified as acyclic or cyclic.

As used herein, "terpenoids" and "terpenoid compounds" interchangeably refer to terpene-related compounds, which contain at least one oxygen atom in addition to isoprene units, and thus include alcohols, aldehydes, ketones, ethers, such as but not limited to, carboxylic acids derivatives thereof, such as esters. Terpenoids are subdivided according to the number of carbon atoms in a manner similar to terpene and thus include hemiterpenoids, (C5), monoterpenoids (C10), sesquiterpenoids (C15), diterpenoids (C20), triterpenoids (C30), and tetraterpenoids (C40) which respectively have 1, 2, 3, 4, 6 and 8 isoprene units. The skeleton of terpenoids may differ from strict additivity of isoprene units by the loss or shift of a fragment, commonly a methyl group. Examples of monoterpenoids include camphor, eugenol, menthol and borneol. Examples of diterpenoids include phytol, retinol and taxol. Examples of triterpenoids include betulinic acid and lanosterol. Terpenoids may be acyclic or may contain one or more ring-structures. Triterpenoids may be acyclic or may contain one or more ring-structures. The rings may contain only carbon atoms, or alternatively may contain one or more oxygen atoms besides carbon atoms. Common ring-sizes range from three-membered rings to ten-membered rings. Larger ring sizes of up to at least twenty-membered rings are possible. More than one ring and more than one ring-size maybe present in a single triterpenoid. In case a triterpenoid contains more than one ring, the rings may be present and separated by one or more acyclic bonds; alternatively, the rings may be directly connected via connections of the annealed type, the bridged type, the spiro-type or combinations of any of these types. Multiply annealed, fused, bridged, or spiro-type ringsystems are possible. Combinations of singly and multiply annealed, bridged, fused, spiro-type rings are possible. Combinations of isolated rings and connected rings in the same triterpenoid are possible.

As used herein, "terpenoic acids" refer to terpenoid compounds containing at least one carboxylic acid functional group (COOH). The terpenoic acids may additionally contain one or more other oxygen-containing functional groups, for example, but not limited to hydroxyl, keto, aldehyde, ether (cyclic and non-cyclic), ester (cyclic and non-cyclic). They also may contain one or more C=C double bond, each double bond may be of the cis, trans, E-type, Z-type, as well as mono-substituted, di-substituted, tri-substituted or tetrasubstituted (meaning no vinylic H-substituent), independently from other C=C bonds. The carboxylic acid group may be present in the protonated form (COOH) or in deprotonated anionic form (COO⁻).

As used herein, "triterpenoic acids" refer to triterpenoid compounds containing at least one carboxylic acid group. The triterpenoic acids may additionally contain one or more other oxygen-containing functional groups for example, but not limited to, hydroxyl, keto, aldehyde, ether (cyclic and non-cyclic) and ester (cyclic and non-cyclic). They also may contain one or more C=C double bond, each double bond may be of the cis, trans, E- or Z-type, as well as monosubstituted, disubstituted, trisubstituted or tetrasubstituted (meaning no vinylic H-substituent), independently from other C=C bonds. The carboxylic acid group may be present in the protonated form (COOH) or in deprotonated anionic form (COO).

As used herein, "neutral terpenoids" refer to terpenoid compounds lacking a carboxylic acid group. The neutral triterpenoids may contain one or more other oxygen-containing functional groups for example, but not limited to, hydroxyl, keto, aldehyde, ether (cyclic and non-cyclic) and ester (cyclic and non-cyclic). They also may contain one or more C=C double bond, each double bond may be of the cis, trans, E- or Z-type, as well as monosubstituted, disubstituted, trisubstituted or tetrasubstituted (meaning no vinylic H-substituent), independently from other C=C bonds.

As used herein, "neutral triterpenoids" refer to triterpenoid compounds lacking a carboxylic acid group. The neutral triterpenoids may contain one or more other oxygen-containing functional groups for example, but not limited to, hydroxyl, keto, aldehyde, ether (cyclic and non-cyclic) and ester (cyclic and non-cyclic). They also may contain one or more C=C double bond, each double bond may be of the cis, trans, E- or Z-type, as well as monosubstituted, disubstituted, trisubstituted or tetrasubstituted (meaning no vinylic H-substituent), independently from other C=C bonds.

As used herein, "an oligomeric form of a terpenoic acid" refers to an oligomeric terpenoid acid in which the monomeric units are either of the same terpenoic acid or of different terpenoic acids, and are joined in any possible arrangements, and are connected one to another through any possible bond or functional group, such as a C—C bond, but not limited to, an ester group or an ether group.

As used herein, "an oligomeric form of a triterpenoic acid" refers to an oligomeric triterpenoid acid in which the monomeric units are either of the same triterpenoic acid or of different triterpenoic acids, and are joined in any possible arrangements, and are connected one to another through any possible bond or functional group, such as, but not limited to, a C—C bond, an ester group or an ether group.

As used herein, the terms "mastic", "mastic resin", "gum mastic" and "mastic gum", are used interchangeably to refer to a tree resin (also known as an oleoresin) obtained as an exudate from any tree classified in the family Anacardiaceae. Trees in the genus *Pistacia*, most notably *Pistacia lentiscus* L., and in particular the cultivar *P. lentiscus* L. cv. *Chia* (cultivated on the Greek island of Chios), are known for their high yield of gum mastic. Other varieties include *P. lentiscus* L. var. *emarginata* Engl., and *P. lentiscus* L. var. *latifolia* Coss. Additional species of *Pistacia* include for example, *P. atlantica*, *P. palestina*, *P. saportae*, *P. terebinthus*, *P. vera* and *P. integerrima*.

As used herein, the terms "masticadienoic acid", "masticadienonic acid", "masticadienoic" and "masticadienonic" may interchangeably be used.

In order to provide clarity with respect to the molecular structure of compounds frequently mentioned and referred to in this application, a list of structures with names and acronyms used in this application is presented below.

Masticadienonic acid refers to 24-Z-masticadienonic acid, the acronym MDA used in the current application refers to this compound. The chemical structure of 24-Z-masticadienonic acid is as follows:

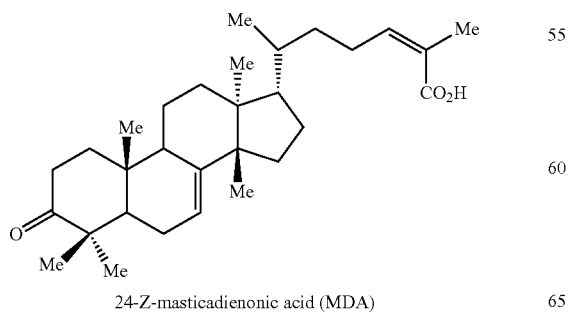

24-Z-masticadienonic acid (MDA)

As used herein, the terms "isomasticadienoic acid", "isomasticadienonic acid", "isomasticadienoic" and "isomasticadienonic" may interchangeably be used.

Isomasticadienonic acid refers 24-Z-isomasticadienonic acid, the acronym IMDA used in the current application refers to this compound. The chemical structure of 24-Z-isomasticadienonic acid is as follows:

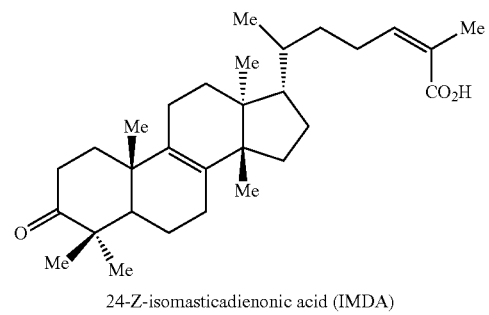

24-Z-isomasticadienonic acid (IMDA)

Oleanonic acid (OLN) has the following molecular structure:

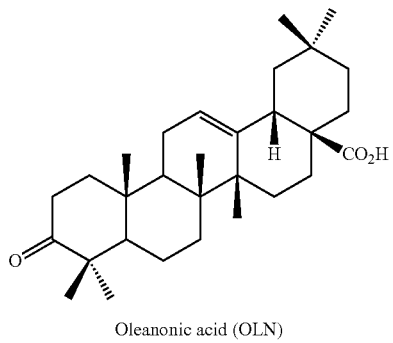

Oleanonic acid (OLN)

Moronic acid (MO) has the following molecular structure:

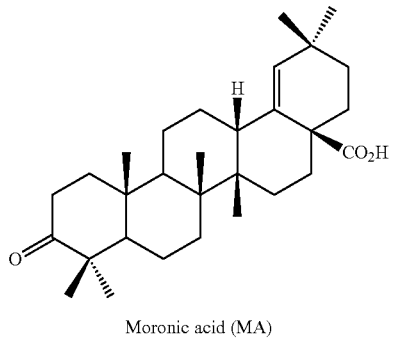

Moronic acid (MA)

24-Z-masticadienolic acid (MLA) has the following structure, the 3-hydroxyl group has the beta-configuration:

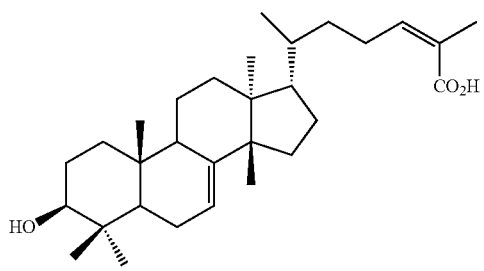

MLA

24-Z-epimasticadienolic acid (epi-MLA) has the following structure, the 3-hydroxyl group has the alpha-configuration:

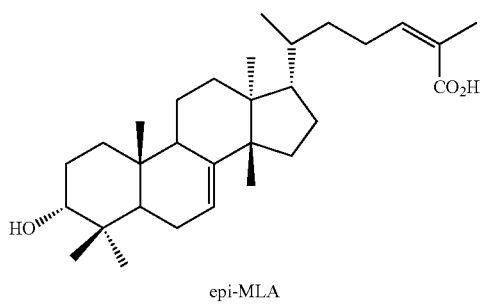

epi-MLA

24-Z-isomasticadienolic acid (IMLA) has the following structure, the 3-hydroxyl group has the beta-configuration:

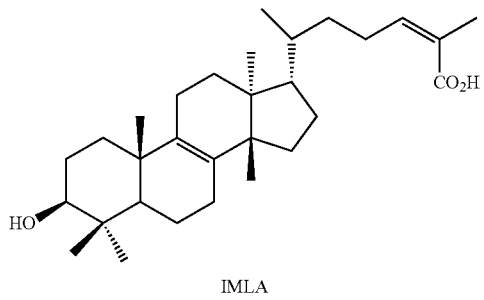

IMLA

24-Z-epi-isomasticadienolic acid (epi-IMLA) has the following structure, the 3-hydroxyl group has the beta-configuration:

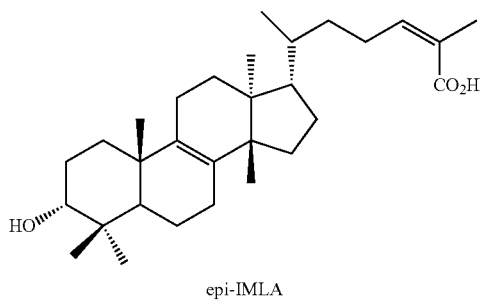

epi-IMLA

24-Z-3-O-acetyl-masticadienolic acid (3-OAc-MLA) has the following molecular structure:

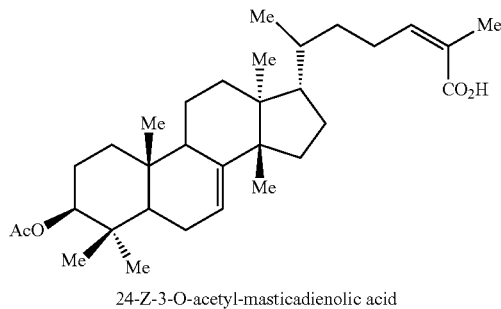

24-Z-3-O-acetyl-masticadienolic acid

24-Z-3-O-acetyl-epimasticadienolic acid (3-OAc-epi-MLA) has the following molecular structure:

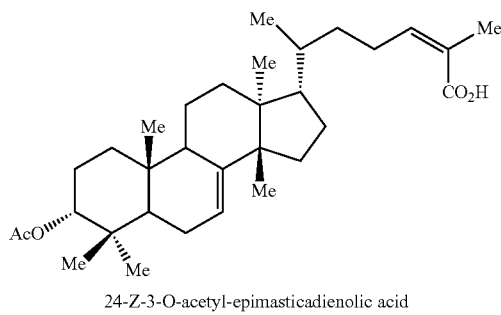

24-Z-3-O-acetyl-epimasticadienolic acid

24-Z-3-O-acetyl-isomasticadienolic acid (3-OAc-IMLA) has the following molecular structure:

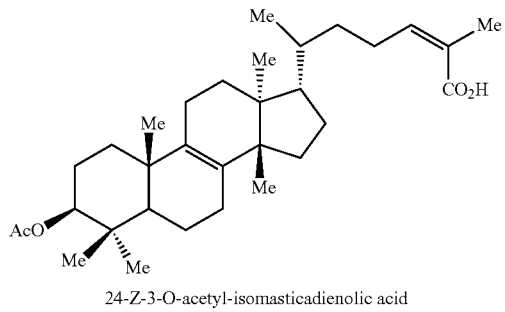

24-Z-3-O-acetyl-isomasticadienolic acid

24-Z-3-O-acetyl-epiisomasticadienolic acid (3-OAc-epi-IMLA) has the following molecular structure:

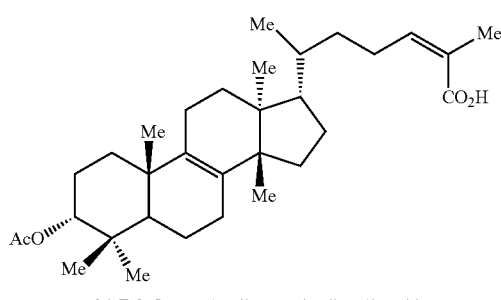

24-Z-3-O-acetyl-epiisomasticadienolic acid

It is to be understood that in the context of this disclosure, in case the "24-Z" is omitted from any the abovementioned compound names, it is this particular 24-Z-isomer that is referred to.

The term "NF-1" is directed to the neutral triterpenoid compound (8R)-3-beta, 8-dihydroxypolypoda-13E,17E,21-triene (also referred to as Myrrhanol C), having the structure as set forth in scheme I:

Scheme I

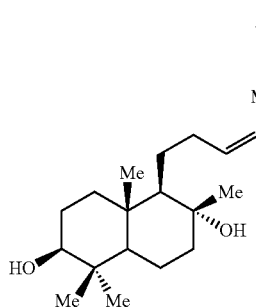

NF-1

The term "NF-2" is directed to the neutral triterpenoid compound ((8R)-3-Oxo-8-hydroxypolypoda-13E,17E,21-triene, having the structure as set forth in scheme II:

Scheme II

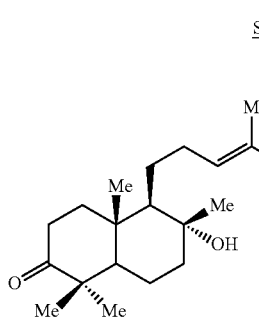

NF-2

The term "NF-3" is directed to the neutral triterpenoid compound Oleanonic aldehyde, having the structure as set forth in scheme III:

Scheme III

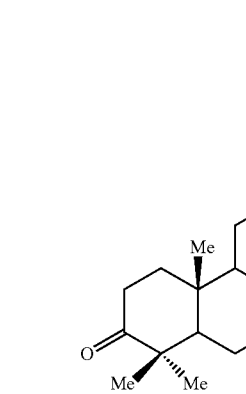

NF-3

The term "NF-4" is directed to the neutral triterpenoid compound Tirucallol (C-20 Epimer of Euphol), having the structure as set forth in scheme IV:

Scheme IV

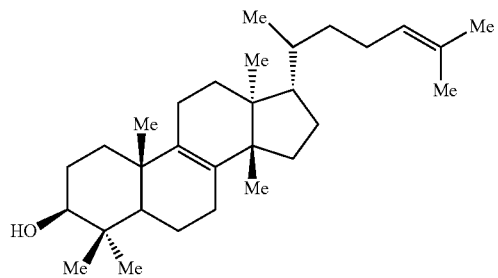

NF-4

The term "NF-A" is directed to the neutral triterpenoid compound 28-hydroxylup-20(29)-en-3-one (also referred to as Betulon), having the structure as set forth in scheme V:

Scheme V

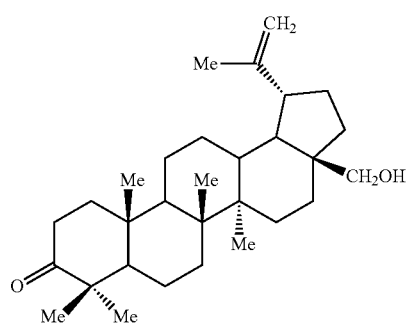

NF-A

The term "NF-B" is directed to the neutral triterpenoid compound 28-hydroxy-beta-amyrone (also referred to as Oleanonic alcohol), having the structure as set forth in scheme VI:

Scheme VI

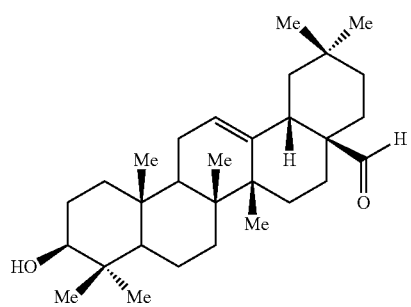

NF-B

The term "NF-P" is directed to the neutral triterpenoid compound 20-hydroxydammar-24-en-3-one (also referred to as Dipterocarpol), having the structure as set forth in scheme VII.

Scheme VII

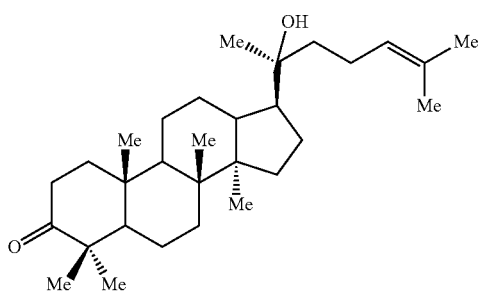

NF-P, 20-hydroxydammar-24-en-3-one (NF-P; Dipterocarpol)

Additional neutral triterpenoids isolated from mastic gum neutral fraction are the following:

Name: 3-beta-20-dihydroxylupane

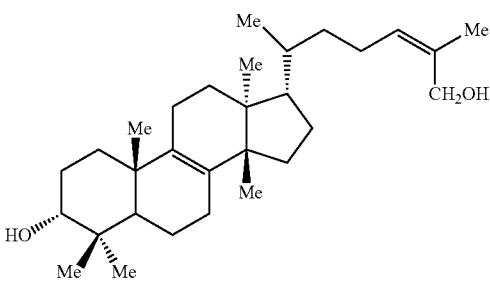

Name: 3-beta-hydroxy-13-alpha-malabarica-14(26), 17E, 21-triene

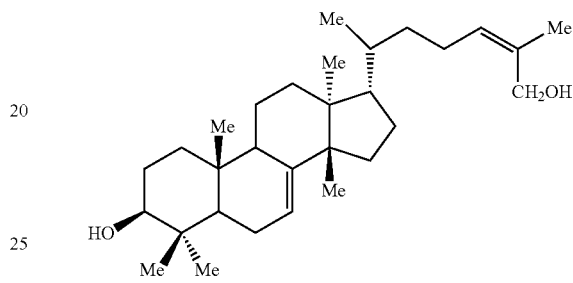

Name: 3-oxo-malabarica-14(26), 17E, 21-triene

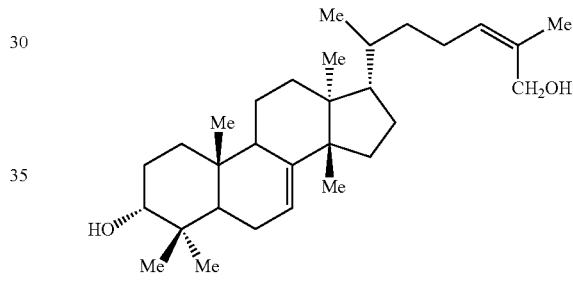

Name: Isomasticadienediol

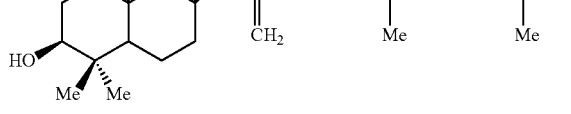

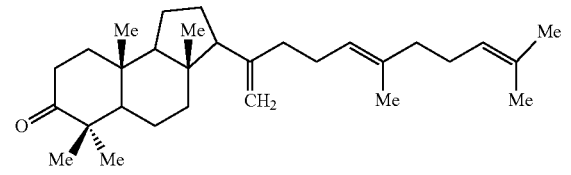

Name: Epi-isomasticadienediol

Name: Masticadienediol

Name: Epi-masticadienediol

Name: Isomasticadienonic aldehyde

Name: Masticadienonic aldehyde

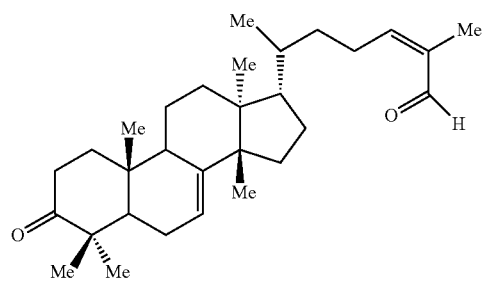

-continued

Name: Beta-amyrin

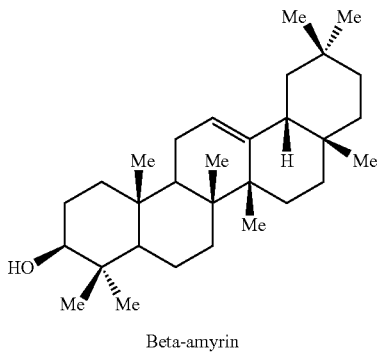

Beta-amyrin

Name: Beta-amyrone

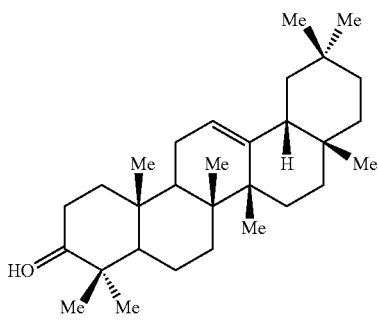

Beta-amyrone

Name: Germanicol

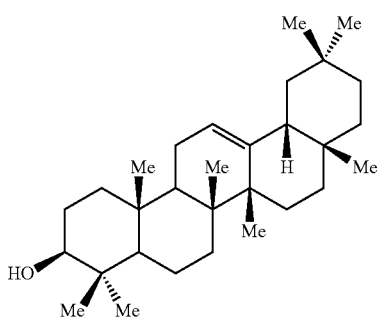

Germanicol

Name: 28-nor-beta-amyrin

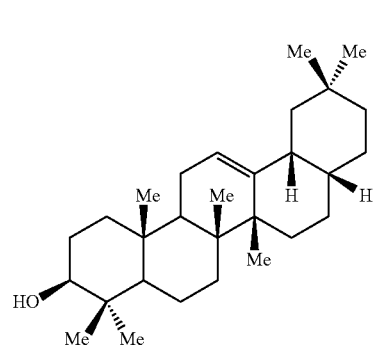

28-nor-beta-amyrin

-continued

Name: 28-nor-beta-amyrone

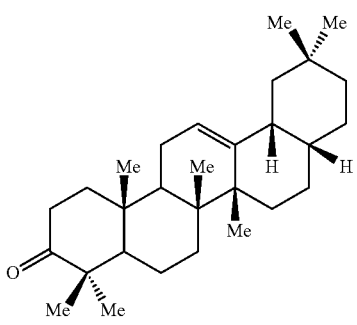

28-nor-beta-amyrone

Name: 3-oxo-28-norlup-20(29)-ene (28-nor-betulone)

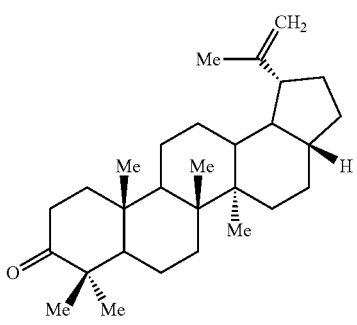

Name: 3-oxo-28nor-17-hydroxy-20(29)-ene (28-nor-17-hydroxybetulone)

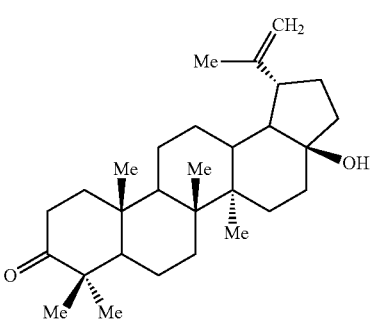

As used herein, the term "essential oil" refers to a volatile oil derived from the leaves, stem, flower or twigs of plants or synthetically-made compounds that have the same chemical attributes. The essential oil usually carries the odor or flavor of the plant. Each plant essential oil or derivative thereof may be extracted from natural sources or synthetically made. Chemically essential oils generally contain mixtures of mono- and sesquiterpenes or corresponding mixtures of such terpenoids as major constituents, which have lower molecular weights in comparison with triterpenes and titerpenoids. Particularly, this group comprise saturated and unsaturated acyclic monoterpenes or sesquiterpenes including alcohol or aldehyde moieties, benzenoid aromatic compounds containing at least one oxygenated substituent or side chain, or a monocarbocyclic terpene generally having a six-membered ring bearing one or more oxygenated substituents. The mastic resin contains about 2-4% of such compounds. As used herein, "essential oil" further includes derivatives thereof, including racemic mixtures, enantiomers, diastereomers, hydrates, salts, solvates, metabolites, analogs, and homologs.

As used herein, "substantially devoid" means that a preparation or pharmaceutical composition according to the invention that generally contains less than about 5% of the stated substance. For example, less than about 3%, less than 1%, less than 0.5%, less than 0.1%.

As used herein, the term "consisting essentially of" means that the only active pharmaceutical ingredient in the formulation or method that treats a specified condition is the specifically recited therapeutic ingredient in the particular embodiment or claim. The presence of other ingredients, e.g., excipients and/or lubricants, etc., is not precluded. The presence of additional other pharmaceutically active agents is also not precluded, as long as the latter do not have actual effect on said condition.

As used herein, "therapeutically effective amount" refers to that amount of a pharmaceutical ingredient which substantially induces, promotes or results in a desired therapeutic effect.

As used herein, "pharmaceutically acceptable carrier" refers to a diluent or vehicle, which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutically acceptable hydrophobic carrier" refers to a hydrophobic non-polar diluent or vehicle in which a composition is dissolved or suspended.

As used herein, "tauopathies" are a group of neurodegenerative diseases associated with pathological aggregation of so-called tau-protein in gliofibrillary or neurofibrillary tangles. Tau protein in its normal state is highly soluble and belongs to the class of microtubule-associated-proteins (MAPs) These tangles (also known as "paired helical filaments" are formed through hyperphosphorylation of tau-protein which results in aggregation into an insoluble form. Tauopathies can be divided into two groups, primary and secondary tauopathies. Non-limiting examples of primary tauopathies are Primary age-related tauopathy (PART, also known as neurofibrillary tangle-predominant senile dementia; Dementia puglilistica (chronic traumatic encephalopathy); Progressive Supranuclear Palsy (PSP); Corticobasal degeneration; Frontotemporal dementia and Parkinsonism linked to chromosome 17; Pick's disease; Ganglioma; Gangliocytoma; Meningoangiomatosis; Postencephalitic parkinsonism; Subacute Sclerosing Panencephalitis.

As used herein, alpha-synucleinopathies (synucleinopathies) are neurodegenerative diseases characterized by the abnormal accumulation of aggregates of the alpha-synuclein protein in neurons, nerve fibers or glial cells.

Parkinson's disease (PD) is a debilitating neurodegenerative disorder characterized by the progressive loss of dopaminergic (DA) neurons in the substantia nigra pars compacta (SNc), leading to a marked dopamine (DA) depletion in striatum, the primary projection region, as well as extrastriatal nuclei of the basal ganglia. PD has a characteristic clinical syndrome of bradykinesia, tremor, rigidity, and postural instability. There are a large number of different disorders that can have some or all of these clinical features, and the clinical syndrome is referred to as "parkinsonism". Disorders in which parkinsonism is a prominent part are referred to as "parkinsonian disorders." PD is one of a host of parkinsonian disorders. Degenerative parkinsonian disorders can be inherited or sporadic, but are all characterized by neuronal loss in selective populations of vulnerable neurons. The common denominator of all degenerative parkinsonian disorders is loss of dopaminergic neurons of the substantia nigra that project to the putamen (i.e., dopaminergic nigrostriatal pathway). Parkinson-plus syndromes include such conditions as, multiple system atrophy (MSA), Progressive supranuclear palsy (PSP), Parkinsonism-dementia-amyotrophic lateral sclerosis complex, Corticobasal ganglionic degeneration (CBD) and Dementia with Lewy bodies (DLB).

As used herein the term "about" in reference to a numerical value stated herein is to be understood as the stated value+/−10%.

Compositions Comprising Triterpenoic Acids and Neutral Triterpenoids

In some embodiments, the present invention provides compositions comprising or consisting of specific triterpenoic acids and neutral triterpenoids, these compositions are shown to have an unexpected synergetic therapeutic effect in the treatment of Alzheimer's disease (AD), Parkinson's Diseases (PD) and/or vascular dementia (VD).

In some embodiments, the present invention provides compositions comprising or consisting of specific triterpenoic acids and neutral triterpenoids, these compositions are shown to have an unexpected synergetic therapeutic effect in the treatment of related conditions, such as, Multiple System Atrophy (MSA) and Progressive Supranuclear Palsy (PSP).

In some embodiments, the present invention provides compositions comprising or consisting of specific triterpenoic acids and neutral triterpenoids, these compositions are shown to have an unexpected synergetic therapeutic effect in the treatment of tauopathic diseases and conditions.

The triterpenoic acids and neutral triterpenoid compounds may be obtained from a plant source, such as for example mastic gum, or may be the products of chemical synthesis reactions. In some embodiments, any one of the triterpenoic acids and neutral triterpenoids may be the product of a biochemical reaction or a product produced by a microbial organism. In some embodiments, any one of the triterpenoic acids and neutral triterpenoids may be the product of a fermentation process. In some embodiments, any one of the triterpenoic acids and neutral triterpenoids may produced by a combination of a chemical synthesis and a biochemical reaction. In some embodiments, any one of the triterpenoic acids and neutral triterpenoids may be produced by a combination of a chemical synthesis and a fermentation process. In some embodiments, any one of the triterpenoic acids and neutral triterpenoids may be produced by a combination of any of the aboveindicated options. In case of a biochemical reaction or microbial process, the biochemical agent and the microbial agent may be a naturally occurring agent or may be a modified agent not naturally occurring. Modification of these agents may be achieved using modern biochemical methods such as for example genetic engineering. Said biochemical agents and microbial agents not occurring naturally may also be created using synthetic biology methods.

The current invention relates to the unexpected biological and pharmaceutical properties of the disclosed pharmaceutical compositions comprising triterpenoic acid(s) and neutral triterpenoid(s). The combination of triterpenoic acid(s) and neutral triterpenoid(s) results in an overall pharmaceutical activity which cannot be obtained by using only the triterpenoic acids or only the neutral triterpenoids.

In some embodiments, the compositions may correspond to combinations of compounds in which some are chemically synthesized and some are derived from plant sources.

In some embodiments, the compositions may correspond to combinations of compounds in which each compound may independently have been derived from a plant source, or may be the product of a chemical synthesis, a biochemical reaction, or a microbial process (e.g. fermentation) as indicated above.

In some embodiments, the present invention provides compositions comprising combinations comprising or consisting of at least one triterpenoic acid and at least one neutral triterpenoid having therapeutic activity, as detailed herein. In some embodiments, the present invention provides compositions comprising combinations comprising at least one triterpenoic acid and at least one neutral triterpenoid having therapeutic activity, and a pharmaceutically acceptable carrier. In some embodiments, there is provided a composition comprising at least one triterpenoic acid, at least one neutral triterpenoid and a pharmaceutically acceptable carrier.

In some embodiments, the triterpenoic acid may be selected from at least one of masticadienonic acid (MDA), isomasticadienonic acid (IMDA), masticadienolic acid (MLA), isomasticadienolic acid (IMLA), 3-O-acetyl masticadienolic acid, 3-O-acetyl epimasticadienolic acid, 3-O-acetyl isomasticadienolic acid, 3-O-acetyl epi-isomasticadienolic acid, oleanonic acid (OA) and moronic acid (MA), or any combination thereof. Each possibility is a separate embodiment.

In some embodiments, when MDA is one of the triterpenoic acids, MDA may comprise about 2-80% of the total weight of the triterpenoic acids. In some embodiments, MDA may comprise about 10-70% of the total weight of the triterpenoic acids. In some embodiments, MDA may comprise about 15-60% of the total weight of the triterpenoic acids. In some embodiments, MDA may comprise about 20-50% of the total weight of the triterpenoic acids. In some embodiments, MDA may comprise about 20-40% of the total weight of the triterpenoic acids. In some embodiments, MDA may comprise about 40-50% of the total weight of the triterpenoic acids. In some embodiments, MDA may comprise about 50% of the total weight of the triterpenoic acids.

In some embodiments, when IMDA is one of the triterpenoic acids, IMDA may comprise about 2-80% of the total weight of the triterpenoic acids. In some embodiments, IMDA may comprise about 10-70% of the total weight of the triterpenoic acids. In some embodiments, IMDA may comprise about 15-60% of the total weight of the triterpenoic acids. In some embodiments, IMDA may comprise about 20-50% of the total weight of the triterpenoic acids. In some embodiments, IMDA may comprise about 20-40% of the total weight of the triterpenoic acids. In some embodiments, IMDA may comprise about 40-50% of the total weight of the triterpenoic acids. In some embodiments, IMDA may comprise about 50% of the total weight of the triterpenoic acids.

In some embodiments, when MLA is one of the triterpenoic acids, MLA may comprise about 0-80% of the total weight of the triterpenoic acids. In some embodiments, MLA may comprise about 0-70% of the total weight of the triterpenoic acids. In some embodiments, MLA may comprise about 0-25% of the total weight of the triterpenoic acids. In some embodiments, MLA may comprise about 0-15% of the total weight of the triterpenoic acids. In some embodiments, MLA may comprise about 8% of the total weight of the triterpenoic acids.

In some embodiments, when IMLA is one of the triterpenoic acids, IMLA may comprise about 0-80% of the total weight of the triterpenoic acids. In some embodiments, IMLA may comprise about 0-70% of the total weight of the triterpenoic acids. In some embodiments, IMLA may comprise about 0-25% of the total weight of the triterpenoic acids. In some embodiments, IMLA may comprise about 0-15% of the total weight of the triterpenoic acids. In some embodiments, IMLA may comprise about 8% of the total weight of the triterpenoic acids.

In some embodiments, when MA is one of the triterpenoic acids, MA may comprise about 0-80% of the total weight of the triterpenoic acids. In some embodiments, MA may comprise about 0-70% of the total weight of the triterpenoic acids. In some embodiments, MA may comprise about 0-40% of the total weight of the triterpenoic acids. In some embodiments, MA may comprise about 0-30% of the total weight of the triterpenoic acids. In some embodiments, MA may comprise about 5-20% of the total weight of the triterpenoic acids. In some embodiments, MA may comprise about 12-15% of the total weight of the triterpenoic acids.

In some embodiments, when OA is one of the triterpenoic acids, OA may comprise about 0-80% of the total weight of the triterpenoic acids. In some embodiments, OA may comprise about 0-70% of the total weight of the triterpenoic acids. In some embodiments, OA may comprise about 0-50% of the total weight of the triterpenoic acids. In some embodiments, OA may comprise about 5-35% of the total weight of the triterpenoic acids. In some embodiments, OA may comprise about 10-25% of the total weight of the triterpenoic acids. In some embodiments, MA may comprise about 18-20% of the total weight of the triterpenoic acids.

In some embodiments, when 3-O-acetyl masticadienolic acid is one of the triterpenoic acids, 3-O-acetyl masticadienolic acid may comprise about 0-80% of the total weight of the triterpenoic acids. In some embodiments, 3-O-acetyl masticadienolic acid may comprise about 0-70% of the total weight of the triterpenoic acids. In some embodiments, 3-O-acetyl masticadienolic acid may comprise about 0-25% of the total weight of the triterpenoic acids. In some embodiments, 3-O-acetyl masticadienolic acid may comprise about 0-15% of the total weight of the triterpenoic acids. In some embodiments, 3-O-acetyl masticadienolic acid may comprise about 4-7% of the total weight of the triterpenoic acids.

In some embodiments, when 3-O-acetyl isomasticadienolic acid is one of the triterpenoic acids, 3-O-acetyl isomasticadienolic acid may comprise about 0-80% of the total weight of the triterpenoic acids. In some embodiments, 3-O-acetyl isomasticadienolic acid may comprise about 0-70% of the total weight of the triterpenoic acids. In some embodiments, 3-O-acetyl isomasticadienolic acid may comprise about 0-25% of the total weight of the triterpenoic acids. In some embodiments, 3-O-acetyl isomasticadienolic acid may comprise about 0-15% of the total weight of the triterpenoic acids. In some embodiments, 3-O-acetyl isomasticadienolic acid may comprise about 4-7% of the total weight of the triterpenoic acids.

In some embodiments, when 3-O-acetyl-epimasticadienolic acid is one of the triterpenoic acids, 3-O-acetyl masticadienolic acid may comprise about 0-80% of the total weight of the triterpenoic acids. In some embodiments, 3-O-acetyl epimasticadienolic acid may comprise about 0-70% of the total weight of the triterpenoic acids. In some embodiments, 3-O-acetyl masticadienolic acid may comprise about 0-25% of the total weight of the triterpenoic acids. In some embodiments, 3-O-acetyl epimasticadienolic acid may comprise about 0-15% of the total weight of the triterpenoic acids. In some embodiments, 3-O-acetyl epimasticadienolic acid may comprise about 4-7% of the total weight of the triterpenoic acids.

In some embodiments, when 3-O-acetyl epiisomasticadienolic acid is one of the triterpenoic acids, 3-O-acetyl epiisomasticadienolic acid may comprise about 0-80% of the total weight of the triterpenoic acids. In some embodiments, 3-O-acetyl epiisomasticadienolic acid may comprise about 0-70% of the total weight of the triterpenoic acids. In some embodiments, 3-O-acetyl epiisomasticadienolic acid may comprise about 0-25% of the total weight of the triterpenoic acids. In some embodiments, 3-O-Acetyl epiisomasticadienolic acid may comprise about 0-15% of the total weight of the triterpenoic acids. In some embodiments, 3-O-Acetyl epimasticadienolic acid may comprise about 4-7% of the total weight of the triterpenoic acids.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, when NF-1 is one of the neutral triterpenoids, the amount of NF-1 with respect to the total amount of neutral triterpenoids may be in the range of about 0% to about 80%. In some embodiments, the amount of NF-1 with respect to the total amount of neutral triterpenoids may be in the range of about 0% to about 50%. In some embodiments, the amount of NF-1 with respect to the total amount of neutral triterpenoids may be in the range of about 5% to about 25%. In some embodiments, the amount of NF-1 with respect to the total amount of neutral triterpenoids may be in the range of about 9% to about 13%.

In some embodiments, when NF-2 is one of the neutral triterpenoids, the amount of NF-2 with respect to the total amount of neutral triterpenoids may be in the range of about 0% to about 80%. In some embodiments, the amount of NF-2 with respect to the total amount of neutral triterpenoids may be in the range of about 0% to about 50%. In some embodiments, the amount of NF-2 with respect to the total amount of neutral triterpenoids may be in the range of about 5% to about 25%. In some embodiments, the amount of NF-2 with respect to the total amount of neutral triterpenoids may be in the range of about 9% to about 13%.

In some embodiments, when NF-3 is one of the neutral triterpenoids, the amount of NF-3 with respect to the total amount of neutral triterpenoids may be in the range of about 0% to about 80%. In some embodiments, the amount of NF-3 with respect to the total amount of neutral triterpenoids may be in the range of about 0% to about 50%. In some embodiments, the amount of NF-3 with respect to the total amount of neutral triterpenoids may be in the range of about 5% to about 25%. In some embodiments, the amount of NF-3 with respect to the total amount of neutral triterpenoids may be in the range of about 9% to about 13%.

In some embodiments, when NF-4 is one of the neutral triterpenoids, the amount of NF-4 with respect to the total amount of neutral triterpenoids may be in the range of about 0% to about 80%. In some embodiments, the amount of NF-4 with respect to the total amount of neutral triterpenoids may be in the range of about 0% to about 50%. In some embodiments, the amount of NF-4 with respect to the total amount of neutral triterpenoids may be in the range of about 5% to about 25%. In some embodiments, the amount of NF-4 with respect to the total amount of neutral triterpenoids may be in the range of about 9% to about 13%.

In some embodiments, when NF-P is one of the neutral triterpenoids, the amount of NF-P with respect to the total amount of neutral triterpenoids may be in the range of about 0% to about 50%. In some embodiments, the amount of NF-P with respect to the total amount of neutral triterpenoids may be in the range of about 0% to about 25%. In some embodiments, the amount of NF-P with respect to the total amount of neutral triterpenoids may be in the range of about 0% to about 7%. In some embodiments, the amount of NF-P with respect to the total amount of neutral triterpenoids may be in the range of about 6% to about 7%.

In some embodiments, when NF-A is one of the neutral triterpenoids, the amount of NF-A with respect to the total amount of neutral triterpenoids may be in the range of about 0% to about 25%. In some embodiments, the amount of NF-A with respect to the total amount of neutral triterpenoids may be in the range of about 0% to about 15%. In some embodiments, the amount of NF-A with respect to the total amount of neutral triterpenoids may be in the range of about 0% to about 6%. In some embodiments, the amount of NF-A with respect to the total amount of neutral triterpenoids may be in the range of about 4% to about 6%.

In some embodiments, when NF-B is one of the neutral triterpenoids, the amount of NF-B with respect to the total amount of neutral triterpenoids may be in the range of about 0% to about 25%. In some embodiments, the amount of NF-B with respect to the total amount of neutral triterpenoids may be in the range of about 0% to about 15%. In some embodiments, the amount of NF-B with respect to the total amount of neutral triterpenoids may be in the range of about 0% to about 6%. In some embodiments, the amount of NF-B with respect to the total amount of neutral triterpenoids may be in the range of about 4% to about 6%.

In some embodiments, the triterpenoic acids may comprise from about 1% to about 80% of the total active ingredients of the composition. In some embodiments, the triterpenoic acids may comprise from about 10% to about 80% of the total active ingredients of the composition. In some embodiments, the triterpenoic acids may comprise from about 20% to about 80% of the total active ingredients of the composition. In some embodiments, the triterpenoic acids may comprise from about 30% to about 70% of the total active ingredients of the composition. In some embodiments, the triterpenoic acids may comprise from about 35% to about 65% of the total active ingredients of the composition. In some embodiments, the triterpenoic acids may comprise from about 40% to about 60% of the total active ingredients of the composition.

In some embodiments, the triterpenoic acids may comprise from about 0.01% to about 80% of the total composition. In some embodiments, the triterpenoic acids may comprise from about 0.01% to about 50% of the total composition. In some embodiments, the triterpenoic acids may comprise from about 0.01% to about 10% of the total composition. In some embodiments, the triterpenoic acids may comprise from about 0.1% to about 10% of the total composition. In some embodiments, the triterpenoic acids may comprise from about 0.5% to about 4% of the total composition. In some embodiments, the triterpenoic acids may comprise from about 1% to about 3.5% of the total composition. In some embodiments, the triterpenoic acids may comprise from about 1.5% to about 3% of the total composition. In some embodiments, the triterpenoic acids may comprise from about 1.75% to about 2.75% of the total composition. In some embodiments, the triterpenoic acids may comprise from about 2% to about 2.5% of the total composition.

In some embodiments, the neutral triterpenoids may comprise from about 1% to about 80% of the total active ingredients of the composition. In some embodiments, the neutral triterpenoids may comprise from about 10% to about 80% of the total active ingredients of the composition. In some embodiments, the neutral triterpenoids may comprise from about 20% to about 80% of the total active ingredients of the composition. In some embodiments, the neutral triterpenoids may comprise from about 30% to about 70% of the total active ingredients of the composition. In some embodiments, the neutral triterpenoids may comprise from about 35% to about 65% of the total active ingredients of the composition. In some embodiments, the neutral triterpenoids may comprise from about 40% to about 60% of the total active ingredients of the composition.

In some embodiments, the neutral triterpenoids may comprise from about 0.01% to about 80% of the total composition. In some embodiments, the neutral triterpenoids may comprise from about 0.01% to about 50% of the total composition. In some embodiments, the neutral triterpenoids may comprise from about 0.01% to about 10% of the total composition. In some embodiments, the neutral triterpenoids may comprise from about 0.1% to about 10% of the total composition. In some embodiments, the neutral triterpenoids may comprise from about 0.5% to about 4% of the total composition. In some embodiments, the neutral triterpenoids may comprise from about 1% to about 3.5% of the total composition. In some embodiments, the neutral triterpenoids may comprise from about 1.5% to about 3% of the total composition. In some embodiments, the neutral triterpenoids may comprise from about 1.75% to about 2.75% of the total composition. In some embodiments, the neutral triterpenoids may comprise from about 2% to about 2.5% of the total composition.

In some embodiments, the combinations comprise at least one of MDA and IMDA as the triterpenoic acids and at least one of NF-1 and NF-2 as the neutral triterpenoids.

In some embodiments, the combinations may include at least one of MDA and IMDA as the triterpenoic acids and at least one of NF-1 and NF-2 as the neutral triterpenoids.

In some embodiments, the combinations may include at least MDA as the triterpenoic acid and at least NF-1 as the neutral triterpenoid.

In some embodiments, the combinations may include at least MDA as the triterpenoic acid and at least NF-2 as the neutral triterpenoid.

In some embodiments, the combinations may include at least IMDA as the triterpenoic acid and at least NF-1 as the neutral triterpenoid.

In some embodiments, the combinations may include at least IMDA as the triterpenoic acid and at least NF-2 as the neutral triterpenoid.

In some embodiments, the combinations may include at least MDA and IMDA as the triterpenoic acids and at least NF-1 and NF-2 as the neutral triterpenoids.

In some embodiments, the combinations may include at least MDA and IMDA as the triterpenoic acids and at least NF-1, NF-2, NF-3 and NF-4 as the neutral triterpenoids. In some embodiments, the combinations may include at least MDA and IMDA as the triterpenoic acids and at least NF-1, NF-2, NF-3, NF-4, NF-A, NF-B, NF-P as the neutral triterpenoids. In some embodiments, the combinations may include at least MDA and IMDA as the triterpenoic acids and at least NF-1, NF-2, NF-3, NF-4, NF-A, and NF-B as the neutral triterpenoids. In some embodiments, the combinations may include at least MDA, MLA, IMDA and IMLA as the triterpenoic acids and at least NF-1, NF-2, NF-3 and NF-4 as the neutral triterpenoids. In some embodiments, the combinations may include at least MDA, MLA, IMDA and IMLA as the triterpenoic acids and at least NF-1, NF-2, NF-3, NF-4, NF-A, NF-B and NF-P as the neutral triterpenoids. In some embodiments, the combinations may include at least MDA, MLA, IMDA and IMLA as the triterpenoic acids and at least NF-1, NF-2, NF-3, NF-4, NF-A and NF-B as the neutral triterpenoids. Such compositions unexpectedly exhibit a synergistic effect, whereby the combination of compounds exhibit a markedly improved therapeutic effect in the treatment of conditions, such as Alzheimer's disease (AD), Parkinson's Diseases (PD) and/or vascular dementia (VD).

In some embodiments, the neutral triterpenoid comprises at least NF-1 and at least one additional neutral triterpenoid. In some embodiments, the neutral triterpenoid comprises at least NF-2 and at least one additional neutral triterpenoid. In some embodiments, the neutral triterpenoid comprises at least NF-1, NF-2 and at least one additional neutral triterpenoid. In some embodiments, the additional neutral triterpenoid is selected from the group consisting of NF-1, NF-2, NF-3, NF-4, NF-A, NF-B and NF-P. In some embodiments, the additional neutral triterpenoid is selected from the group consisting of NF-1, NF-2, NF-3, NF-4, NF-A and NF-B. Each possibility is a separate embodiment. In some embodiments, the additional neutral triterpenoid is selected from the group consisting of NF-2, NF-3, NF-4, NF-A, NF-B, and NF-P. In some embodiments, the additional neutral triterpenoid is selected from the group consisting of NF-2, NF-3, NF-4, NF-A and NF-B. In some embodiments, the additional neutral triterpenoid is selected from the group consisting of NF-1, NF-3, NF-4, NF-A, NF-B and NF-P. In some embodiments, the additional neutral triterpenoid is selected from the group consisting of NF-1, NF-3, NF-4, NF-A and NF-B. In some embodiments, the additional neutral triterpenoid is selected from the group consisting of NF-3, NF-4, NF-A, NF-B and NF-P. In some embodiments, the additional neutral triterpenoid is selected from the group consisting of NF-3, NF-4, NF-A and NF-B. In some embodiments, the additional neutral triterpenoid is selected from NF-3 and Tirucallol NF-4. Various combinations of some of these compounds exhibit an unexpected synergistic effect in the treatment of Alzheimer's disease (AD), Parkinson's Diseases (PD) and/or vascular dementia (VD). Various combinations of some of these compounds exhibit an unexpected synergistic effect in the treatment of conditions, such as, Multiple System Atrophy (MSA) and Progressive Supranuclear Palsy (PSP). Various combinations of some of these compounds exhibit an unexpected synergistic effect in the treatment of various tauopathic diseases and conditions.

In some embodiments, there is provided a composition comprising at least one of MDA and IMDA as the triterpenoic acid and at least one of NF-1 and NF-2 as the neutral triterpenoid.

In some embodiments, there is provided a composition comprising at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA, in addition to at least one of NF-1, NF-2, NF-3, NF-4, NF-A, NF-B and NF-P. Each possibility is a separate embodiment of the invention.

In some embodiments, there is provided a composition comprising at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA, in addition to at least one of NF-1, NF-2, NF-3, NF-4, NF-A and NF-B. Each possibility is a separate embodiment of the invention.

In some embodiments, the composition comprises at least one of masticadienonic acid MDA, IMDA, MLA, IMLA, 3-O-acetyl masticadienolic acid, 3-O-acetyl isomasticadienolic acid, OA and MA; in addition to at least one of NF-1, NF-2, NF-3 and NF-4. In some embodiments, the composition comprises at least one of MDA and IMDA; in addition to at least one of NF-1, NF-2, NF-3 and NF-4. In some embodiments, the composition comprises at least one of MDA and IMDA; in addition to at least one of NF-1, NF-2, NF-3, NF-4, NF-A, NF-B and NF-P. In some embodiments, the composition comprises at least one of MDA and IMDA; in addition to at least one of NF-1, NF-2, NF-3, NF-4, NF-A and NF-B. In some embodiments the composition may further include a pharmaceutically acceptable carrier. Each possibility is a separate embodiment of the invention.

In some embodiments, there is provided a composition comprising at least one of NF-1 and NF-2, in addition to at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA; and at least one of NF-3, NF-4, NF-A, NF-B and NF-P.

In some embodiments, there is provided a composition comprising at least one of NF-1 and NF-2, in addition to at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA and MA; and at least one of NF-3, NF-4, NF-A and NF-B.

In some embodiments, there is provided a composition comprising NF-1, NF-2, at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid; OA, MA, and at least one of NF-3, NF-4, NF-A, NF-B and NF-P.

In some embodiments, there is provided a composition comprising NF-1, NF-2, at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid; OA, MA, and at least one of NF-3, NF-4, NF-A and NF-B.

In some embodiments, there is provided a composition comprising at least one of NF-1 and NF-2, in addition to at least one of MDA, IMDA, MLA, IMLA, 3-O-acetyl masticadienolic acid, 3-O-acetyl isomasticadienolic acid, OA and MA, and at least one of NF-3 and NF-4.

In some embodiments, there is provided a composition comprising NF-1 and NF-2, in addition to at least one of masticadienonic acid MDA, IMDA, MLA, IMLA, 3-O-acetyl masticadienolic acid, 3-O-acetyl isomasticadienolic acid, OA and MA, and at least one of NF-3 and NF-4.

In some embodiments, there is provided a composition comprising at least one of NF-1 and NF-2 in addition to at least one of MDA, IMDA, MLA and IMLA, and at least one of NF-3, NF-4, NF-A, NF-B and NF-P.

In some embodiments, there is provided a composition comprising at least one of NF-1 and NF-2 in addition to at least one of MDA, IMDA, MLA and IMLA, and at least one of NF-3, NF-4, NF-A and NF-B.

In some embodiments, there is provided a composition comprising NF-1 and NF-2, in addition to at least one of MDA, IMDA, MLA and IMLA, and at least one of NF-3, NF-4, NF-A, NF-B and NF-P.

In some embodiments, there is provided a composition comprising NF-1 and NF-2, in addition to at least one of MDA, IMDA, MLA and IMLA, and at least one of NF-3, NF-4, NF-A and NF-B.

In some embodiments, there is provided a composition comprising at least one of NF-1 and NF-2, in addition to at least one of masticadienonic acid MDA and IMDA; and at least one of NF-3 and NF-4.

In some embodiments, there is provided a composition comprising NF-1 and NF-2, in addition to at least one of MDA and IMDA; and at least one of NF-3 and NF-4.

In some embodiments, there is provided a composition comprising at least one of NF-1 and NF-2, in addition to at least one of MDA, IMDA, MLA, IMLA, 3-O-acetyl masticadienolic acid, 3-O-acetyl isomasticadienolic acid, OA and MA, and at least one of NF-3, NF-4, NF-A, NF-B and NF-P.

In some embodiments, there is provided a composition comprising at least one of NF-1 and NF-2, in addition to at least one of MDA, IMDA, MLA, IMLA, 3-O-acetyl masticadienolic acid, 3-O-acetyl isomasticadienolic acid, OA and MA, and at least one of NF-3, NF-4, NF-A and NF-B.

In some embodiments, there is provided a composition comprising NF-1 and NF-2, in addition to at least one of MDA, IMDA, MLA, IMLA, 3-O-acetyl masticadienolic acid, 3-O-acetyl isomasticadienolic acid, OA and MA, and at least one of NF-3, NF-4, NF-A, NF-B and NF-P.

In some embodiments, there is provided a composition comprising NF-1 and NF-2, in addition to at least one of MDA, IMDA, MLA, IMLA, 3-O-acetyl masticadienolic acid, 3-O-acetyl isomasticadienolic acid, OA and MA, and at least one of NF-3, NF-4, NF-A and NF-B.

In some embodiments, there is provided a composition comprising at least one of NF-1 and NF-2, in addition to at least one of masticadienonic acid MDA and IMDA; and at least one of NF-3, NF-4, NF-A, NF-B and NF-P.

In some embodiments, there is provided a composition comprising at least one of NF-1 and NF-2, in addition to at least one of masticadienonic acid MDA and IMDA; and at least one of NF-3, NF-4, NF-A and NF-B.

In some embodiments, there is provided a composition comprising NF-1 and NF-2, in addition to at least one of MDA and IMDA and at least one of NF-3, NF-4, NF-A, NF-B and NF-P.

In some embodiments, there is provided a composition comprising NF-1 and NF-2, in addition to at least one of MDA and IMDA and at least one of NF-3, NF-4, NF-A and NF-B.

In some embodiments, there is provided a composition comprising NF-1 and NF-2, in addition to at least one of MDA and IMDA.

In some embodiments, the composition may include not more than 15 triterpenoids. In some embodiments, the composition may include not more than 14 triterpenoids. In some embodiments, the composition may include not more than 13 triterpenoids. In some embodiments, the composition may include not more than 12 triterpenoids. In some embodiments, the composition may include not more than 11 triterpenoids. In some embodiments, the composition may include not more than 10 triterpenoids. In some embodiments, the composition may include not more than 9 triterpenoids. In some embodiments, the composition may include not more than 8 triterpenoids. In some embodiments, the composition may include not more than 7 triterpenoids. In some embodiments, the composition may include not more than 6 triterpenoids.

In some embodiments, there is provided a combination comprising at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid; OA and MA; in addition to at least one of NF-1, NF-2, NF-3, NF-4, NF-A, NF-B and NF-P. Each possibility is a separate embodiment of the invention. In some embodiments, there is provided a combination comprising at least one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid; OA and MA; in addition to at least one of NF-1, NF-2, NF-3, NF-4, NF-A and NF-B. Each possibility is a separate embodiment of the invention.

In some embodiments, the combination comprises at least one of MDA, IMDA, MLA, IMLA, 3-O-acetyl masticadienolic acid, 3-O-acetyl isomasticadienolic acid, OA and MA; in addition to at least one of NF-1, NF-2, NF-3 and NF-4. In some embodiments, the combination comprises at least one of MDA and IMDA; in addition to at least one of (NF-1, NF-2, NF-3 and NF-4. In some embodiments, the combination comprises at least one of MDA and IMDA; in addition to at least one of NF-1, NF-2, NF-3, NF-4, NF-A, NF-B and NF-P. In some embodiments, the combination comprises at least one of MDA and IMDA; in addition to at least one of NF-1, NF-2, NF-3, NF-4, NF-A and NF-B. In some embodiments, the combination may further include a pharmaceutically acceptable carrier.

In some embodiments, the composition further comprises at least one neutral triterpenoid selected from the group consisting of: 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene. Each possibility is a separate embodiment of the invention.

In some embodiments, the composition further comprises at least one neutral triterpenoid selected from the group consisting of: 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene. Each possibility is a separate embodiment of the invention.

In some embodiments, in a composition comprising more than one triterpenoic acid, and if present in such composition, IMDA and MDA are present at a ratio of about 1:1 w/w.

In some embodiments, in a composition comprising more than one triterpenoic acid, and if present in such composition, MDA, IMDA, MLA IMLA are present at a ratio of about 1:1:0.2:0.2 (5:5:1:1) w/w respectively.

In some embodiments, if present in such composition IMDA, MDA, NF-1, NF-2, NF-3 and NF-4 are present at a ratio of about 1:1:0.5:0.5:0.5:0.33 (6:6:3:3:3:2) w/w respectively.

In some embodiments, if present in such composition IMDA, MDA, NF-1, NF-2, NF-3, NF-4, NF-P, NF-A, and NF-B are present at a ratio of about 1:1:0.5:0.5:0.5:0.33:0.33:0.25:0.25 (12:12:6:6:6:4:4:3:3) w/w respectively.

In some embodiments, if present in such composition IMDA, MDA, NF-1, NF-2, NF-3, NF-4, NF-A, and NF-B are present at a ratio of about 1:1:0.5:0.5:0.5:0.33:0.25:0.25 (12:12:6:6:6:4:4:3:3) w/w respectively.

In some embodiments, if present in such composition, IMDA, MDA, NF-1 and NF-2 are present at a ratio of about 1:1:0.5:0.5 (2:2:1:1) w/w respectively.

In some embodiments, if present in such composition, IMDA, MDA, OA, 3-O-acetyl-masticadienolic acid, 3-O-acetyl-isomasticadienolic acid, NF-1 and NF-2 are present at a ratio of about 2:2:0.75:0.75:1.5:1:1:0.67 w/w respectively.

In some embodiments, if present in such composition, NF-1, NF-2, NF-3 and NF-4 present at a ratio of about 1:1:1:0.67 (3:3:3:2) w/w respectively.

In some embodiments, if present in such composition, NF-1, NF-2, NF-3, NF-4, NF-P, NF-A, and NF-B are present at a ratio of about 1:1:1:0.67:0.67:0.5:0.5 (6:6:6:4:4:3:3) respectively.

In some embodiments, if present in such composition, NF-1, NF-2, NF-3, NF-4, NF-A, and NF-B are present at a ratio of about 1:1:1:0.67:0.5:0.5 (6:6:6:4:4:3:3) respectively.

In some embodiments, the composition further comprises at least one neutral triterpenoid selected from the group consisting of: Beta-amyrone, Beta-amyrin and Germanicol. Each possibility is a separate embodiment of the invention.

In some embodiments, the combination may further comprise at least one triterpenoic acid selected from the group consisting of: oleanolic acid, ursonic acid and ursolic acid. Each possibility is a separate embodiment of the invention.

In some embodiments, the triterpenoic acid(s) may be obtained from a plant source. In some embodiments, any one of the triterpenoic acids may be obtained from a plant source. In some embodiments, at least one triterpenoic acid may be obtained from a plant source. In some embodiments, the neutral triterpenoid(s) may be obtained from a plant source. In some embodiments, any one of the neutral triterpenoids may be obtained from a plant source. In some embodiments, at least one neutral triterpenoid may be obtained from a plant source. In some embodiments, the plant source may include mastic gum.

In some embodiments, any one of the triterpenoic acids and/or the neutral triterpenoid may be isolated from a natural source or may be the product of a chemical synthesis. In some embodiments, the triterpenoic acids and/or the neutral triterpenoids may be isolated from a natural source or may be the product of a chemical synthesis.

In some embodiments, any one of the triterpenoic acids and neutral triterpenoids may be the product of a biochemical reaction or a product produced by a microbial organism. In some embodiments, any one of the triterpenoic acids and neutral triterpenoids may be the product of a fermentation process. In some embodiments, any one of the triterpenoic acids and neutral triterpenoids may produced by a combination of a chemical synthesis and a biochemical reaction. In some embodiments, any one of the triterpenoic acids and neutral triterpenoids may be produced by a combination of a chemical synthesis and a fermentation process. In some embodiments, the any one of triterpenoic acids and neutral triterpenoids may be produced by a combination of any of the aboveindicated options. In case of a biochemical reaction or microbial process, the biochemical agent and the microbial agent my be a naturally occurring agent or may be a modified agent not naturally occurring. Modification of these agents may have been achieved using modern biochemical methods such as for example genetic engineering. Said biochemical agents and microbial agents not occurring naturally may also have been created using synthetic biology methods.

In some embodiments, obtaining from a natural source may include isolating from a natural source. In some embodiments, the isolation from the natural source may include isolation as individual compound(s) or as a group(s) of compounds. In some embodiments, the natural source may include a plant material selected from the group consisting of a resin, a gum, leaves, twigs, roots, flowers, seeds, buds, bark, nuts and roots. Each possibility is a separate embodiment. In some embodiments, the natural source may include a resin extracted from at least one plant. In some embodiments, the natural source may include mastic gum.

In some embodiments, the natural source may include at least one plant. In some embodiments, the plant may be classified in the family Anacardiaceae. In some embodiments, the plant may comprise at least one plant classified in the genus/genera *Pistacia* and/or *Schinus*. In some embodiments, *Pistacia* may include species selected from the group consisting of *P. lentiscus*, *P. lentiscus Latifolia* Coss, *P. lentiscus* var. *Chia*, *P. atlantica*, *P. palestina*, *P. saportae*, *P. terebinthus*, *P. vera P. integerrima*, P and. *lentiscus* L. Each possibility is a separate embodiment. In some embodiments, *Pistacia* may include the species *Pistacia lentiscus* L. In some embodiments, *Schinus* may include the species *S. molle*. In some embodiments, the *Pistacia* may include the species *Pistacia Lentiscus* var. *Chia*.

In some embodiments, the triterpenoids may be obtained by a process comprising or consisting one or more of the steps of:
  (a) treating mastic gum with a polar organic solvent;
  (b) isolating a fraction soluble in said polar organic solvent;
  (c) optionally removing said polar organic solvent;
  (d) treating the soluble fraction obtained in step (b) or (c) with a non-polar organic solvent;
  (e) isolating a fraction soluble in said non-polar organic solvent;
  (f) optionally removing said non-polar organic solvent;
  (g) dissolving the fraction obtained in step (f) in a first organic solvent;
  (h) treatment of the solution obtained in step (g) or (e) with a basic aqueous solution so as to obtain a basic aqueous fraction containing triterpenoic acids in a deprotonated salt form and an intermediate oily or emulsion phase in addition to the first organic solution containing neutral triterpenoids;
  (i) separating said basic aqueous fraction and the intermediate oily/emulsion phase from the first organic solution
  (j) acidifying the basic aqueous fraction and emulsion obtained in step (i) with an acid;
  (k) extracting the acidified fraction obtained in step (j) with a second organic solvent;
  (l) optionally contacting the organic fraction obtained in step (k) with a drying agent;
  (m) removing the second organic solvent, the drying agent and/or excess acid from the fraction obtained in any of steps (j), (k) or (l) thus providing an isolated acidic fraction;
  (n) taking the first organic solution from step (i), optionally contacting it with a drying agent; and
  (o) removing the first organic solvent and the drying agent thus providing an isolated neutral fraction.

The individual triterpenoic acids can be obtained by chromatographic separation from the isolated acidic fraction obtained in step (m). The individual neutral triterpenoids can be obtained by chromatographic separation from the isolated neutral fraction obtained in step (o).

The individually obtained triterpenoic acids and neutral triterpenoids may then be mixed as required in order to obtain the desired pharmaceutical compositions.

In some embodiments, there is provided a composition comprising a combination of at least one triterpenoic acid and at least one neutral triterpenoid, and a pharmaceutically acceptable carrier, wherein the triterpenoic acid is selected from MDA, IMDA or both, wherein the neutral triterpenoid is selected from NF-1, NF-2, or both.

In some embodiments, the composition comprises MDA. In some embodiments, the composition comprises IMDA. In some embodiments, the composition comprises MDA and IMDA.

In some embodiments the composition further comprises at least one additional triterpenoic acid. In some embodiments, the additional triterpenoic acid is selected from the group consisting of MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA, MA and combinations thereof.

In some embodiments, the composition comprises at least two additional triterpenoic acids. In some embodiments, the composition comprises at least three additional triterpenoic acids. In some embodiments, the composition comprises at least four additional triterpenoic acids.

In some embodiments, the composition further comprises at least one additional neutral triterpenoid. In some embodiments, the additional neutral triterpenoid is selected from the group consisting of NF-3, NF-4, NF-A, NF-B, NF-P and combinations thereof.

In some embodiments, the composition comprises at least two additional neutral triterpenoids. In some embodiments, the composition comprises at least three additional neutral triterpenoids. In some embodiments, the composition comprises at least four additional neutral triterpenoids.

In some embodiments, the composition further comprises at least one additional neutral triterpenoid. In some embodiments, the additional neutral triterpenoid is selected from the group consisting of NF-3, NF-4, NF-A, NF-B and combinations thereof.

In some embodiments, the composition further comprises NF-P. In some embodiments, at least one of the additional neutral triterpenoids is selected from NF-3, NF-4 or both.

In some embodiments, the current invention provides a pharmaceutical composition consisting essentially of MDA, IMDA, NF-1, NF-2, NF-3 and NF-4 as the pharmaceutically active ingredients; and a pharmaceutically acceptable carrier. In some embodiments, the current invention provides a pharmaceutical composition consisting essentially of MDA, IMDA, MLA, IMLA, NF-1, NF-2, NF-3, NF-4, NF-A, NF-B and NF-P as the pharmaceutically active ingredients; and a pharmaceutically acceptable carrier. In some embodiments, the current invention provides a pharmaceutical composition consisting essentially of MDA, IMDA, MLA, IMLA, NF-1, NF-2, NF-3, NF-4, NF-A and NF-B as the pharmaceutically active ingredients; and a pharmaceutically acceptable carrier. In some embodiments, the current invention provides a pharmaceutical composition consisting essentially of MDA, IMDA, NF-1, NF-2, NF-3, NF-4, NF-A, NF-B and NF-P as the pharmaceutically active ingredients; and a pharmaceutically acceptable carrier. In some embodiments, the current invention provides a pharmaceutical composition consisting essentially of MDA, IMDA, NF-1, NF-2, NF-3, NF-4, NF-A and NF-B as the pharmaceutically acceptable carrier. In some embodiments, the current invention provides a pharmaceutical composition consisting essentially of MA, OA, MDA, IMDA 3-O-acetyl masticadienolic acid, 3-O-acetyl isomasticadienolic acid, MLA, IMLA, NF-1, NF-2, NF-3 and NF-4 as the pharmaceutically active ingredients; and a pharmaceutically acceptable carrier. In some embodiments, the current invention provides a pharmaceutical composition consisting essentially of MA, OA, MDA, IMDA 3-O-acetyl masticadienolic acid, 3-O-acetyl isomasticadienolic acid, MLA, IMLA, NF-1, NF-2, NF-3, NF-4, NF-A, NF-B and NF-P as the pharmaceutically active ingredients; and a pharmaceutically acceptable carrier. In some embodiments, the current invention provides a pharmaceutical composition consisting essentially of MA, OA, MDA, IMDA 3-O-acetyl masticadienolic acid, 3-O-acetyl isomasticadienolic acid, MLA, IMLA, NF-1, NF-2, NF-3, NF-4, NF-A and NF-B as the pharmaceutically active ingredients; and a pharmaceutically acceptable carrier. In some embodiments, there is provided a pharmaceutical composition comprising pharmaceutically active ingredients consisting essentially of MA, OA, MDA, IMDA, 3-O-acetyl masticadienolic acid, 3-O-acetyl isomasticadienolic acid, NF-1, NF-2, NF-3, NF-4, NF-A and NF-B; and a pharmaceutically acceptable carrier. In some embodiments, there is provided a pharmaceutical composition comprising pharmaceutically active ingredients consisting essentially of MA, OA, MDA, IMDA, 3-O-acetyl masticadienolic acid, 3-O-acetyl isomasticadienolic acid, NF-1, NF-2, NF-3 and NF-4; and a pharmaceutically acceptable carrier. In some embodiments, there is provided a pharmaceutical composition comprising pharmaceutically active ingredients consisting essentially of OA, MDA, IMDA, 3-O-acetyl masticadienolic acid, 3-O-acetyl isomasticadienolic acid, NF-1, NF-2, NF-3, NF-4, NF-A and NF-B; and a pharmaceutically acceptable carrier. In some embodiments, there is provided a pharmaceutical composition comprising pharmaceutically active ingredients consisting essentially of OA, MDA, IMDA, 3-O-acetyl masticadienolic acid, 3-O-acetyl isomasticadienolic acid, NF-1, NF-2, NF-3 and NF-4; and a pharmaceutically acceptable carrier. In some embodiments, there is provided a pharmaceutical composition comprising pharmaceutically active ingredients consisting essentially of MDA, IMDA, NF-1, NF-2; and a pharmaceutically acceptable carrier. In some embodiments, there is provided a pharmaceutical composition comprising pharmaceutically active ingredients consisting essentially of MDA, IMDA, NF-1, NF-2, NF-3, NF-4, NF-A and NF-B as the sole pharmaceutically active ingredients; and a pharmaceutically acceptable carrier. In some embodiments, there is provided a pharmaceutical composition comprising pharmaceutically active ingredients consisting essentially of MDA, IMDA, NF-1, NF-2, NF-3 and NF-4 as the sole pharmaceutically active ingredients; and a pharmaceutically acceptable carrier. In some embodiments, there is provided a pharmaceutical composition comprising pharmaceutically active ingredients consisting essentially of MDA, IMDA, NF-1 and NF-2 as the sole pharmaceutically active ingredients; and a pharmaceutically acceptable carrier.

Any one of the triterpenoic acids, neutral triterpenoids, additional triterpenoic acids and/or the additional neutral triterpenoids may be isolated from a natural source such as mastic gum, or may be the product of a chemical synthesis.

In some embodiments, any one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA, MA, NF-1, NF-2, NF-3, NF-4, NF-A, NF-B), and NF-P may be a product of a chemical synthesis. In some embodiments, any one of the at least one triterpenoic acid and the at least one neutral triterpenoid may be a product of a chemical synthesis.

In some embodiments, any one of MDA, IMDA, MLA, IMLA, 3-O-acetyl masticadienolic acid, 3-O-acetyl epimasticadienolic acid, 3-O-acetyl isomasticadienolic acid, 3-O-acetyl epi-isomasticadienolic acid, OA, MA, NF-1, NF-2, NF-3, NF-4, NF-A and NF-B may be a product of a chemical synthesis. In some embodiments, any one of the at least one triterpenoic acid and the at least one neutral triterpenoid may be a product of a chemical synthesis.

Plant species useful for obtaining the compositions of the invention include without limitation, those of the genus *Pistacia*. Useful species of *Pistacia* include without limitation, *P. lentiscus, P. lentiscus latifolius* Coss., *P. lentiscus* var. *Chia, P. atlantica, P. palestina, P. saportae, P. terebinthus, P. vera* and *P. integerrima*.

Analytical methods for determining the precise chemical structure of the triterpenoic acids and neutral triterpenoids include nuclear magnetic resonance (for example $^1$H-NMR and $^{13}$C-NMR), various mass spectrometry methods (for example MALDI-TOF), HPLC, combination methods such as Liquid Chromatography-Mass spectrometry (LC-MS; LC-MS/MS, UV-VIS spectrometry, IR and FT-IR spectrometry and other methods as are known in the art.

In some embodiments, the composition includes at least one triterpenoic acid and at least one neutral triterpenoid. In some embodiments, the triterpenoic acid may include masticadienonic acid (MDA), isomasticadienonic acid (IMDA), masticadienolic acid (MLA), isomasticadienolic acid (IMLA), 3-O-acetyl masticadienolic acid, 3-O-acetyl epimasticadienolic acid, 3-O-acetyl isomasticadienolic acid, 3-O-acetyl epi-isomasticadienolic acid, oleanonic acid (OA), moronic acid (MA), or any combination thereof. In some embodiments, the neutral triterpenoid may include 8-dihydroxypolypoda-13E,17E,21-triene (NF-1), (8R)-3-Oxo-8-hydroxypolypoda-13E, 17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P) or any combination thereof.

In some embodiments, the composition includes at least one triterpenoic acid and at least one neutral triterpenoid. In some embodiments, the at least one triterpenoic acid may include masticadienonic acid (MDA), isomasticadienonic acid (IMDA), masticadienolic acid (MLA), isomasticadienolic acid (IMLA), 3-O-acetyl masticadienolic acid, 3-O-acetyl epimasticadienolic acid, 3-O-acetyl isomasticadienolic acid, 3-O-acetyl epi-isomasticadienolic acid, oleanonic acid (OA), moronic acid (MA), or any combination thereof. In some embodiments, the neutral triterpenoid may include 8-dihydroxypolypoda-13E, 17E,21-triene (NF-1), (8R)-3-Oxo-8-hydroxypolypoda-13E, 17E,21-triene (NF-2), Oleanonic aldehyde (NF-3), Tirucallol (NF-4), 28-hydroxylup-20(29)-en-3-one (NF-A), 28-hydroxy-beta-amyrone (NF-B) or any combination thereof.

In some embodiments, the at least one triterpenoic acid is or consists of masticadienonic acid (MDA). In some embodiments, the at least one triterpenoic acid is or consists of isomasticadienonic acid (IMDA). In some embodiments, the at least one triterpenoic acid may consist of masticadienonic acid (MDA) and isomasticadienonic acid (IMDA). In some embodiments, the triterpenoic acid may include at least masticadienonic acid (MDA) and isomasticadienonic acid (IMDA). In some embodiments, the triterpenoic acid may include at least masticadienonic acid (MDA), isomasticadienonic acid (IMDA), masticadienolic acid (MLA) and isomasticadienolic acid (IMLA).

In some embodiments, the at least one neutral triterpenoid is or consists of NF-1. In some embodiments, the at least one neutral triterpenoid is or consists of NF-2. In some embodiments, the at least one neutral triterpenoid may consist of NF-1 and NF-2. In some embodiments, the at least one neutral triterpenoid may include at least NF-1 and NF-2. In some embodiments, the at least one neutral triterpenoid may include at least NF-1, NF-2, NF-3 and NF-4. In some embodiments, the at least one neutral triterpenoid may include at least NF-1, NF-2, NF-3, NF-4, NF-A and NF-B. In some embodiments, the at least one neutral triterpenoid may include at least NF-1, NF-2, NF-3, NF-4, NF-A, NF-B and NF-P.

In some embodiments, the triterpenoic acid may include at least masticadienonic acid (MDA) and isomasticadienonic acid (IMDA). In some embodiments, the triterpenoic acid may include at least masticadienonic acid (MDA), isomasticadienonic acid (IMDA), masticadienolic acid (MLA) and isomasticadienolic acid (IMLA). In some embodiments, the triterpenoic acid may include at least masticadienonic acid (MDA), isomasticadienonic acid (IMDA), 3-O-acetyl masticadienolic acid (3-OAc-MLA) and 3-O-acetyl isomasticadienolic acid (3-OAc-IMLA). In some embodiments, the triterpenoic acid may include at least masticadienonic acid (MDA), isomasticadienonic acid (IMDA), 3-O-acetyl epimasticadienolic acid (3-OAc-epi-MLA) and 3-O-acetyl epiisomasticadienolic acid (3-OAc-epi-IMLA). In some embodiments, the triterpenoic acid may include at least masticadienonic acid (MDA), isomasticadienonic acid (IMDA), 3-O-acetyl masticadienolic acid (3-OAc-MLA), 3-O-acetyl isomasticadienolic acid (3-OAc-IMLA), 3-O-acetyl epimasticadienolic acid (3-OAc-epi-MLA) and 3-O-acetyl epiisomasticadienolic acid (3-OAc-epi-IMLA). In some embodiments, neutral triterpenoid may include at least NF-1 and NF-2. In some embodiments, the neutral triterpenoid may include at least NF-1, NF-2, NF-3 and NF-4. In some embodiments, the neutral triterpenoid may include at least NF-1, NF-2, NF-3, NF-4, NF-A and NF-B. In some embodiments, the neutral triterpenoid may include at least NF-1, NF-2 and NF-4. In some embodiments, the neutral triterpenoid may include at least NF-2, NF-3 and NF-4. In some embodiments, the neutral triterpenoid may include at least NF-1, NF-2 and NF-3. In some embodiments, the neutral triterpenoid may include at least NF-1, NF-3 and NF-4. In some embodiments, the neutral triterpenoid may include at least NF-1 and NF-3. In some embodiments, the neutral triterpenoid may include at least NF-1 and NF-4. In some embodiments, the neutral triterpenoid may include at least NF-2 and NF-3. In some embodiments, the neutral triterpenoid may include at least NF-2 and NF-4. In some embodiments, the neutral triterpenoid may include at least NF-1, NF-2, NF-A and NF-B. In some embodiments, the neutral triterpenoid may include at least NF-1, NF-A and NF-B. In some embodiments, the neutral triterpenoid may include at least NF-2, NF-A and NF-B. In some embodiments, the neutral triterpenoid may include at least NF-1 and NF-A. In some embodiments, the neutral triterpenoid may include at least NF-2 and NF-A. In some embodiments, the neutral triterpenoid may include at least NF-1 and NF-B. In some embodiments, the neutral triterpenoid may include at least NF-2 and NF-B. In some embodiments, the neutral triterpenoid may include at least NF-1, NF-2 and NF-A. In some embodiments, the neutral triterpenoid may include at least NF-1, NF-2 and NF-B.

In some embodiments, the neutral triterpenoids consist essentially of not more than seven neutral triterpenoids. In some embodiments, the neutral triterpenoids consist essentially of not more than six neutral triterpenoids. In some embodiments, the neutral triterpenoids consist essentially of not more than five neutral triterpenoids. In some embodiments, the neutral triterpenoids consist essentially of not more than four neutral triterpenoids.

In some embodiments, the additional neutral triterpenoids consist essentially of not more than six neutral triterpenoids. In some embodiments, the additional neutral triterpenoids consist essentially of not more than five neutral triterpenoids. In some embodiments, the additional neutral triterpenoids consist essentially of not more than four neutral triterpenoids.

In some embodiments, the additional neutral triterpenoids consist essentially of not more than three neutral triterpenoids. In some embodiments, the additional neutral triterpenoids consist essentially of not more than two neutral triterpenoids.

In some embodiments, the triterpenoic acids consists essentially of not more than eight triterpenoic acids. In some embodiments, the triterpenoic acids consists essentially of not more than seven triterpenoic acids. In some embodiments, the triterpenoic acids consists essentially of not more than six triterpenoic acids. In some embodiments, the triterpenoic acids consists essentially of not more than five triterpenoic acids. In some embodiments, the triterpenoic acids consists essentially of not more than four triterpenoic acids. In some embodiments, the triterpenoic acids consists essentially of not more than three triterpenoids. In some embodiments, the triterpenoic acids consists essentially of not more than two triterpenoic acids.

In some embodiments, the composition consists essentially of not more than 15 triterpenoids. In some embodiments, the composition consists essentially of not more than 14 triterpenoids. In some embodiments, the composition consists essentially of not more than 13 triterpenoids. In some embodiments, the composition consists essentially of not more than 12 triterpenoids. In some embodiments, the composition consists essentially of not more than 11 triterpenoids. In some embodiments, the composition consists essentially of not more than 10 triterpenoids. In some embodiments, the composition consists essentially of not more than 9 triterpenoids. In some embodiments, the composition consists essentially of not more than 8 triterpenoids. In some embodiments, the composition consists essentially of not more than 7 triterpenoids. In some embodiments, the composition consists essentially of not more than 6 triterpenoids.

The compositions disclosed herein unexpectedly exhibit a synergistic effect, whereby the combination of compounds exhibit a markedly improved therapeutic effect in the treatment of Alzheimer's disease (AD), Parkinson's Diseases (PD) and/or vascular dementia (VD). Such combinations of compounds further exhibit an unexpected synergistic effect in the treatment of Multiple System Atrophy (MSA) and Progressive Supranuclear Palsy (PSP) and tauopathic diseases and conditions.

In some embodiments, the composition comprises at least two triterpenoic acids selected from MDA, IMDA, MLA, IMLA, OA, MA, 3-O-acetyl masticadienolic acid, 3-O-acetyl epimasticadienolic acid, 3-O-acetyl isomasticadienolic acid and 3-O-acetyl epi-isomasticadienolic acid. In some embodiments, the composition comprises at least two triterpenoic acids selected from MDA, IMDA, MLA, IMLA, OA, MA, 3-O-acetyl masticadienolic acid and 3-O-acetyl isomasticadienolic acid. In some embodiments, the composition comprises at least two triterpenoic acids selected from MDA, IMDA, MLA and IMLA. In some embodiments, the composition comprises at least two triterpenoic acids selected from MDA, IMDA, and MLA. In some embodiments, the composition comprises at least two triterpenoic acids selected from MDA, IMDA and IMLA. In some embodiments, the composition comprises at least MDA and IMDA.

In some embodiments, the composition comprises at least three triterpenoic acids selected from MDA, IMDA, MLA, IMLA, OA, MA, 3-O-acetyl masticadienolic acid, 3-O-acetyl epimasticadienolic acid, 3-O-acetyl isomasticadienolic acid and 3-O-acetyl epi-isomasticadienolic acid. In some embodiments, the composition comprises at least three triterpenoic acids selected from MDA, IMDA, MLA, IMLA, OA, MA, 3-O-acetyl masticadienolic acid and 3-O-acetyl isomasticadienolic acid. In some embodiments, the composition comprises at least three triterpenoic acids selected from MDA, IMDA, MLA and IMLA. In some embodiments, the composition comprises at least MDA, IMDA, and MLA. In some embodiments, the composition comprises at least MDA, IMDA and IMLA.

In some embodiments, the composition comprises at least four triterpenoic acids selected from MDA, IMDA, MLA, IMLA, OA, MA, 3-O-acetyl masticadienolic acid, 3-O-acetyl epimasticadienolic acid, 3-O-acetyl isomasticadienolic acid and 3-O-acetyl epi-isomasticadienolic acid. In some embodiments, the composition comprises at least four triterpenoic acids selected from MDA, IMDA, MLA, IMLA, OA, MA, 3-O-acetyl masticadienolic acid and 3-O-acetyl isomasticadienolic acid. In some embodiments, the composition comprises at least MDA, IMDA, MLA and IMLA.

In some embodiments, the composition comprises at least two neutral triterpenoids selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. In some embodiments, the composition comprises at least two neutral triterpenoids selected from NF-1, NF-2, NF-3, NF-4, NF-A, NF-B, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least two neutral triterpenoids selected from NF-1, NF-2, NF-3, NF-4, NF-A, NF-B and NF-P. In some embodiments, the composition comprises at least two neutral triterpenoids selected from NF-1, NF-2, NF-3, NF-4, NF-A and NF-B. In some embodiments, the composition comprises at least two neutral triterpenoids selected from NF-1, NF-2, NF-3 and NF-4. In some embodiments, the composition comprises at least two neutral triterpenoids selected from NF-1, NF-2 and NF-3. In some embodiments, the composition comprises at least two neutral triterpenoids selected from NF-1, NF-2 and NF-4. In some embodiments, the composition comprises at least NF-1 and NF-2.

In some embodiments, the composition comprises at least three neutral triterpenoids selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. In some embodiments, the composition comprises at least three neutral triterpenoids selected from NF-1, NF-2, NF-3, NF-4, NF-A, NF-B, 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least three neutral triterpenoids selected from NF-1, NF-2, NF-3, NF-4, NF-A, NF-B and NF-P. In some embodiments, the composition comprises at least three neutral triterpenoids selected from NF-1, NF-2, NF-3, NF-4, NF-A and NF-B. In some embodiments, the composition comprises at least three neutral triterpenoids selected from NF-1, NF-2, NF-3 and NF-4. In some embodiments, the composition comprises at least NF-1, NF-2 and NF-3. In some embodiments, the composition comprises at least NF-1, NF-2 and NF-4. In some embodiments, the composition comprises at least NF-1, NF-3 and NF-4. In some embodiments, the composition comprises at least NF-3, NF-3 and NF-4.

In some embodiments, the composition comprises at least four neutral triterpenoids selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least four neutral triterpenoids selected from NF-1, NF-2, NF-3, NF-4, NF-A, NF-B, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least four neutral triterpenoids selected from NF-1, NF-2, NF-3, NF-4, NF-A and NF-B. In some embodiments, the composition comprises at least four neutral triterpenoids selected from NF-1, NF-2, NF-3, NF-4, NF-A, NF-B and NF-P. In some embodiments, the composition comprises at least NF-1, NF-2, NF-3 and NF-4.

In some embodiments, combinations of triterpenoic acids and neutral triterpenoids may be substantially devoid of essential oils.

In some embodiments, the triterpenoic acids may comprise from about 1% to about 80% of the total active ingredients of the composition. In some embodiments, the triterpenoic acids may comprise from about 10% to about 80% of the total active ingredients of the composition. In some embodiments, the triterpenoic acids may comprise from about 20% to about 80% of the total active ingredients of the composition. In some embodiments, the triterpenoic acids may comprise from about 30% to about 70% of the total active ingredients of the composition. In some embodiments, the triterpenoic acids may comprise from about 35% to about 65% of the total active ingredients of the composition. In some embodiments, the triterpenoic acids may comprise from about 40% to about 60% of the total active ingredients of the composition.

In some embodiments, the triterpenoic acids may comprise from about 0.01% to about 80% of the total composition. In some embodiments, the triterpenoic acids may comprise from about 0.01% to about 50% of the total composition. In some embodiments, the triterpenoic acids may comprise from about 0.01% to about 10% of the total composition. In some embodiments, the triterpenoic acids may comprise from about 0.1% to about 10% of the total composition. In some embodiments, the triterpenoic acids may comprise from about 0.5% to about 4% of the total composition. In some embodiments, the triterpenoic acids may comprise from about 0.1% to about 0.5% of the total composition. In some embodiments, the triterpenoic acids may comprise from about 0.1% to about 1.0% of the total composition. In some embodiments, the triterpenoic acids may comprise from about 0.1% to about 2% of the total composition. In some embodiments, the triterpenoic acids may comprise from about 1% to about 3.5% of the total composition. In some embodiments, the triterpenoic acids may comprise from about 1.5% to about 3% of the total composition. In some embodiments, the triterpenoic acids may comprise from about 1.75% to about 2.75% of the total composition. In some embodiments, the triterpenoic acids may comprise from about 2% to about 2.5% of the total composition.

In some embodiments, the neutral triterpenoids may comprise from about 1% to about 80% of the total active ingredients of the composition. In some embodiments, the neutral triterpenoids may comprise from about 10% to about 80% of the total active ingredients of the composition. In some embodiments, the neutral triterpenoids may comprise from about 20% to about 80% of the total active ingredients of the composition. In some embodiments, the neutral triterpenoids may comprise from about 30% to about 70% of the total active ingredients of the composition. In some embodiments, the neutral triterpenoids may comprise from about 35% to about 65% of the total active ingredients of the composition. In some embodiments, the neutral triterpenoids may comprise from about 40% to about 60% of the total active ingredients of the composition.

In some embodiments, the neutral triterpenoids may comprise from about 0.01% to about 80% of the total composition. In some embodiments, the neutral triterpenoids may comprise from about 0.01% to about 50% of the total composition. In some embodiments, the neutral triterpenoids may comprise from about 0.01% to about 10% of the total composition. In some embodiments, the neutral triterpenoids may comprise from about 0.1% to about 10% of the total composition. In some embodiments, the neutral triterpenoids may comprise from about 0.5% to about 4% of the total composition. In some embodiments, the neutral triterpenoid may comprise from about 0.1% to about 0.5% of the total composition. In some embodiments, the neutral triterpenoid may comprise from about 0.1% to about 1.0% of the total composition. In some embodiments, the neutral triterpenoid may comprise from about 0.1% to about 2% of the total composition. In some embodiments, the neutral triterpenoids may comprise from about 1% to about 3.5% of the total composition. In some embodiments, the neutral triterpenoids may comprise from about 1.5% to about 3% of the total composition. In some embodiments, the neutral triterpenoids may comprise from about 1.75% to about 2.75% of the total composition. In some embodiments, the neutral triterpenoids may comprise from about 2% to about 2.5% of the total composition.

In some embodiments, the composition for use in the invention comprises a therapeutically effective amount of at least one triterpenoic acid and of at least one neutral triterpenoid as described herein, and a pharmaceutically acceptable carrier. In some embodiments, the carrier is hydrophobic.

In some embodiments, the pharmaceutically acceptable carrier may include a hydrophobic carrier. In some embodiments, the hydrophobic carrier may include at least one oil. In some embodiments, the oil may be selected from the group consisting of a mineral oil, a vegetable oil and combinations thereof. In some embodiments, the vegetable oil may be selected from the group consisting of cottonseed oil, olive oil, almond oil, canola oil, coconut oil, corn oil, grape seed oil, peanut oil, saffron oil, sesame oil, soybean oil, and combinations thereof. In some embodiments, the vegetable oil is a commercially available product which may be obtained either as a 'NF' (National Formulary) grade product or as a 'USP' (US Pharmacopoeia) grade product. In some embodiments, the mineral oil may be light mineral oil. In some embodiments, the hydrophobic carrier may include at least one wax. In some embodiments, the hydrophobic carrier may include a combination of at least one oil and at least one wax.

The term "mineral oil" refers to a clear colorless nearly odorless and tasteless liquid obtained from the distillation of petroleum. It may also be referred to as white oil, white mineral oil, liquid petrolatum, liquid paraffin or white paraffin oil. In some embodiments, the mineral oil is light mineral oil, a commercially available product which may be obtained either as a 'NF' (National Formulary) grade product or as a 'USP' (US Pharmacopoeia) grade product. For use in the invention, the mineral oil is preferably free of aromatics and other unsaturated compounds.

The pharmaceutically acceptable carrier may alternately or in addition comprise an oil replacement. Oil replacements include alkanes having at least 10 carbon atoms (e.g., isohexadecane), benzoate esters, aliphatic esters, noncomodogenic esters, volatile silicone compounds (e.g., cyclomethicone), and volatile silicone substitutes. Examples of benzoate esters include $C_{12}$-$C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}$-$C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate.

Cyclomethicone is an evaporative silicone which may be included in the carrier to assist in making the composition amenable to ejection from a spray dispenser.

The hydrophobic carrier may further comprise at least one wax. Waxes include for example, beeswax; vegetable waxes, sugar cane waxes, mineral waxes, and synthetic waxes. Vegetable waxes include for example, carnauba, candelilla, ouricury and jojoba wax. Mineral waxes include for example, paraffin wax, lignite wax, microcrystalline waxes and ozokerites. Synthetic waxes include for example, polyethylene waxes.

Various formulations of the different combinations of triterpenoic acids and neutral triterpenoids and preparation thereof are disclosed herein. The pharmaceutical compositions of the invention may be administered by any means that achieve their intended purpose. For example, administration may be by, for example, oral, parenteral, topical, transdermal routes, such as, for example, subcutaneous, intravenous, intramuscular, intradermal, intraperitoneal, intraarterial, intrauterine, intraurethral, intracardial, intracerebral, intracerebroventricular, intrarenal, intrahepatic, intratendon, intraosseus, intrathecal, dermal, vaginal, rectal, inhalation, intranasal, ocular, auricular and buccal administration routes.

The administering may in addition comprise a technique or means such as electroporation, or sonication in order to assist in their delivery, for example transdermally. Other techniques which may be employed include for example, radio frequency or pressurized spray application.

The dosage administered may be dependent upon the age, health, and weight of the subject, the use of concurrent treatment, if any, frequency of treatment, and the nature of the effect desired. The amount triterpenoids of the present invention in any unit dosage form comprises a therapeutically effective amount which may vary depending on the recipient subject, route and frequency of administration.

In some embodiments, when MA is one of the ingredients in the composition, the amount of the MA of the total composition may be in the range of about 0% to about 15%. In some embodiments, the amount of the MA of the total composition may be in the range of about 0% to about 7.5%. In some embodiments, the amount of the MA of the total composition may be in the range of about 0% to about 2.5%. In some embodiments, the amount of the MA of the total composition may be in the range of about 0% to about 1%. In some embodiments, the amount of the MA of the total composition may be in the range of about 0% to about 0.3%. In some embodiments, the amount of the MA of the total composition may about 0.3%. In some embodiments, the amount of MA with respect to the total amount of triterpenoids may be in the range of about 0% to about 50%. In some embodiments, the amount of MA with respect to the total amount of triterpenoids may be in the range of about 0% to about 25%. In some embodiments, the amount of MA with respect to the total amount of triterpenoids may be in the range of about 0% to about 8%. In some embodiments, the amount of MA with respect to the total amount of triterpenoids may be in the range of about 6% to about 8%.

In some embodiments, when OA is one of the ingredients in the composition the amount of the OA of the total composition may be in the range of about 0% to about 25%. In some embodiments, the amount of the OA of the total composition may be in the range of about 0% to about 10%. In some embodiments, the amount of the OA of the total composition may be in the range of about 0% to about 5%. In some embodiments, the amount of the OA of the total composition may be in the range of about 0% to about 1%. In some embodiments, the amount of the OA of the total composition may be in the range of about 0% to about 0.5%. In some embodiments, the amount of the OA of the total composition may about 0.5%. In some embodiments, the amount of OA with respect to the total amount of triterpenoids may be in the range of about 0% to about 50%. In some embodiments, the amount of OA with respect to the total amount of triterpenoids may be in the range of about 0% to about 25%. In some embodiments, the amount of OA with respect to the total amount of triterpenoids may be in the range of about 0% to about 11%. In some embodiments, the amount of OA with respect to the total amount of triterpenoids may be in the range of about 9% to about 11%.

In some embodiments, when MDA is one of the ingredients in the composition the amount of the MDA of the total composition may be in the range of about 0% to about 25%. In some embodiments, the amount of the MDA of the total composition may be in the range of about 0% to about 10%. In some embodiments, the amount of the MDA of the total composition may be in the range of about 0% to about 5%. In some embodiments, the amount of the MDA of the total composition may be in the range of about 0% to about 2.5%. In some embodiments, the amount of the MDA of the total composition may be in the range of about 0.5% to about 1%. In some embodiments, the amount of MDA with respect to the total amount of triterpenoids may be in the range of about 0% to about 50%. In some embodiments, the amount of MDA with respect to the total amount of triterpenoids may be in the range of about 5% to about 35%. In some embodiments, the amount of MDA with respect to the total amount of triterpenoids may be in the range of about 10% to about 26%. In some embodiments, the amount of MDA with respect to the total amount of triterpenoids may be in the range of about 20% to about 26%.

In some embodiments, when IMDA is one of the ingredients in the composition, the amount of the IMDA of the total composition may be in the range of about 0% to about 25%. In some embodiments, the amount of the IMDA of the total composition may be in the range of about 0% to about 10%. In some embodiments, the amount of the IMDA of the total composition may be in the range of about 0% to about 5%. In some embodiments, the amount of the IMDA of the total composition may be in the range of about 0% to about 2.5%. In some embodiments, the amount of the IMDA of the total composition may be in the range of about 0.6% to about 1%. In some embodiments, the amount of IMDA with respect to the total amount of triterpenoids may be in the range of about 0% to about 50%. In some embodiments, the amount of IMDA with respect to the total amount of triterpenoids may be in the range of about 5% to about 35%. In some embodiments, the amount of IMDA with respect to the total amount of triterpenoids may be in the range of about 12% to about 26%. In some embodiments, the amount of IMDA with respect to the total amount of triterpenoids may be in the range of about 20% to about 26%.

In some embodiments, when MLA is one of the ingredients in the composition, the amount of the MLA of the total composition may be in the range of about 0% to about 10%. In some embodiments, the amount of the MLA of the total composition may be in the range of about 0% to about 3%. In some embodiments, the amount of the MLA of the total composition may be in the range of about 0% to about 1%. In some embodiments, the amount of the MLA of the total composition may be in the range of about 0% to about 0.5%. In some embodiments, the amount of the MLA of the total composition may be in the range of about 0% to about 0.2%. In some embodiments, the amount of the MLA of the total composition may about 0.2%. In some embodiments, the amount of MLA with respect to the total amount of triterpenoids may be in the range of about 0% to about 25%. In some embodiments, the amount of MLA with respect to the total amount of triterpenoids may be in the range of about 0% to about 15%. In some embodiments, the amount of MLA with respect to the total amount of triterpenoids may be in the range of about 0% to about 4%. In some embodiments, the amount of MLA with respect to the total amount of triterpenoids may about 4%.

In some embodiments, when IMLA is one of the ingredients in the composition, the amount of the IMLA of the total composition may be in the range of about 0% to about 10%. In some embodiments, the amount of the IMLA of the total composition may be in the range of about 0% to about 3%. In some embodiments, the amount of the IMLA of the total composition may be in the range of about 0% to about 1%. In some embodiments, the amount of the IMLA of the total composition may be in the range of about 0% to about 0.5%. In some embodiments, the amount of the IMLA of the total composition may be in the range of about 0% to about 0.2%. In some embodiments, the amount of the IMLA of the total composition may about 0.2%. In some embodiments, the amount of IMLA with respect to the total amount of triterpenoids may be in the range of about 0% to about 25%. In some embodiments, the amount of IMLA with respect to the total amount of triterpenoids may be in the range of about 0% to about 15%. In some embodiments, the amount of IMLA with respect to the total amount of triterpenoids may be in the range of about 0% to about 4%. In some embodiments, the amount of IMLA with respect to the total amount of triterpenoids may about 4%.

In some embodiments, when 3-OAc-MLA is one of the ingredients in the composition, the amount of the 3-OAc-MLA of the total composition may be in the range of about 0% to about 15%. In some embodiments, the amount of the 3-OAc-MLA of the total composition may be in the range of about 0% to about 5%. In some embodiments, the amount of the 3-OAc-MLA of the total composition may be in the range of about 0% to about 3%. In some embodiments, the amount of the 3-OAc-MLA of the total composition may be in the range of about 0% to about 1%. In some embodiments, the amount of the 3-OAc-MLA of the total composition may be in the range of about 0% to about 0.2%. In some embodiments, the amount of the 3-OAc-MLA of the total composition may about 0.2%. In some embodiments, the amount of the 3-OAc-MLA with respect to the total amount of triterpenoids may be in the range of about 0% to about 25%. In some embodiments, the amount of the 3-OAc-MLA with respect to the total amount of triterpenoids may be in the range of about 0% to about 15%. In some embodiments, the amount of the 3-OAc-MLA with respect to the total amount of triterpenoids may be in the range of about 0% to about 10%. In some embodiments, the amount of the 3-OAc-MLA with respect to the total amount of triterpenoids may be in the range of about 0% to about 5%. In some embodiments, the amount of the 3-OAc-MLA with respect to the total amount of triterpenoids may about 3%.

In some embodiments, when 3-OAc-IMLA is one of the ingredients in the composition, the amount of the 3-OAc-IMLA of the total composition may be in the range of about 0% to about 15%. In some embodiments, the amount of the 3-OAc-IMLA of the total composition may be in the range of about 0% to about 5%. In some embodiments, the amount of the 3-OAc-IMLA of the total composition may be in the range of about 0% to about 3%. In some embodiments, the amount of the 3-OAc-IMLA of the total composition may be in the range of about 0% to about 1%. In some embodiments, the amount of the 3-OAc-IMLA of the total composition may be in the range of about 0% to about 0.2%. In some embodiments, the amount of the 3-OAc-IMLA of the total composition may about 0.2%. In some embodiments, the amount of the 3-OAc-IMLA with respect to the total amount of triterpenoids may be in the range of about 0% to about 25%. In some embodiments, the amount of the 3-OAc-IMLA with respect to the total amount of triterpenoids may be in the range of about 0% to about 15%. In some embodiments, the amount of the 3-OAc-IMLA with respect to the total amount of triterpenoids may be in the range of about 0% to about 10%. In some embodiments, the amount of the 3-OAc-IMLA with respect to the total amount of triterpenoids may be in the range of about 0% to about 5%. In some embodiments, the amount of the 3-OAc-IMLA with respect to the total amount of triterpenoids may about 3%.

In some embodiments, when 3-OAc-epi-MLA is one of the ingredients in the composition, the amount of the 3-OAc-epi-MLA of the total composition may be in the range of about 0% to about 15%. In some embodiments, the amount of the 3-OAc-epi-MLA A of the total composition may be in the range of about 0% to about 5%. In some embodiments, the amount of the 3-OAc-epi-MLA of the total composition may be in the range of about 0% to about 3%. In some embodiments, the amount of the 3-OAc-epi-MLA of the total composition may be in the range of about 0% to about 1%. In some embodiments, the amount of the 3-OAc-epi-MLA of the total composition may be in the range of about 0% to about 0.2%. In some embodiments, the amount of the 3-OAc-epi-MLA of the total composition may about 0.2%. In some embodiments, the amount of the 3-OAc-epi-MLA with respect to the total amount of triterpenoids may be in the range of about 0% to about 25%. In some embodiments, the amount of the 3-OAc-epi-MLA with respect to the total amount of triterpenoids may be in the range of about 0% to about 15%. In some embodiments, the amount of the 3-OAc-epi-MLA with respect to the total amount of triterpenoids may be in the range of about 0% to about 10%. In some embodiments, the amount of the 3-OAc-epi-MLA with respect to the total amount of triterpenoids may be in the range of about 0% to about 5%. In some embodiments, the amount of the 3-OAc-epi-MLA with respect to the total amount of triterpenoids may about 3%.

In some embodiments, when 3-OAc-epi-IMLA is one of the ingredients in the composition, the amount of the 3-OAc-epi-IMLA of the total composition may be in the range of about 0% to about 15%. In some embodiments, the amount of the 3-OAc-epi-IMLA of the total composition may be in the range of about 0% to about 5%. In some embodiments, the amount of the 3-OAc-epi-IMLA of the total composition may be in the range of about 0% to about 3%. In some embodiments, the amount of the 3-OAc-epi-IMLA of the total composition may be in the range of about 0% to about 1%. In some embodiments, the amount of the 3-OAc-epi-IMLA of the total composition may be in the range of about 0% to about 0.2%. In some embodiments, the amount of the 3-OAc-epi-IMLA of the total composition may about 0.2%. In some embodiments, the amount of the 3-OAc-epi-IMLA with respect to the total amount of triterpenoids may be in the range of about 0% to about 25%. In some embodiments, the amount of the 3-OAc-epi-IMLA with respect to the total amount of triterpenoids may be in the range of about 0% to about 15%. In some embodiments, the amount of the 3-OAc-epi-IMLA with respect to the total amount of triterpenoids may be in the range of about 0% to about 10%. In some embodiments, the amount of the 3-OAc-epi-IMLA with respect to the total amount of triterpenoids may be in the range of about 0% to about 5%. In some embodiments, the amount of the 3-OAc-epi-IMLA with respect to the total amount of triterpenoids may about 3%.

In some embodiments, the amount of the masticadienonic acid (MDA) may be in the range of about 0.05% to about 20%. In some embodiments, the amount of the isomasticadienonic acid (IMDA) may be in the range of about 0.05% to about 20%. In some embodiments, the amount of the oleanonic acid (OA) may be in the range of about 0.05% to about 20%. In some embodiments, the amount of the masticadienonic acid (MDA) may be in the range of about 0.1% to about 10%. In some embodiments, the amount of the isomasticadienonic acid (IMDA) may be in the range of about 0.1% to about 10%. In some embodiments, the amount of the oleanonic acid (OA) may be in the range of about 0.1% to about 10%. In some embodiments, the amount of the masticadienonic acid (MDA) may be in the range of about 0.5% to about 12%. In some embodiments, the amount of the isomasticadienonic acid (IMDA) may be in the range of about 0.5% to about 12%. In some embodiments, the amount of the oleanonic acid (OA) may be in the range of about 0.5% to about 12%. In some embodiments, the amount of the masticadienonic acid (MDA) may be in the range of about 0.5% to about 15%. In some embodiments, the amount of the isomasticadienonic acid (IMDA) may be in the range of about 0.5% to about 15%. In some embodiments, the amount of the oleanonic acid (OA) may be in the range of about 0.5% to about 15%.

In some embodiments, when NF-1 is one of the ingredients in the composition, the amount of the NF-1 of the total composition may be in the range of about 0% to about 25%. In some embodiments, the amount of the NF-1 of the total composition may be in the range of about 0% to about 10%. In some embodiments, the amount of the NF-1 of the total composition may be in the range of about 0% to about 5%. In some embodiments, the amount of the NF-1 of the total composition may be in the range of about 0% to about 1%. In some embodiments, the amount of the NF-1 of the total composition may about 0.5%. In some embodiments, the amount of NF-1 with respect to the total amount of triterpenoids may be in the range of about 0% to about 50%. In some embodiments, the amount of NF-1 with respect to the total amount of triterpenoids may be in the range of about 5% to about 25%. In some embodiments, the amount of NF-1 with respect to the total amount of triterpenoids may be in the range of about 9% to about 13%.

In some embodiments, when NF-2 is one of the ingredients in the composition, the amount of the NF-2 of the total composition may be in the range of about 0% to about 25%. In some embodiments, the amount of the NF-2 of the total composition may be in the range of about 0% to about 10%. In some embodiments, the amount of the NF-2 of the total composition may be in the range of about 0% to about 5%. In some embodiments, the amount of the NF-2 of the total composition may be in the range of about 0% to about 1%. In some embodiments, the amount of the NF-2 of the total composition may about 0.5%. In some embodiments, the amount of NF-2 with respect to the total amount of triterpenoids may be in the range of about 0% to about 50%. In some embodiments, the amount of NF-2 with respect to the total amount of triterpenoids may be in the range of about 5% to about 25%. In some embodiments, the amount of NF-2 with respect to the total amount of triterpenoids may be in the range of about 9% to about 13%.

In some embodiments, when NF-3 is one of the ingredients in the composition, the amount of the NF-3 of the total composition may be in the range of about 0% to about 25%. In some embodiments, the amount of the NF-3 of the total composition may be in the range of about 0% to about 10%. In some embodiments, the amount of the NF-3 of the total composition may be in the range of about 0% to about 5%. In some embodiments, the amount of the NF-3 of the total composition may be in the range of about 0% to about 1%. In some embodiments, the amount of the NF-3 of the total composition may about 0.5%. In some embodiments, the amount of NF-3 with respect to the total amount of triterpenoids may be in the range of about 0% to about 50%. In some embodiments, the amount of NF-3 with respect to the total amount of triterpenoids may be in the range of about 5% to about 25%. In some embodiments, the amount of the NF-3 with respect to the total amount of triterpenoids may be in the range of about 9% to about 13%. In some embodiments, the amount of NF-3 with respect to the total amount of triterpenoids may be in the range of about 10-12%.

In some embodiments, when NF-4 is one of the ingredients in the composition, the amount of the NF-4 of the total composition may be in the range of about 0% to about 25%. In some embodiments, the amount of the NF-4 of the total composition may be in the range of about 0% to about 10%. In some embodiments, the amount of the NF-4 of the total composition may be in the range of about 0% to about 5%. In some embodiments, the amount of the NF-4 of the total composition may be in the range of about 0% to about 1%. In some embodiments, the amount of the NF-4 of the total composition may about 0.33%. In some embodiments, the amount of NF-4 with respect to the total amount of triterpenoids may be in the range of about 0% to about 50%. In some embodiments, the amount of NF-4 with respect to the total amount of triterpenoids may be in the range of about 2.5% to about 25%. In some embodiments, the amount of NF-4 with respect to the total amount of triterpenoids may be in the range of about 6% to about 9%.

In some embodiments, when NF-P is one of the ingredients in the composition, the amount of the NF-P of the total composition may be in the range of about 0% to about 15%. In some embodiments, the amount of the NF-P of the total composition may be in the range of about 0% to about 7.5%. In some embodiments, the amount of the NF-P of the total composition may be in the range of about 0% to about 2.5%. In some embodiments, the amount of the NF-P of the total composition may be in the range of about 0% to about 1%. In some embodiments, the amount of the NF-P of the total composition may be in the range of about 0% to about 0.33%. In some embodiments, the amount of the NF-P of the total composition may about 0.33%. In some embodiments, the amount of NF-P with respect to the total amount of triterpenoids may be in the range of about 0% to about 50%. In some embodiments, the amount of NF-P with respect to the total amount of triterpenoids may be in the range of about 0% to about 25%. In some embodiments, the amount of NF-P with respect to the total amount of triterpenoids may be in the range of about 0% to about 7%. In some embodiments, the amount of NF-P with respect to the total amount of triterpenoids may be in the range of about 6% to about 7%.

In some embodiments, when NF-A is one of the ingredients in the composition, the amount of the NF-A of the total composition may be in the range of about 0% to about 10%. In some embodiments, the amount of the NF-A of the total composition may be in the range of about 0% to about 3%. In some embodiments, the amount of the NF-A of the total composition may be in the range of about 0% to about 1%. In some embodiments, the amount of the NF-A of the total composition may be in the range of about 0% to about 0.5%. In some embodiments, the amount of the NF-A of the total composition may be in the range of about 0% to about 0.25%. In some embodiments, the amount of the NF-A of the total composition may about 0.25%. In some embodiments, the amount of NF-A with respect to the total amount of triterpenoids may be in the range of about 0% to about 25%. In some embodiments, the amount of NF-A with respect to the total amount of triterpenoids may be in the range of about 0% to about 15%. In some embodiments, the amount of NF-A with respect to the total amount of triterpenoids may be in the range of about 0% to about 6%. In some embodiments, the amount of NF-A with respect to the total amount of triterpenoids may be in the range of about 4% to about 6%.

In some embodiments, when NF-B is one of the ingredients in the composition, the amount of the NF-B of the total composition may be in the range of about 0% to about 10%. In some embodiments, the amount of the NF-B of the total composition may be in the range of about 0% to about 3%. In some embodiments, the amount of the NF-B of the total composition may be in the range of about 0% to about 1%. In some embodiments, the amount of the NF-B of the total composition may be in the range of about 0% to about 0.5%. In some embodiments, the amount of the NF-B of the total composition may be in the range of about 0% to about 0.25%. In some embodiments, the amount of the NF-B of the total composition may about 0.25%. In some embodiments, the amount of NF-B with respect to the total amount of triterpenoids may be in the range of about 0% to about 25%. In some embodiments, the amount of NF-B with respect to the total amount of triterpenoids may be in the range of about 0% to about 15%. In some embodiments, the amount of NF-B with respect to the total amount of triterpenoids may be in the range of about 0% to about 6%. In some embodiments, the amount of NF-B with respect to the total amount of triterpenoids may be in the range of about 4% to about 6%.

In some embodiments, the pharmaceutically acceptable carrier may include a hydrophobic carrier. In some embodiments, the hydrophobic carrier may include at least one oil. In some embodiments, the oil may be selected from the group consisting of a mineral oil, a vegetable oil and combinations thereof. In some embodiments, the vegetable oil may be selected from the group consisting of cottonseed oil, olive oil, almond oil, canola oil, coconut oil, corn oil, grape seed oil, peanut oil, saffron oil, sesame oil, soybean oil, and combinations thereof. In some embodiments, the mineral oil may be light mineral oil. In some embodiments, the hydrophobic carrier may include at least one wax. In some embodiments, the hydrophobic carrier may include a combination of at least one oil and at least one wax.

In some embodiments, the pharmaceutically acceptable carrier may be a phospholipid.

In some embodiments, the composition is a pharmaceutical composition. In some embodiments, the composition may be in a form suitable for administration by a route selected from the group consisting of parenteral, transdermal, oral and topical.

In some embodiments, the composition may be in a form suitable for topical administration. In some embodiments, the composition may be in a form suitable for oral administration. In some embodiments, the composition is in a form suitable for parenteral administration. In some embodiments, the composition may be in a form suitable for administration by injection. In some embodiments, the composition is a parenteral formulation for administration by a route selected from the group consisting of subcutaneous, intravenous, intramuscular, intradermal, intraperitoneal, intraarterial, intracerebral, intracerebroventricular, intraosseus and intrathecal.

In some embodiments, the composition may be a parenteral formulation for administration by subcutaneous route.

In some embodiments, the composition may be a parenteral formulation for administration by intramuscular route.

In various embodiments, the composition may be formulated for administration by a route selected from the group consisting of dermal, vaginal, rectal, inhalation, intranasal, ocular, auricular and buccal.

In some embodiments, the pharmaceutical composition may be in a form selected from the group consisting of a capsule, a tablet, a liposome, a suppository, a suspension, an ointment, a cream, a lotion, a solution, an emulsion, a film, a cement, a powder, a glue, an aerosol and a spray. In some embodiments, the capsule may be selected from the group consisting of a hard gelatin capsule and a soft gelatin capsule. In some embodiments, the emulsion is a nanoemulsion or a microemulsion.

In some embodiments, the formulation may include at least one of an inclusion complex, a nanoemulsion, a microemulsion, a powder, a lipid raft, a lipid microparticle, a dendrimer and a liposome. In some embodiments, the inclusion complex may include at least one cyclodextrin. In some embodiments, the at least one cyclodextrin may include hydroxypropyl-β-cyclodextrin. In some embodiments, the nanoemulsion may include droplets having average particle size of less than 800 nm. In some embodiments, the droplets may include droplets having average particle size of less than 500 nm. In some embodiments, the droplets may include droplets having average particle size of less than 200 nm. In some embodiments, the powder may include a spray dried powder. In some embodiments, the liposome may include a multilamellar vesicle. In some embodiments, the microemulsion may include a non-ionic surfactant. In some embodiments, the non-ionic surfactant may be selected from the group consisting of a polyoxyl castor oil, a polyoxyethylene sorbitan fatty acid ester (polysorbates), a poloxamer, a vitamin E derivative, a polyoxyethylene alkyl ether, a polyoxyethylene sterate, or saturated polyglycolyzed glyceride or combinations thereof.

In some embodiments, the composition may be disposed on the article of manufacture in the form of a coating. In some embodiments, the article of manufacture may include a vessel, wherein the composition may be disposed within the vessel. In some embodiments, the article of manufacture may be selected from the group consisting of a fabric article, a diaper, a wound dressing, a medical device, a needle or plurality of needles, a microneedle or plurality of microneedles, an injection device and a spray dispenser. In some embodiments, the article of manufacture may include a plurality of microneedles. In some embodiments, the medical device is selected from the group consisting of a prosthetic, an artificial organ or component thereof, a valve, a catheter, a tube, a stent, an artificial membrane, a pacemaker, a sensor, an endoscope, an imaging device, a pump, a wire and an implant. In some embodiments, the implant is selected from the group consisting of a cardiac implant, a cochlear implant, a corneal implant, a cranial implant, a dental implant, a maxillofacial implant, an organ implant, an orthopedic implant, a vascular implant, an intraarticular implant and a breast implant.

In some embodiments, the composition may be suitable for administration by a means selected from the group consisting of electroporation, sonication, radio frequency, pressurized spray and combinations thereof.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes. Pharmaceutical compositions for oral use may be obtained by combining the active compounds with solid and semi-solid excipients and suitable preservatives, and/or antioxidants. Optionally, the resulting mixture may be ground and processed. The resulting mixture of granules may be used, after adding suitable auxiliaries, if necessary, to obtain tablets, softgels, capsules, or dragee cores.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical compositions for oral use include push-fit capsules made of gelatin, as well as soft, sealed capsules made of gelatin and a plasticizer, such as glycerol or sorbitol.

Formulations for parenteral administration include suspensions and microparticle dispersions of the active compounds as appropriate. In some embodiments, oily injection suspensions may be administered. Suitable lipophilic solvents or vehicles include fatty oils, e.g., sesame oil, or synthetic fatty acid esters, e.g., ethyl oleate, triglycerides, polyethylene glycol-400, cremophor, or cyclodextrins. Injection suspensions may contain substances which increase the viscosity of the suspension include, e.g., sodium carboxymethyl cellulose, sorbitol, and/or dextran. Optionally, the suspension may also contain stabilizers.

Pharmaceutical compositions can also be prepared using liposomes comprising the active ingredient. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. In general, the preferred lipids are phospholipids and the phosphatidyl cholines (lecithins), both natural and synthetic. Methods to form liposomes are known in the art, as disclosed for example, in Prescott, Ed., Methods in Cell Biology, Volume XIV, Academic Press, New York, N.Y. (1976) and in U.S. Pat. No. 7,048,943.

Formulations for topical administration include ointments. Suitable carriers include vegetable or mineral oils, white petrolatum, branched chain fats or oils, animal fats and waxes. The preferred carriers are those in which the active ingredient is soluble. Stabilizers, humectants and antioxidants may also be included, as well as agents imparting color or fragrance, if desired. Ointments may be formulated for example, by mixing a solution of the active ingredient in a vegetable oil such as almond oil with warm soft paraffin, and allowing the mixture to cool.

The pharmaceutical composition may comprise an oil-in-water emulsion or microemulsion in order to facilitate its formulation for oral, parenteral or topical use Such emulsions/microemulsions generally include lipids, surfactants, optionally humectants, and water. Suitable lipids include those generally know to be useful for creating oil-in-water emulsions/microemulsions, for example fatty acid glyceride esters. Suitable surfactants include those generally known to be useful for creating oil-in-water emulsions/microemulsions wherein lipids are used as the oil component in the emulsion. Non-ionic surfactants may be preferred, such as for example, ethoxylated castor oil, phospholipids, and block copolymers of ethylene oxide and propylene oxide. Suitable humectants, if used, include for example propylene glycol or polyethylene glycol.

The pharmaceutical composition may be formulated in the form of a gel, such as a hydrogel formed from a gel-forming polymer such as carrageenan, xanthan gum, gum karaya, gum acacia, locust bean gum, guar gum. A hydrogel may be combined with an oil-in-water emulsion comprising the active ingredient.

The pharmaceutical composition may be formulated in the form of a cement such as those comprising polymethylmethacrylate (PMMA) or calcium phosphate. In some embodiments, the pharmaceutical composition may be formulated in the form of a powder.

In some embodiments, the present invention provides therapeutic uses and methods of treating Alzheimer's disease (AD) in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Parkinson's Diseases (PD) in a subject in need thereof comprising administering to a subject a therapeutically effective amount of a composition comprising a combination of at least one triterpenoic acid and at least one neutral triterpenoid. In some embodiments, the present invention provides therapeutic uses and methods of treating vascular dementia (VD) in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Parkinson-plus syndrome in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Parkinsonisms in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Multi System Atrophy (MSA) in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Progressive Supranuclear Palsy (PSP) in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating tauopathic diseases and conditions in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Primary Age-related Tauopathy (PART) in a subject in need thereof, comprising administering to a subject a therapeutically effective amount of a composition comprising a combination of at least one triterpenoic acid and at least one neutral triterpenoid. In some embodiments, the present invention provides therapeutic uses and methods of treating Pick's disease in a subject in need thereof, comprising administering to a subject a therapeutically effective amount of a composition comprising a combination of at least one triterpenoic acid and at least one neutral triterpenoid.

The step of administering the compositions may comprise any acceptable route including oral, topical, parenteral, and transdermal, such as, for example, parenteral administration includes intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus, intrathecal, dermal, vaginal, rectal, inhalation, intranasal, ocular, auricular and buccal routes of administration.

In some embodiments, the method may be carried out prior to or following implantation of a medical device into the subject. In some embodiments, the method may be carried out prior to or following implantation of a medical device into the subject in order to treat the implications/consequences of the condition. Medical devices include, but are not limited to a prosthetic, an artificial organ or component thereof, a valve, a catheter, a tube, a stent, an artificial membrane, a pacemaker, a sensor, an endoscope, an imaging device, a pump, a wire and an implant. Implants include, but are not limited to a cardiac implant, a cochlear implant, a corneal implant, a cranial implant, a dental implant, a maxillofacial implant, an organ implant, an orthopedic implant, a vascular implant, an intraarticular implant and a breast implant.

In some embodiments, the medical device is an organ implant, which may in certain cases comprise autologous cells of the subject.

In some embodiments, the step of contacting comprises a means selected from the group consisting of electroporation, sonication, radio frequency, pressurized spray and combinations thereof.

In some embodiments, the step of contacting comprises establishing contact between interstitial fluid and the composition. Contact between interstitial fluid and the composition may be accomplished by piercing and/or teasing the dermis with a needle, a microneedle, or an apparatus comprising a plurality of needles or microneedles. Such needles or microneedles are preferably non-hollow and may be fashioned in a plurality for example, on a comb or brush-like apparatus.

The method of the invention is suitable for application in humans and non-human mammals.

The method of the invention may encompass use of an article of manufacture which incorporates the composition comprising the combinations described herein.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Isolation of Triterpenoic Acids and Neutral Triterpenoids from Mastic Gum:

Many of the compositions disclosed in this application are prepared by mixing together individual triterpenoic acid(s) and neutral triterpene(s). These individual triterpenoic acid(s) and neutral triterpenoids can either be extracted from a natural source such as Mastic gum, or can be the product of a chemical synthesis. The actual origin of these individual compounds does not influence the properties of the prepared pharmaceutical compositions prepared using these individual compounds. It is therefore understood that the procedures given below for the isolation and synthesis of several individual triterpenoic acids and individual neutral triterpenes are only limited practical examples and that a person skilled in the art may use different isolation procedures and synthesis procedures for obtaining these individual compounds.

The current invention relates to the unexpected biological and pharmaceutical properties of the disclosed pharmaceutical compositions comprising triterpenoic acid(s) and neutral triterpenoid(s). The combination of triterpenoic acid(s) and neutral triterpenoid(s) results in an overall pharmaceutical activity which cannot be obtained by using only the triterpenoic acids or only the neutral triterpenoids.

Example 1A—Preparation of Isolated Acidic Fraction of Mastic Gum

To a 50 gram amount of mastic gum, absolute ethanol (800 ML) was added, and the mixture was left to stand for 24 hours. The mixture was shaken for 30 minutes at 150 rpm and left to stand for two hours. The obtained ethanol solution was decanted from insoluble material into a 3 L round bottom flask. To the insoluble material 400 ML of fresh ethanol was added and the mixture was shaken again 30 minutes at 150 rpm and was left to stand for 30 minutes. The obtained ethanol solution was decanted and added to the first ethanol solution. This step was repeated once more using 200 ML absolute ethanol. This provided 1.4 L of ethanol solution. The ethanol was evaporated using a rotary evaporator, and n-hexane (1.2 Liter) was added to the remaining material, and the mixture was shaken at 150 rpm for 4 hours. It was then left to stand for 4 hours and the hexane solution was decanted from insoluble material into a 3 L Erlenmeyer. To the remaining insoluble material, 800 ML fresh hexane was added and the mixture was shaken for 6 hours at 150 rpm and left to stand for 12 hours. The hexane solution was decanted into the 3 L Erlenmeyer flask containing the first 1.2 L of hexane solution. The hexane was evaporated in a clean 3 L roundbottom flask to give about 30 grams of extract. (Yields range typically from 50-70% depending on the age and particle size of the used Mastic gum.)

The obtained extracted material was subsequently dissolved in diethyl ether (500 ML) and extracted with a 5% aqueous sodium carbonate solution (4×100 ML), the basic aqueous layer and an oily/emulsion layer were carefully separated form the diethyl ether layer. The diethyl ether layer was then additionally extracted with 0.4 N aqueous sodium hydroxide (3×100 ML) and the basic aqueous layer and an oily/emulsion layer were again carefully separated from the diethyl ether layer. (This remaining diethyl ether layer is called diethyl ether layer Nr.I, and will be used herein below in Example 1B). The two basic aqueous extracts (including oily/emulsion layers) were separately acidified to pH 1-2 by slow addition of 10% aqueous hydrochloric acid and were subsequently extracted with fresh diethyl ether (3×200 ML). The thus obtained etheral fractions were combined and dried over anhydrous sodium sulfate. After filtering off the sodium sulfate, the diethyl ether was removed using a rotary evaporator. This procedure gave ca. 15 gram of isolated acidic fraction of mastic gum as a white solid, corresponding to about 50% yield based on the intermediate extract obtained after the ethanol/hexane extraction. This particular isolated acidic fraction obtained from mastic gum as described hereinabove is termed "Acidic Mixture 1".

Based on the starting 50 grams of Mastic gum, the yield for this acidic fraction is about 30%. Typical yields of this particular acidic fraction from mastic gum range from about 25% to about 35%. Without wishing to be bound to any theory or mechanism, these variations in yield can occur due to natural (e.g. seasonal) fluctuations in the composition of the Mastic gum and may also be influenced by age and storage conditions of the Mastic gum.

Example 1B: Isolation of the Neutral Fraction of Mastic Gum

The diethyl ether layer Nr.I obtained in Example 1A was transferred to a clean separatory funnel and washed with water (200 ML) and brine (150 ML). It was then dried over anhydrous sodium sulfate. The sodium sulfate was removed by filtration and the diethyl ether was evaporated using a rotary evaporator. This gave about 15 grams of isolated neutral fraction as a white to off-white sticky solid (which will become a very viscous liquid above 35-40° C.). This is about 50% yield based on the extract obtained after the ethanol/hexane extraction presented in Example 1A. This particular isolated neutral fraction obtained from mastic gum as described here is termed "Neutral Mixture 1". Based on the starting 50 grams of Mastic gum, the yield for this neutral fraction ("Neutral Mixture 1") is about 30%. Typical yields of this neutral fraction from mastic gum range from about 25 to about 35%.

The mass-balance of this particular acid-base extraction described here is typically over 90% and often more than 95% based on the intermediate extract obtained after the ethanol/hexane extraction procedure. The ratio of the thus isolated acidic fraction ("Acidic Mixture 1") to isolated neutral fraction ("Neutral Mixture 1") is usually approaching 1:1 (and nearly always within the 0.8:1.2 to 1.2:0.8 range).

Isolation of individual triterpenoic acids and neutral triterpenoids from isolated acidic fractions and isolated neutral fractions can be accomplished using standard column chromatography and HPLC-methods as known to a person skilled in the art.

It is to be understood, and it is clear to a person skilled in the art, that other extraction protocols can be used to obtain different isolated acidic fractions and isolated neutral fractions from suitable plant materials that can subsequently be used for the isolation of triterpenoic acids and/or neutral triterpenoids.

Example 2—Synthesis of a Triterpenoic Acid and Some Neutral Triterpenoids

Synthesis A: Preparation of Oleanonic Acid

Oleanonic acid was obtained in three steps from oleanolic acid.

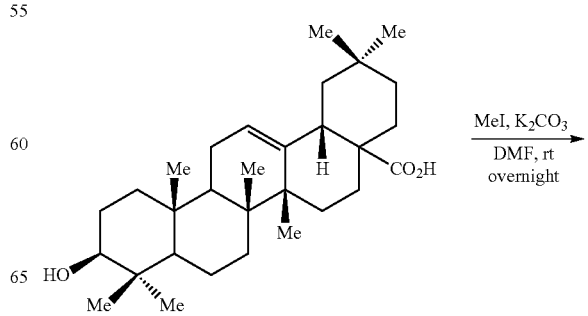

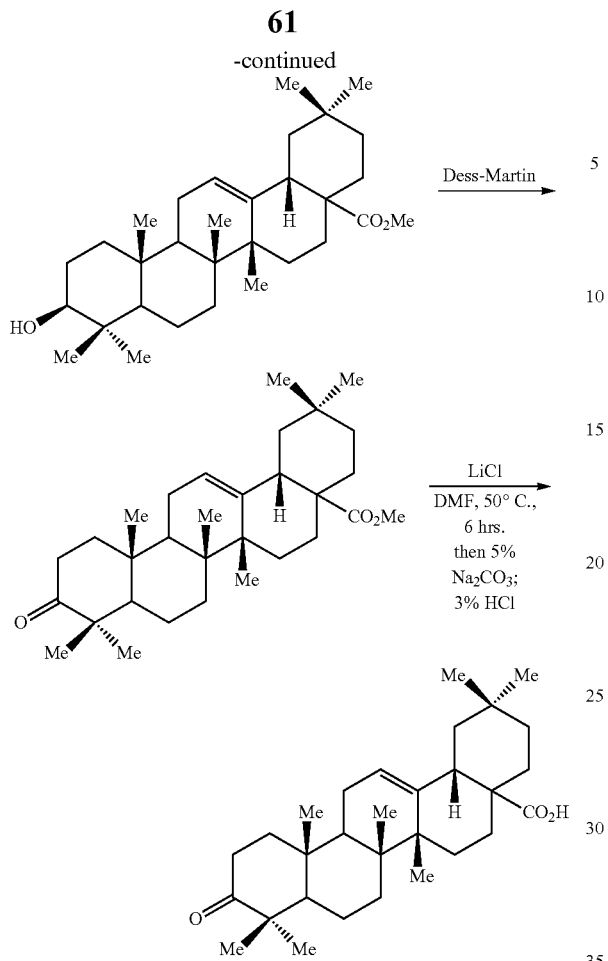

Oleanolic acid was first converted to the corresponding methyl ester by treatment with methyl iodide and potassium carbonate in dimethylformamide (DMF). Oxidation of oleanolic acid methyl ester to oleanonic acid methyl ester was performed using Dess-Martin periodane reagent in dichloromethane (DCM). Hydrolysis of oleanonic acid methyl ester with lithium hydroxide in aqueous THF gave upon acidification the desired oleanonic acid.

Oleanonic acid methyl ester: Oleanolic acid (3.66 g, 1.0 eq) was dissolved in DMF (20.0 vol.). $K_2CO_3$ (3.3 g, 3.0 eq) was added and mixture was stirred for 10 minutes, then methyl iodide (0.75 ml, 1.5 eq) was added. Reaction mixture was carried out at room temperature overnight (full conversion on TLC). $K_2CO_3$ was filtered off from reaction mixture and reaction was poured into ice water. White solid was filtered off, washed with water and dried under reduced pressure to give desired product (3.62 g, 96.0%).

Methyl ester hydrolysis: To oleanonic acid methyl ester (1.0 g) in dry DMF (30 ml) dry LiCl (200 mg) was added and the mixture was stirred under nitrogen at 50° C. for 6 hrs. Upon cooling to room temperature the reaction mixture was quenched by addition of 5% Na2CO3 solution (20 ml) and stirred overnight. Then 3% aqueous HCl was added till pH=2 and the mixture was extracted with diethyl ether (3×50 ml). The combined ether layers were washed with 0.5% HCl, and dried over sodium sulfate. Evaporation of the diethyl ether gave oleanonic acid as a white solid (0.73 g).

Synthesis B: Preparation of NF-A (Betulone)

NF-A was synthesized from betulin-28-acetate in two steps.

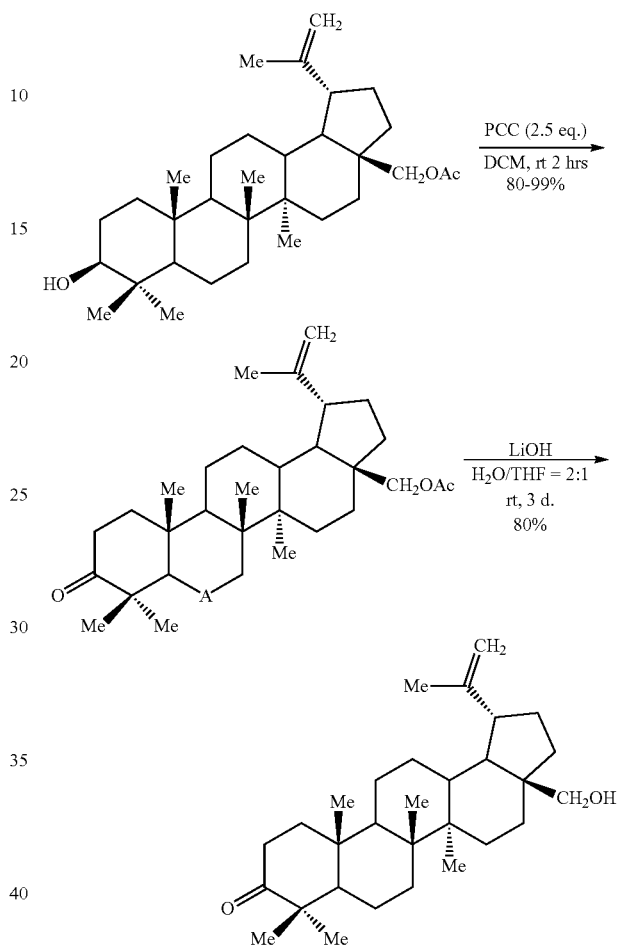

First, the 3-hydroxyl-group was oxidized to the corresponding ketone with PCC in dichloromethane. This was followed by the hydrolysis of the C-28 acetate group to give the desired NF-A (Betulone).

Oxidation step: 28-acetyl betuline (3.2 g, 1.0 eq) was dissolved in DCM (40.0 vol.). Mixture was cooled in ice bath, then PCC (2.13 g, 1.5 eq) was added. Reaction mixture was warmed to room temperature and stirred overnight. Mixture was concentrated on silica gel and purified via flash column chromatography eluted with hexane:EtOAc (95:5->90:10->85:15) to give desired product as white powder (2.85-3.15 g, 80.0-99%).

Acetate hydrolysis: Starting material (1.14 g, 1.0 eq) was dissolved in mixture of $THF:H_2O$ (2:1, 40.0 vol.) then LiOH monohydrate (0.57 g, 10.0 eq) was added. Reaction was carried out at room temperature for 3 days. THF was evaporated. Mixture was extracted with EtOAc (3×), organic layers were combined, dried over MgSO4 and then concentrated under reduced pressure. Crude product was purified via column chromatography eluted with hexane:EtOAc 9:1 to give white powder (80%). Recovered starting material was hydrolyzed once more time, total yield 1.04 g (91.0%).

Synthesis C: Preparation of NF-B (oleanonic alcohol; 28-hydroxy-beta-amyrone)

NF-B was synthesized from oleanonic acid methyl ester in three steps.

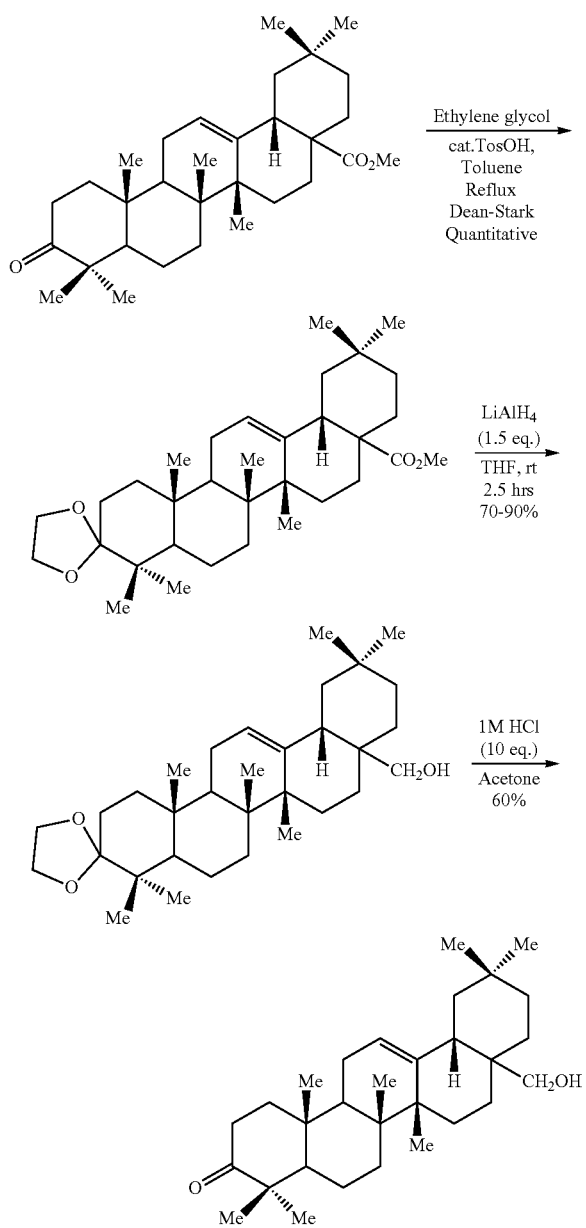

First, the 3-oxo group of oleanonic acid methyl ester (see synthesis A above) was converted with ethylene glycol and catalytic p-TosOH (p-Toluenesulfonic acid) to the corresponding acetal using the standard Dean-Stark set-up with toluene as the solvent. Next the methyl ester group was reduced to the corresponding alcohol with lithium aluminium hydride in THF. Hydrolysis of the acetal with diluted aqueous HCl in acetone gave the desired NF-B (oleanonic alcohol).

Acetal formation: Oleanonic acid methyl ester (1.4 g, 1.0 eq) was dissolved in toluene (20.0 vol.) then TsOH (0.006 g, 0.01 eq) and ethylene glycol (0.46 g, 2.5 eq) were added. Reaction was refluxed for 3 hours under Dean-Stark condenser. TLC indicated full conversion of starting material. Reaction was cooled to RT and quenched with $NaHCO_3$ sat. sol., then extraction to EtOAc was done (3×). Organic layers were washed with water, dried over $MgSO_4$ and concentrated. The crude product was obtained as a grey solid and was used in the next step without any further purification (1.42 g).

Ester reduction: LAH (0.86 g, 2.5 eq) was suspended in THF anh. (20.0 vol.) and was cooled to 0° C. Starting material (3.85 g, 1.0 eq) was dissolved in THF anh. (25.0 vol.) and was added to suspension dropwise. After addition mixture was warmed to room temperature and stirred for 2 hours (full conversion on TLC). Reaction mixture was quenched by "1-2-3 method". The resulting slurry was filtered through Celite. The filtrate was concentrated and used in the next step without further purification (3.5 g).

"1-2-3 Method":

1. Add $H_2O$ to reaction mixture. The same quantity (mL) of water as quantity (g) of LAH
2. Add 15% NaOH to mixture. Double quantity (mL) of 15% NaOH as quantity (g) of LAH
3. Add $H_2O$ to mixture. Triple quantity (mL) of water as quantity (g) of LAH Acetal hydrolysis: Starting material (3.5 g, 1.0 eq) was suspended in mixture of acetone (12.0 vol.) and 1M HCl (10.0 vol.). Reaction mixture was refluxed for 3 hours (full conversion on TLC). Reaction mixture was quenched with $NaHCO_3$ sat. solution to pH 8, extracted with EtOAc (3×), dried over MgSO4 and concentrated. The crude product was purified via column chromatography, eluted with hexane: EtOAc (98:2→95:5→93:7) and triturated with MeOH (1 g crude product/5 mL MeOH). The precipitate was filtered off and dried in vacuo to give desired product as white solid (2.63 g).

Synthesis D and E: Preparation of Oleanolic Alcohol (aka erythrodiol; 28-hydroxy-beta-amyrin) and NF-3 (Oleanonic Aldehyde)

It was found that oleanolic alcohol (aka erythrodiol) was most easily synthesized by reduction of oleanolic acid methyl ester (see synthesis A) with lithium aluminium hydride in THF. (Attempts to prepare this compound by direct reduction of oleanolic acid gave very low yields even after prolonged reaction times and using large excess of lithium aluminium hydride.)

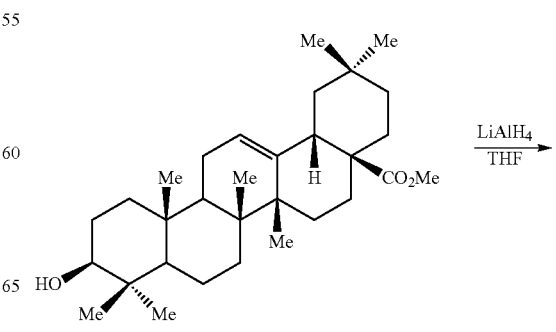

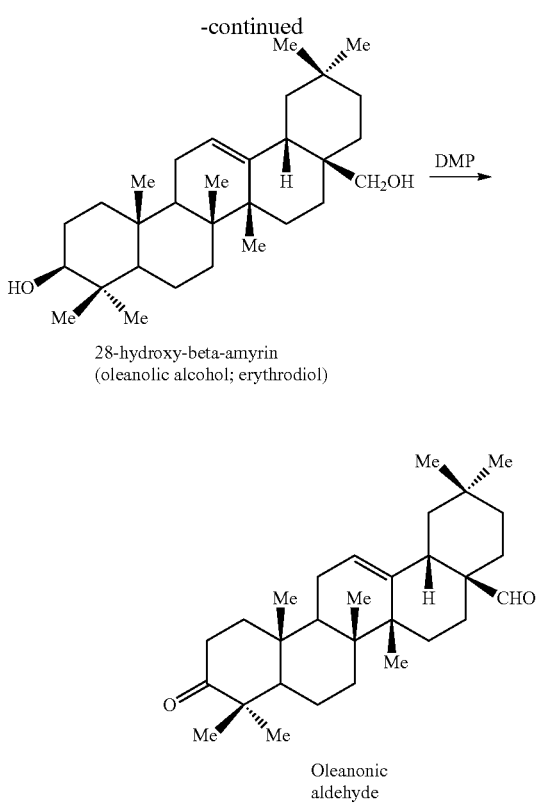

Oleanonic aldehyde (NF-3) was subsequently synthesized from oleanolic alcohol by oxidation using the Dess-Martin periodane reagent.

28-hydroxy-beta-amyrin (Erythrodiol): LAH (1.2 g, 3.0 eq) was suspended in anhydrous THF (10.0 vol.) and was cooled to 0° C. Starting material (5.0 g, 1.0 eq) was dissolved in anhydrous THF (15.0 vol.) and was added to suspension dropwise. After addition, the mixture was allowed to reach room temperature and was further stirred for 2 hours (full conversion on TLC). The reaction was quenched by the "1-2-3 method" (see synthesis C). The resulting slurry was filtered through Celite. Filtrate was concentrated and the crude product was used in the next step without further purification (4.60 g).

Oleanonic aldehyde (NF-3): 28-hydroxy-beta-amyrin (2.8 g, 1.0 eq) was dissolved in DCM (20.0 vol.) then was added DMP (5.36 g, 2.0 eq). Reaction was carried out for 1 hour. Crude product was concentrated on silica gel and purified via column chromatography eluted with hexane, then hexane:EtOAc (99:1→9:1) to give oleanonic aldehyde as a white solid (0.60 g).

Synthesis F: Preparation of Masticadienonic Aldehyde

Masticadienonic aldehyde was prepared from masticadienonic acid in three steps. The methyl ester of masticadienonic acid was prepared using diazomethane in diethyl ether or by using trimethylsilyldiazomethane in dichloromethane (DCM)/methanol. Reduction of the methyl ester with lithium aluminium hydride gave masticadienediol. The diol was then converted into masticadienonic aldehyde by oxidation with Dess-Martin Periodane reagent.

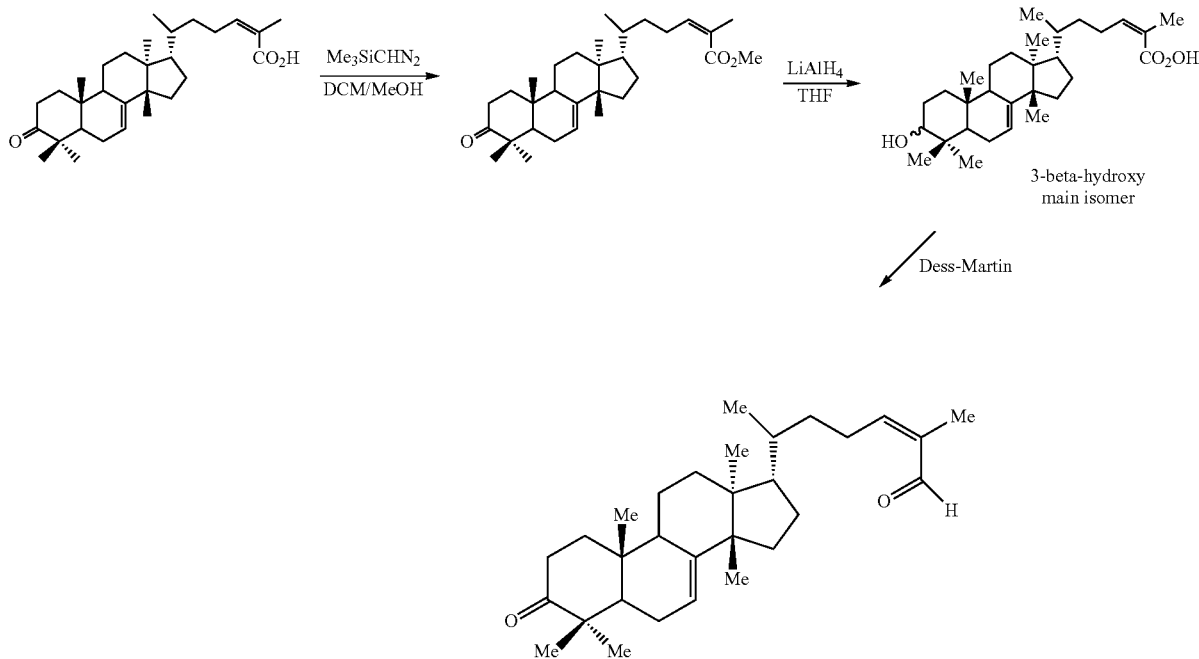

Masticadienonic acid methyl ester: MDA (1 g, 1.0 eq) was dissolved in mixture of DCM (10.0 ml) and MeOH (10.0 ml) and 2M solution of TMS-diazomethane in DCM (4.4 ml, 4.0 eq) was added dropwise within 30 minutes. Color of the solution turned to light yellow, reaction mixture was stirred for 30 minutes. Reaction progress was monitored on TLC (hexane:EA 4:1, visualized in pAA stain solution).

The reaction was quenched by addition of few drops of AcOH until the yellowish color disappeared. The mixture was concentrated, dissolved in EA and washed with sat. NaHCO$_3$ and sat. brine. Organic layer was dried and concentrated to give desired MDA-methyl ester (1.02 g). Product was used in subsequent step without further purification.

Masticadienediol: LAH (0.21 g, 10.0 eq) was suspended in THF anh. (20.0 vol.) and was cooled to 0° C. MDA (0.25 g, 1.0 eq) was dissolved in THF anh. (25.0 vol.) and was added to suspension dropwise within 15 minutes. After addition mixture was warmed to room temperature and stirred for 2 hours (full conversion on TLC). Reaction mixture was quenched by "1-2-3 method". Resulted slurry was filtrated through Celite. Filtrate was concentrated and was purified via column chromatography eluted with appropriate eluent mixture (DCM:MeOH) to give masticadienediol (110 mg). The same reaction on 2.5 g scale gave 1.7 gr product. A mixture of isomers was obtained, with the 3-beta-isomer as the main product (alpha/beta ratio ca. 5:1). The isomers can be further separated by preparative HPLC.

Masticadienonic aldehyde: masticadienediol (0.45 g, 1.0 eq) was dissolved in DCM (20.0 vol.) then was added DMP (0.95 g, 2.2 eq). Reaction was carried out for 2 hours. Crude product was concentrated on silica gel and purified via column chromatography eluted with hexane, then hexane:EtOAc (99:1→9:1) to give desired product as white solid (0.3 g).

Synthesis G: Preparation of Isomasticadienonic Aldehyde

Isomasticadienonic aldehyde was synthesized from isomasticadienonic acid using the same sequence of reactions as used for masticadienonic aldehyde in Synthesis E described above.

Isomasticadienonic acid methyl ester: IMDA (1 g, 1.0 eq) was dissolved in mixture of DCM (10.0 ml) and MeOH (10.0 ml) and 2M solution of TMS diazomethane (4.4 ml, 4.0 eq) was added dropwise within 30 minutes. Color of the solution turned to light yellow, reaction mixture was stirred for 30 minutes. Reaction progress was monitored on TLC (hexane:EA 4:1, visualized in pAA stain solution).

The reaction was quenched by addition of few drops of AcOH until the yellowish color disappeared. The mixture was concentrated, dissolved in EA and washed with sat. NaHCO$_3$ and sat. brine. Organic layer was dried and concentrated to give desired IMDA methyl ester (1.02 g). Product was used in subsequent step without further purification.

Isomasticadienediol: LAH (0.21 g, 10.0 eq) was suspended in THF anh. (20.0 vol.) and was cooled to 0° C. MDA (0.25 g, 1.0 eq) was dissolved in THF anh. (25.0 vol.) and was added to suspension dropwise within 15 minutes. After addition mixture was warmed to room temperature and stirred for 2 hours (full conversion on TLC). Reaction mixture was quenched by "1-2-3 method". Resulted slurry was filtrated through Celite. Filtrate was concentrated and was purified via column chromatography eluted with appropriate eluent mixture (DCM:MeOH) to give isomasticadienediol (0.16 g, 65.0%). The same reaction on 2.5 g scale gave 1.55 gr product (61%). A mixture of isomers was obtained, with the 3-beta-isomer as the main product (alpha/beta ratio ca. 5:1). The isomers can be further separated by preparative HPLC.

Isomasticadienonic aldehyde: isomasticadienediol (0.45 g, 1.0 eq) was dissolved in DCM (20.0 vol.) then was added DMP (0.95 g, 2.2 eq). Reaction was carried out for 2 hours. Crude product was concentrated on silica gel and purified via column chromatography eluted with hexane, then hexane:EtOAc (99:1→9:1) to give desired product as white solid (0.4 g).

Synthesis H: Preparation of NF-2 ((8R)-3-Oxo-8-hydroxypolypoda-13E,17E,21-triene)

NF-2 was prepared from NF-1 by oxidation of the secondary hydroxyl group to the ketone using Dess-Martin periodane reagent.

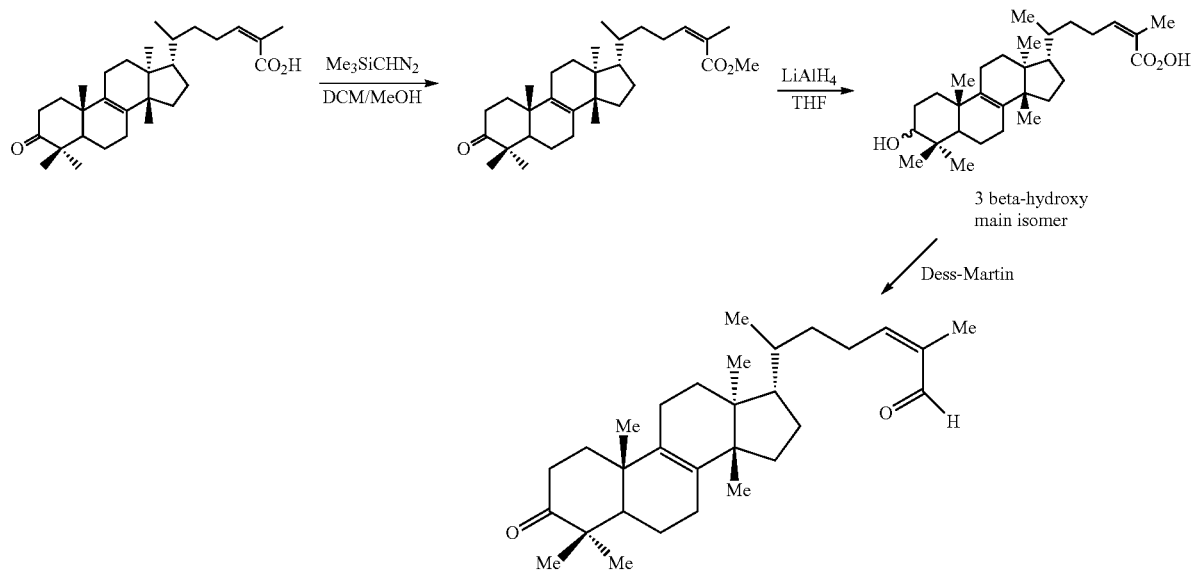

3 beta-hydroxy main isomer

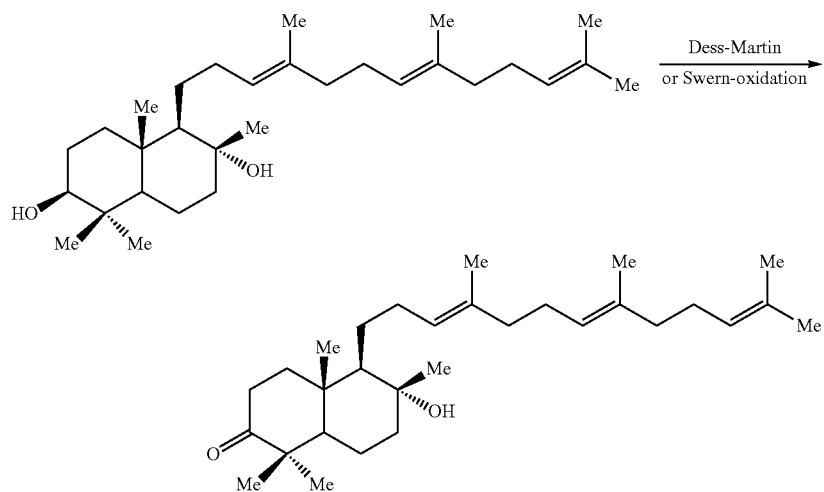

NF-2 ((8R)-3-Oxo-8-hydroxypolypoda-13E,17E,21-triene): NF-1 (0.90 g, 1.0 eq) was dissolved in DCM (20.0 vol.) then was added DMP (1.90 g, 2.2 eq). Reaction was carried out for 2 hours. Crude product was concentrated on silica gel and purified via column chromatography eluted with hexane, then hexane:EtOAc (9:1→3:1) to give desired product as white solid (0.72 g).

Other suitable oxidation methods for this reaction are the Swern-oxidation, pyridinium chlorochromate in DCM and the Oppenauer oxidation.

Synthesis I: Preparation of Beta-Amyrin

Beta-amyrin was prepared in five steps from oleanolic acid.

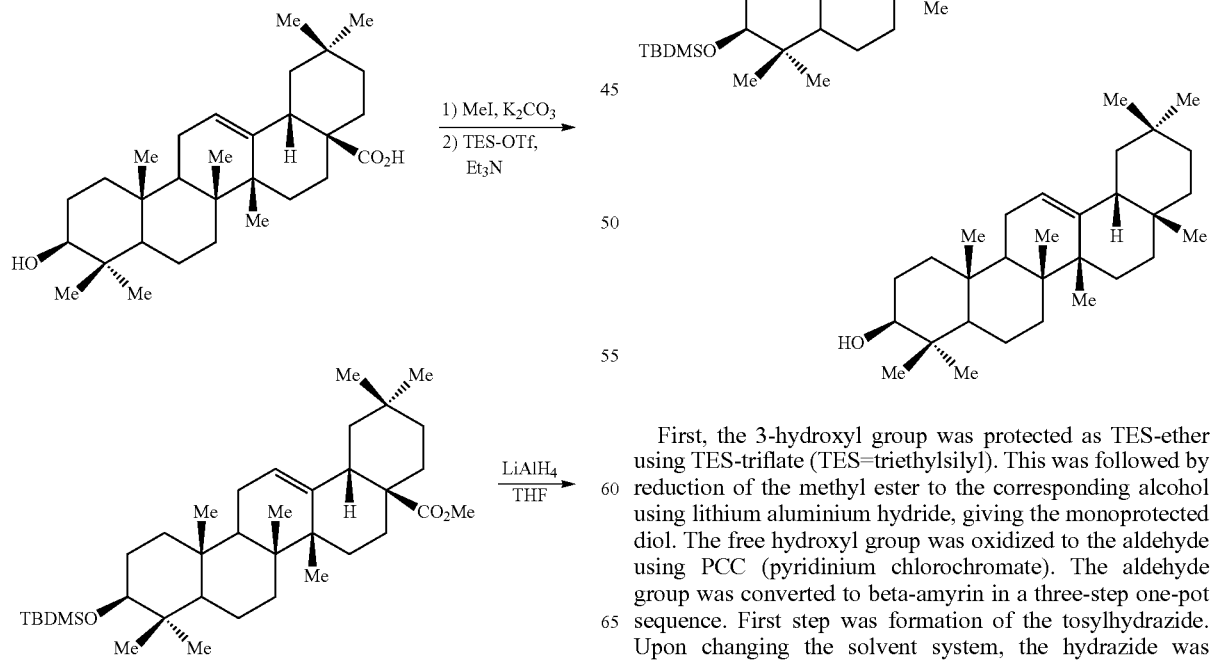

First, the 3-hydroxyl group was protected as TES-ether using TES-triflate (TES=triethylsilyl). This was followed by reduction of the methyl ester to the corresponding alcohol using lithium aluminium hydride, giving the monoprotected diol. The free hydroxyl group was oxidized to the aldehyde using PCC (pyridinium chlorochromate). The aldehyde group was converted to beta-amyrin in a three-step one-pot sequence. First step was formation of the tosylhydrazide. Upon changing the solvent system, the hydrazide was reduced by refluxing with sodiumborohydride which simultaneously removed the TES-protecting group resulting in direct formation of the desired beta-amyrin.

Oleanolic Acid Methyl Ester:

Oleanolic acid (5.0 g, 1.0 eq) was dissolved in DMF (20.0 vol.). K$_2$CO$_3$ (4.54 g, 3.0 eq) was added and mixture was stirred for 5-10 min, then CH$_3$I (2.0 eq) was added. Reaction mixture was carried out at room temperature overnight (full conversion on TLC). K$_2$CO$_3$ was filtered off from reaction mixture and reaction was poured into ice water. White solid was filtered off, washed with water and dried under reduced pressure. Crude product was used in the next step without any purification (5.1 g).

TES Protection of 3-Hydroxyl Group:

Oleanolic acid methyl ester (5.1 g, 1.0 eq) was dissolved in DCM (20.0 vol.) containing TEA (9.9 ml, 6.6 eq). The mixture was stirred for 15 minutes and TESOTf (8.0 ml, 3.3 eq) was added dropwise. The reaction mixture was stirred overnight at RT until completion. (TLC hexane:EA; 4:1). The mixture was diluted with 1M HCl and extracted with DCM (2×). Combined organic layers were dried and concentrated. The crude mixture was purified by column chromatography (hexane:EA 98:2) to give desired product as white solid. (6.6 g).

Ester Reduction:

LAH (1.29 g, 2.5 eq) was suspended in THF anh. (20.0 vol.) and was cooled to 0° C. Starting material (6.61 g, 1.0 eq) was dissolved in THF anh. (25.0 vol.) and was added to suspension dropwise. After addition, mixture was warmed to room temperature and stirred for 2 hours (full conversion on TLC). Reaction was quenched by "1-2-3 method" (see Synthesis C). The resulting slurry was filtered through Celite. The filtrate was concentrated and used in the next step without further purification (4.55 g).

Alcohol Oxidation:

Mono-protected diol (1.0 g, 1.0 eq) was dissolved in DCM (20.0 vol.) and cooled to 0° C. To that was added PCC (0.58 g, 1.5 eq) and mixture was stirred for 2 h at RT. Reaction progress was monitored on TLC (hexane:EA 9:1). Reaction was concentrated on SiO$_2$ and purified via column chromatography eluted with hexane:EA to give pure product (0.76 g).

One-Pot Conversion of TES-Aldehyde Intermediate into Beta-Amyrin (Hydrazide Formation; Reduction; TES Cleavage):

Starting material (0.62 g, 1.0 eq) was suspended in EtOH (26.0 vol.), p-toluenesulfonyl hydrazide (0.25 g, 1.2 eq) was added and mixture was refluxed overnight. Reaction progress was monitored on TLC (hexane:EA 7:3). EtOH was concentrated and residue was dissolved in THF (33.0 vol.) and water (5.0 vol.) and NaBH$_4$ (0.42 g, 10.0 eq). Reaction was continued at RT overnight and then 2 hours at reflux. Reaction was cooled down and portioned between water and EA, layers were separated, water layer was extracted 2× with EA. Combined organic layers were dried and concentrated to give crude residue. Crude reaction mixture purified via column chromatography eluted with hexane:EA to give beta-amyrin as a white solid (100 mg).

Synthesis J: Preparation of Beta-Amyrone

Beta-amyrone was prepared from beta-amyrin by oxidation of the hydroxyl group to the corresponding ketone using pyridinium chlorochromate (PCC). Other suitable methods are the Dess-Martin reagent or Swern oxidation.

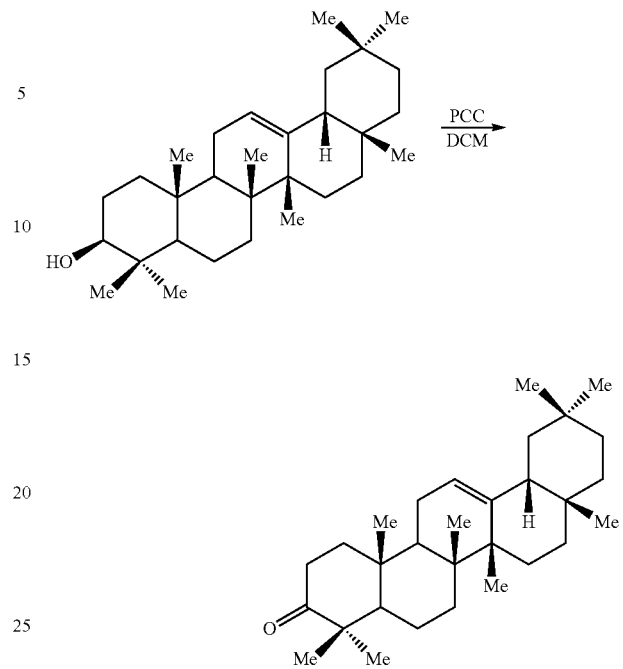

Via PCC-oxidation: Beta-amyrin (100 mg, 1.0 eq) was dissolved in DCM (20.0 vol.) and cooled to 0° C. To that was added PCC (76 mg, 1.5 eq) and mixture was stirred for 1 h at RT. Reaction progress was monitored on TLC (hexane:EA 6:1). Reaction was concentrated on SiO$_2$ and purified via column chromatography eluted with hexane:EA (60:1→20:1) to give pure product (63 mg).

Via Dess-Martin Reagent: Starting material (100 mg, 1.0 eq) was dissolved in DCM (20.0 vol.) then was added DMP (0.95 g, 2.2 eq). Reaction was carried out for 2 hours. Crude product was concentrated on silica gel and purified via column chromatography eluted with hexane:EA (60:1→20:1) to give pure product to give desired product as white solid (0.67 g).

Synthesis K: Preparation of 28-Oxo-Lupen-3-One 28-oxo-lupen-3-one was synthesized from NF-A (betulone, see Synthesis B), by oxidation of the 28-hydroxyl group to the corresponding aldehyde with Dess-Martin periodane.

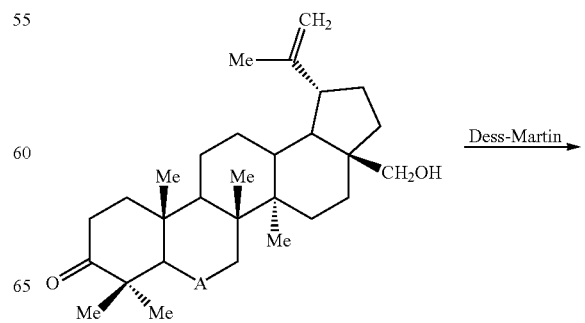

-continued

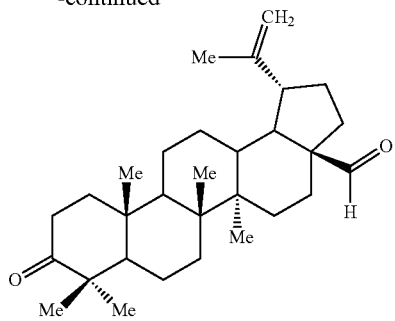

Starting material (1.0 g, 1.0 eq) was dissolved in DCM (20.0 vol.) then was added DMP (2.20 g, 2.2 eq). Reaction was carried out for 2 hours. Crude product was concentrated on silica gel and purified via column chromatography eluted with hexane, then hexane:EtOAc (99:1→9:1) to give desired product as white solid (0.74 g).

Other suitable oxidation methods for this reaction where the Swern-oxidation, pyridinium chlorochromate in DCM.

Synthesis L: Preparation of Oleanolic Aldehyde

Oleanolic aldehyde was prepared in two steps from the mono-protected diol intermediate from beta-amyrin Synthesis I.

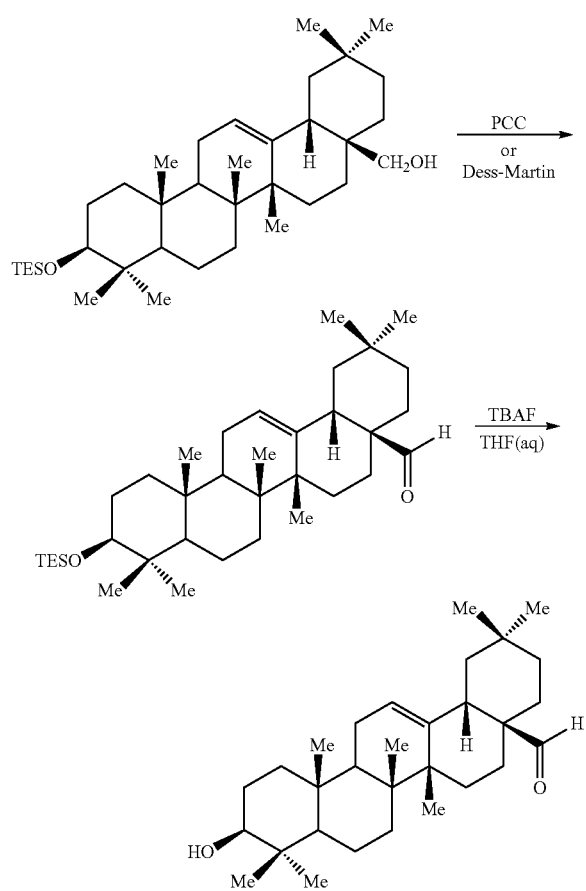

The free hydroxyl group was oxidized to the corresponding aldehyde using PCC or Dess-Martin Periodane. This was followed by removal of the TES-group with TBAF in aqueous THF to give the desired oleanolic aldehyde.

Via PCC-oxidation: The mono-protected diol (1.0 g, 1.0 eq) was dissolved in DCM (20.0 vol.) and cooled to 0° C. To that was added PCC (0.58 g, 1.5 eq) and mixture was stirred for 2 h at RT. Reaction progress was monitored on TLC (hexane:EA 9:1). Reaction was concentrated on SiO$_2$ and purified via column chromatography eluted with hexane:EA to give pure product (0.76 g).

Via Dess-Martin oxidation: The mono-protected diol (1.0 g, 1.0 eq) was dissolved in DCM (20.0 vol.) then was added DMP (2.20 g, 2.2 eq). Reaction was carried out for 2 hours. Reaction progress was monitored on TLC (hexane:EA 9:1). The reaction mixture was concentrated on SiO$_2$ and purified via column chromatography eluted with hexane:EA to give pure product (0.69 g).

Removal of TES-group: (150 mg, 1.0 eq) was dissolved in THF (15.0 vol.) and cooled to 0° C. To that was added TBAF (113 mg, 2.0 eq) and mixture was stirred overnight at RT. Reaction progress was monitored on TLC (hexane:EA 4:1). Reaction was concentrated on SiO$_2$ and purified via column chromatography eluted with hexane:EA (9:1→6:1) to give pure product (86 mg).

Some suitable references for synthesis of several triterpenoids encountered in the current application are:

D. Barton et al. J. Chem. Soc. 1956, 4150,

V. Domingo et al. J. Org. Chem. 74, 6151, 2009.

V. Domingo et al. Org. Biomol. Chem. 11, 559, 2013.

J. Justicia et al. Eur. J. Org. Chem. 10, 1778, 2004.

Example 3—Preparation of Pharmaceutical Compositions and Formulations

The pharmaceutical compositions as shown in Table 1 were prepared by mixing and dissolving the required amounts of triterpenoic acid(s) and neutral triterpenoid(s) in a suitable solvent (e.g. diethylether) followed by addition of the required amount of pharmaceutically acceptable carrier. The mixture was then shaken or stirred until a homogeneous clear solution was obtained, and the suitable solvent (e.g. diethyl ether) was removed using vacuum (e.g. a rotary evaporator). This gave the desired pharmaceutical composition.

Table 1A shows the pharmaceutical compositions that were prepared using diethyl ether as solvent, and pharmaceutical grade (NF-grade) cottonseed oil (stabilized with ca. 900 ppm BHT) as the pharmaceutically acceptable carrier.

TABLE 1A

| Cpd/Entry | A | B | C | D | E | F | G | H | I | J | K |
|---|---|---|---|---|---|---|---|---|---|---|---|
| 1 | Acidic-1 | Neutral-2 | | | | | | | | | |
| 2 | Acidic-1 | NF-1 | NF-2 | NF-3 | NF-4 | NF-A | NF-B | NF-P | | | |
| 3 | Acidic-1 | NF-1 | NF-2 | NF-3 | NF-4 | NF-A | NF-B | | | | |
| 4 | Acidic-1 | NF-1 | NF-2 | NF-3 | NF-4 | | | | | | |
| 5 | Acidic-1 | NF-1 | NF-2 | NF-3 | | | | | | | |
| 6 | Acidic-1 | NF-1 | NF-2 | | | | | | | | |
| 7 | Acidic-1 | NF-1 | | | | | | | | | |
| 8 | Acidic-1 | NF-2 | | | | | | | | | |
| 9 | Acidic-1 | NF-3 | | | | | | | | | |
| 10 | Acidic-2 | Neutral-1 | | | | | | | | | |
| 11 | Acidic-2 | Neutral-2 | | | | | | | | | |
| 12 | Acidic-2 | NF-1 | NF-2 | NF-3 | NF-4 | NF-A | NF-B | NF-P | | | |
| 13 | Acidic-2 | NF-1 | NF-2 | NF-3 | NF-4 | NF-A | NF-A | | | | |
| 14 | Acidic-2 | NF-1 | NF-2 | NF-3 | NF-4 | | | | | | |
| 15 | Acidic-2 | NF-1 | NF-2 | NF-3 | | | | | | | |
| 16 | Acidic-2 | NF-1 | NF-2 | | | | | | | | |
| 17 | Acidic-2 | NF-1 | NF-3 | | | | | | | | |
| 18 | Acidic-2 | NF-1 | NF-4 | | | | | | | | |
| 19 | Acidic-2 | NF-1 | | | | | | | | | |
| 20 | Acidic-2 | NF-2 | | | | | | | | | |
| 21 | Acidic-2 | NF-3 | | | | | | | | | |
| 22 | Acidic-2 | NF-4 | | | | | | | | | |
| 23 | Acidic-2 | NF-A | | | | | | | | | |
| 24 | Acidic-2 | NF-B | | | | | | | | | |
| 25 | MDA | IMDA | NF-1 | NF-2 | NF-3 | NF-4 | NF-A | NF-B | | | |
| 26 | MDA | IMDA | NF-1 | NF-2 | NF-3 | NF-4 | NF-A | NF-B | NF-P | | |
| 27 | MDA | IMDA | NF-1 | NF-2 | NF-3 | NF-4 | NF-A | NF-B | NF-P | MLA | IMLA |
| 28 | MDA | IMDA | NF-1 | NF-2 | NF-A | NF-B | NF-P | | | | |
| 29 | MDA | IMDA | NF-1 | NF-2 | NF-A | NF-B | | | | | |
| 30 | MDA | IMDA | NF-3 | NF-4 | NF-A | NF-B | | | | | |
| 31 | MDA | IMDA | NF-1 | NF-2 | NF-3 | NF-4 | | | | | |
| 32 | MDA | IMDA | NF-1 | NF-2 | NF-3 | | | | | | |
| 33 | MDA | IMDA | NF-1 | NF-2 | NF-4 | | | | | | |
| 34 | MDA | IMDA | NF-1 | NF-2 | | | | | | | |
| 35 | MDA | IMDA | NF-1 | | | | | | | | |
| 36 | MDA | IMDA | NF-2 | | | | | | | | |
| 37 | MDA | IMDA | NF-3 | | | | | | | | |
| 38 | MDA | IMDA | NF-4 | | | | | | | | |
| 39 | MDA | IMDA | OA | MA | NF-1 | NF-2 | | | | | |
| 40 | MDA | IMDA | OA | MA | NF-1 | | | | | | |
| 41 | MDA | IMDA | OA | MA | NF-2 | | | | | | |
| 42 | MDA | IMDA | OA | MA | NF-3 | NF-4 | NF-A | NF-B | NF-P | | |
| 43 | MDA | IMDA | OA | MA | NF-3 | NF-4 | | | | | |
| 44 | MDA | IMDA | OA | NF-1 | NF-2 | | | | | | |
| 45 | MDA | IMDA | OA | NF-1 | | | | | | | |
| 46 | MDA | IMDA | OA | NF-2 | | | | | | | |

Additional formulations containing 3-OAc-MLA, 3-OAc-IMLA, 3-Ac-epi-MLA and 3-OAc-epi-IMLA which have been prepared as indicated above are indicated in Table 1B.

TABLE 1B

| Entry | A | B | C | D | E | F | G | H | I |
|---|---|---|---|---|---|---|---|---|---|
| 47 | MDA | IMDA | 3-OAc-MLA | 3-OAc-IMLA | OA | NF-1 | NF-2 | NF-3 | NF-4 |
| 48 | MDA | IMDA | 3-OAc-MLA | 3-OAc-IMLA | OA | NF-1 | NF-2 | NF-A | NF-B |
| 49 | MDA | IMDA | 3-OAc-MLA | 3-OAc-IMLA | OA | NF-1 | NF-2 | | |
| 50 | MDA | IMDA | 3-OAc-MLA | 3-OAc-IMLA | NF-1 | NF-2 | | | |
| 51 | MDA | IMDA | 3-OAc-MLA | 3-OAc-IMLA | NF-1 | NF-2 | NF-3 | NF-4 | |
| 52 | MDA | IMDA | 3-OAc-MLA | 3-OAc-IMLA | NF-1 | NF-2 | NF-A | NF-B | |
| 53 | MDA | IMDA | 3-OAc-MLA | 3-OAc-IMLA | OA | MA | NF-1 | NF-2 | |
| 54 | MDA | IMDA | 3-OAc-MLA | 3-OAc-IMLA | NF-1 | NF-4 | | | |
| 55 | MDA | IMDA | 3-OAc-MLA | 3-OAc-IMLA | NF-1 | NF-3 | | | |
| 56 | MDA | IMDA | 3-OAc-MLA | 3-OAc-IMLA | NF-2 | NF-4 | | | |
| 57 | MDA | IMDA | 3-OAc-MLA | 3-OAc-IMLA | NF-2 | NF-3 | | | |
| 58 | MDA | IMDA | 3-OAc-MLA | 3-OAc-IMLA | NF-1 | NF-2 | NF-3 | | |
| 59 | MDA | IMDA | 3-OAc-MLA | 3-OAc-IMLA | NF-1 | | | | |
| 60 | MDA | IMDA | 3-OAc-MLA | 3-OAc-IMLA | NF-2 | | | | |
| 61 | MDA | IMDA | 3-OAc-epi-MLA | 3-OAc-epi-IMLA | OA | NF-1 | NF-2 | NF-3 | NF-4 |
| 62 | MDA | IMDA | 3-OAc-epi-MLA | 3-OAc-epi-IMLA | NF-1 | NF-2 | NF-3 | NF-4 | |
| 63 | MDA | IMDA | 3-OAc-epi-MLA | 3-OAc-epi-IMLA | OA | NF-1 | NF-2 | | |
| 64 | MDA | IMDA | 3-OAc-epi-MLA | 3-OAc-epi-IMLA | NF-1 | NF-2 | | | |
| 65 | MDA | IMDA | 3-OAc-epi-MLA | 3-OAc-epi-IMLA | NF-1 | NF-2 | NF-3 | | |

TABLE 1B-continued

| Entry | A | B | C | D | E | F | G | H | I |
|---|---|---|---|---|---|---|---|---|---|
| 66 | MDA | IMDA | 3-OAc-epi-MLA | 3-OAc-epi-IMLA | NF-1 | NF-4 | | | |
| 67 | MDA | IMDA | 3-OAc-epi-MLA | 3-OAc-epi-IMLA | NF-1 | NF-3 | | | |
| 68 | MDA | IMDA | 3-OAc-epi-MLA | 3-OAc-epi-IMLA | NF-2 | NF-3 | | | |
| 69 | MDA | IMDA | 3-OAc-epi-MLA | 3-OAc-epi-IMLA | NF-2 | NF-4 | | | |
| 70 | MDA | IMDA | 3-OAc-epi-MLA | 3-OAc-epi-IMLA | NF-1 | | | | |
| 71 | MDA | IMDA | 3-OAc-epi-MLA | 3-OAc-epi-IMLA | NF-2 | | | | |

Example 4—Synergistic Effect of Combinations of Neutral Triterpenoids and Triterpenoic Acids in Rat tMCAO Stroke Model The Middle Cerebral Artery occlusion (MCAO) model is a reliable model for stroke in rats and mimics the human condition. Generally, focal ischemia results in localized brain infarction and is induced by middle cerebral artery occlusion (MCAO) in rats. Occlusion of MCA leads to damage to the sensorimotor cortex due to neuronal loss, whereas the level of this damage can be assessed by histology evaluation of the infarct size and various behavior tests.

Transient middle cerebral artery (tMCAO) occlusion was performed according to the method described by R. Schmid-Elsaesser et al. Stroke. 1998; 29(10):2162-2170. For the experiments described herein, the animals are anesthetized using ketamine/xylazine solution. The animal's neck is then shaved and a midline incision is made in the skin of the neck, and the tissue underneath is bluntly dissected. The right Common Carotid Artery (CCA) was exposed through a midline neck incision and carefully dissected free from surrounding nerves and fascia—from its bifurcation to the base of the skull. The occipital artery branches of the ECA (External Carotid Artery) were then isolated, and these branches were dissected and coagulated. The ECA was dissected further distally and coagulated along with the terminal lingual and maxillary artery branches, which was then divided. The ICA (Internal Carotid Artery) was isolated and carefully separated from the adjacent vagus nerve, and the pterygopalatine artery was ligated close to its origin with a 5-0 nylon suture. Next a 4-0 silk suture was tied loosely around the mobilized ECA stump, and a 4 cm length of 4-0 monofilament nylon suture (the tip of the suture was blunted by using a flame, and the suture was coated with polylysine, prior to insertion) was inserted through the proximal ECA into the ICA and thence into the circle of Willis, effectively occluding the MCA. The surgical wound was closed and the animals were returned to their cages to recover from anesthesia. Two hours after occlusion rats were re-anesthetized, monofilament was withdrawn to allow reperfusion, surgical wound was closed and rats were returned to their cages.

Two hours post occlusion just before reperfusion animals were subjected to neurological evaluation using the "Neuroscore for exclusion criteria" (Chen J. et al. Stroke. 2001; 32(4):1005-1011.). Only animals with an overall score of >10 were included in the study.

Immediately post reperfusion, three hours after stroke induction, rats were treated with compositions A, B, C, D, E and F via subcutaneous injection. The experiment was carried out with a total of 68 rats as specified hereinbelow.

Forelimb and Hind Limb Placing Tests

For the forelimb-placing test, the examiner holds the rat close to a tabletop and scores the rat's ability to place the forelimb on the tabletop in response to whisker, visual, tactile, or proprioceptive stimulation. Similarly, for the hind limb placing test, the examiner assesses the rat's ability to place the hind limb on the tabletop in response to tactile and proprioceptive stimulation. Separate sub-scores are obtained for each mode of sensory input and added to give total scores (for the forelimb placing test: 0=normal, 12=maximally impaired; for the hind limb placing test: 0=normal; 6=maximally impaired). Scores are given in half-point increments (see below). Typically, there is a slow and steady recovery of limb placing behavior during the first month after stroke.

Fore limb placing test (0-12):
    Whisker placing (0-2);
    Visual placing (forward (0-2), sideways (0-2))
    Tactile placing (dorsal (0-2), lateral (0-2))
    Proprioceptive placing (0-2).

Evaluation was carried out (a) prior to the operation, (b) on day 15 after stroke induction and (c) on day 58 after stroke induction. Difference in forelimb placing tests between days 58 and 15 ($p<0.01$) are presented in FIG. 1. The high difference values in groups A, B, C, E and F. indicated a significant healing and recovered post-stroke neurological function in the triterpenoid-treated groups compared to the placebo group D.

Figure 2:
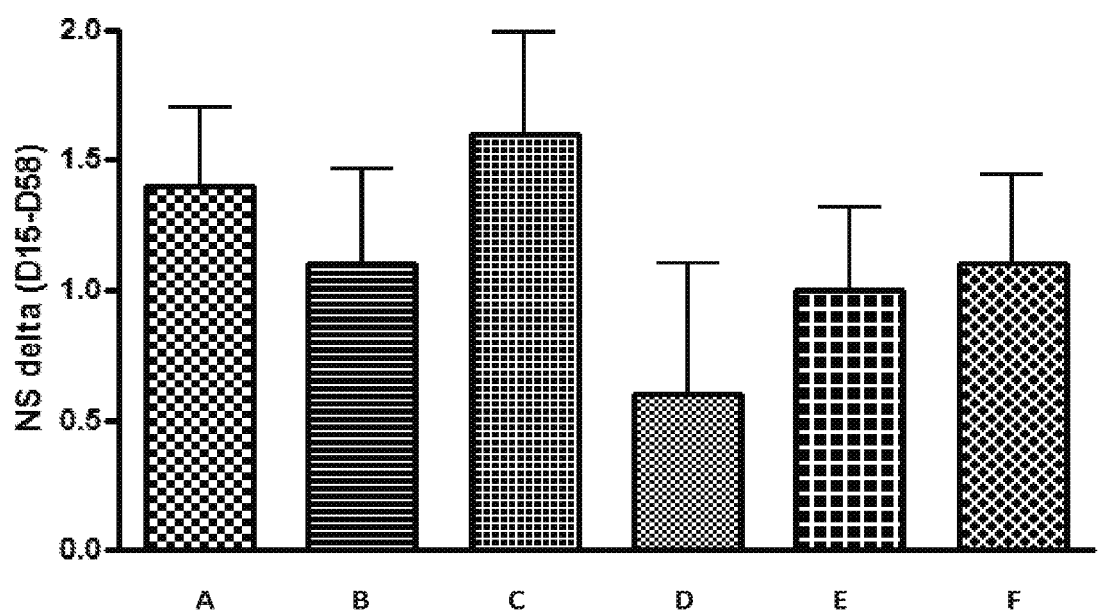
FIG. 2 displays bar graphs showing neurological scoring in Groups A-F (Respective Entries nr. 4 (group-A); 27 (group B); 31 (Group C); 2 (Group E); 26 (Group F) of Table 1A) of the neurological score test in a tMCAO stroke model in rats. Group D is placebo control.

Neurological Scoring (Neuroscore):

The Modified Neurological Rating Scale (mNRS), or Neuroscore, was carried out (a) prior to the operation, (b) on day 15 after stroke induction and (c) on day 58 after stroke Difference in neuroscores between days 58 and 15 ($p<0.01$) are presented in FIG. 2. The high difference values in groups A, B, C, E and F. indicated a significant healing and recovered post-stroke neurological function in the triterpenoid-treated groups compared to the placebo group D.

Compositions as Used in tMCAO Stroke Model

"Acidic Mixture 1" means the isolated acidic fraction of Mastic gum as prepared according to Example 1A. "Acidic Mixture 1" contains as main compounds the following:
    MA: Moronic acid (12-15%)
    OA: Oleanonic acid (18-20%)
    MDA: 24-Z-Masticadienonic acid (20-22%)
    IMDA: 24-Z-Isomasticadienonic acid (22-26%)
    3-beta-OAc-24-Z-masticadienolic acid (4-7%)
    3-beta-OAc-24-Z-isomasticadienolic acid (4-7%)

It further contains a number of other triterpenoic acids in small amounts, typically less than 5%. Possible triterpenoic acids that it may contain are:
    MLA: 3-beta-masticadienolic acid
    IMLA: 3-beta-isomasticadienolic acid
    Dihydromasticadienonic acid
    Dihydroisomasticadienonic acid "Acidic Mixture 2" contains the following compounds in % (w/w):
MA: Moronic acid (15%)
    OA: Oleanonic acid (15%)
    MDA: 24-Z-Masticadienonic acid (25%)
    IMDA: 24-Z-Isomasticadienonic acid (30%)
    3-beta-OAc-24-Z-masticadienolic acid (8%)
    3-beta-OAc-24-Z-isomasticadienolic acid (7%)

In Table 2, "Acidic Mixture 1 (2.5%)" means a 2.5% (w/w) formulation of the acidic fraction as isolated in Example 1A in cottonseed oil. Likewise, "Acidic Mixture 2 (2.5%)" means a 2.5% (w/w) formulation of "Acidic Mixture 2" as defined above, "Neutral Mixture 1" is the neutral fraction as prepared according to Example 1A,B;

"Neutral Mixture 2" contains the following neutral triterpenoids:

NF-1: (8R)-3-beta, 8-dihydroxypolypoda-13E,17E,21-triene
NF-2: (8R)-3-Oxo-8-hydroxypolypoda-13E, 17E,21-triene
NF-3: Oleanonic aldehyde
NF-4: Tirucallol
NF-P: Dipterocarpol (20-hydroxydammar-24-en-3-one)
NF-A: (Betulon), 28-hydroxylup-20(29)-en-3-one
NF-B: Oleanonic alcohol; (28-hydroxy-beta-amyrone)
3-beta-hydroxy-13-alpha-malabarica-14(26), 17E,21-triene
20-hydroxy-lupan-3-one
28-Nor-17-hydroxylupen-3-one
28-oxo-lupen-3-one
28-nor-beta-amyrone
Isomasticadienonic aldehyde
Isomasticadienediol
Masticadienediol
Oleanolic aldehyde (28-oxo-beta-amyrin),
3-beta-20-dihydroxylupane
Masticadienonic aldehyde
3-oxo-malabarica-14(26), 17E,21-triene
Beta-amyrone
Beta-amyrin
Germanicol, The concentrations (in cottonseed oil) of each compound/fraction in the different compositions as used for the tMCAO model are presented in Table 2. Table 3 presents the number of animals per group and dosing.

TABLE 2

| Group (Entry nr. Table 1A) | Administered fraction/compound(s) | Concentrations (% w/w) |
|---|---|---|
| A (4) | Acidic Mixture 1 + NF-(1,2,3,4) | Acidic Mixture 1: 2.5% NF-(1,2,3): 0.5% each NF-4: 0.33% |
| B (27) | MDA + IMDA + NF-(1,2,3,4,P,A,B) + MLA + IMLA | MDA, IMDA: 1% each NF-(1,2,3): 0.5% each NF-(4,P): 0.33% each NF-(A,B): 0.25% each MLA, IMLA: 0.2% each |
| C (31) | MDA + IMDA + NF-(1,2,3,4) | MDA, IMDA: 1% each. NF-(1,2,3): 0.5% each NF-4: 0.33% |
| D (n.a.) | Placebo | Cottonseed oil (incl. BHT stabilizer) |
| E (2) | Acidic Mixture 1 + NF-(1,2,3,4,P,A,B) | Acidic Mixture 1: 2.5%; NF(1,2,3): 0.50% each. NF(4,P): 0.33% each. NF(A,B): 0.25% each |
| F (26) | MDA + IMDA + NF-(1,2,3,4,P,A,B) | MDA; IMDA 1% each NF-(1,2,3): 0.5% each NF-(4,P): 0.33% each NF-(A,B): 0.25% each |

TABLE 3

| Group (# in Table 1A) | number of rats (n) | Dose, (twice weekly) | Treatment duration (days) |
|---|---|---|---|
| A (4) | n = 13 | 50 μl/rat | 58 |
| B (27) | n = 12 | 50 μl/rat | 58 |
| C (31) | n = 10 | 50 μl/rat | 58 |
| D (n.a.) | n = 11 | 50 μl/rat | 58 |
| E (2) | n = 13 | 50 μl/rat | 58 |
| F (26) | n = 9 | 50 μl/rat | 58 |

The rats of the different groups were injected twice a week subcutaneous with 25 microliters of designated test item. First injection was given three hours after stroke induction. As used herein, the term 'Formulation X' refers to the formulation administered to the rats included in Group X, as described herein and in Table 2, wherein X is A, B, C, D, E or F.

Results and Conclusion

Rats included in groups A-F were treated with Compositions A, B, C, E and F, which include a combination of at least one triterpenoic acid and at least one neutral triterpenoid, or with placebo Composition D for 58 days via twice weekly subcutaneous injections starting immediately after reperfusion. During the study the neurological and somatosensory functions were monitored in a battery of behavioral tests.

Some spontaneous stroke recovery of neurological functions was observed during the 58 days follow-up after stroke induction. All tested compositions including combinations of at least one triterpenoic acid and at least one neutral triterpenoid, showed enhanced recovery of neurological function compared to the placebo group (Group D). When comparing the effect of compositions including combinations of terpenoid compounds, Compositions A and C displayed stronger effects comparing to compositions B, E and F (FIG. 1).

Sensory motor functions were also improved following the treatment with each one of the compositions comprising at least one triterpenoic acid and at least one neutral triterpenoid. Treatment with Composition A showed the largest difference compared to placebo (Group D) (FIG. 2). An enhanced improvement of sensory motor function compared to the placebo treated Group D was observed also for Compositions B, C, E and F, whereas the improvement was more pronounced for Compositions F and C. Unexpectedly, the observed therapeutic effects due to administration of the different compositions comprising at least one triterpenoic acid and at least one neutral triterpenoid, increased over time and were more pronounced towards day 58 after the operation.

General rats' health was identical in all groups, as all of them gained weight at the same rate with no significant differences between them.

In view of these findings it can be concluded that compositions of various combinations of molecules as disclosed in the current invention are effective for the treatment of stroke and have the potential to restore damaged motor function and to improve somatosensory deficits for subjects, who suffered a stroke.

Example 5—Glutamate-Induced Neurotoxicity Model

Ischemic or hemorrhagic stroke, traumatic brain injury (TBI) and other brain injuries are among the most devastating events patients may suffer. Despite having differing etiologies they appear to coalesce around the same complex pathophysiology including: immune suppression, free radical-mediated toxicity, brain/neuron damage, infection, cytokine-mediated cytotoxicity, inflammation and activation of glial cells. All of these result in cognitive and/or physical deficits.

Excito-neurotoxicity after different brain damages mainly results from excessive glutamate release with subsequent excessive influx of Ca2+, primarily mediated by N-methyl D-aspartate (NMDA) glutamate receptors. Glutamate release induces excitotoxicity and contributes to the pathophysiology of numerous neurological diseases including ischemia, inflammation, epilepsy, and neurodegenerative diseases.

Glutamate excitotoxicity is an important mechanism of neuronal death in a wide range of neurological disorders. A well-establish model was used to implement glutamate-induced excitotoxicity in primary cultures of cortical neurons in order to evaluate the potential neuroprotective effect of the compositions of the current invention.

Experimental Procedure
Compositions used:
Table 1A, Entry nr. 25, herein called "Combination A".
Table 1A, Entry nr. 31, herein called "Combination B:
Exerpt from Table 1A:

| Entry | A | B | C | D | E | F | G | H | I |
|-------|-----|------|------|------|------|------|------|------|------|
| 25 | MDA | IMDA | NF-1 | NF-2 | NF-3 | NF-4 | NF-A | NF-B | |
| 31 | MDA | IMDA | NF-1 | NF-2 | NF-3 | NF-4 | | | |

Cell Culture

Cortices were harvested from E19 Sprague-Dawley rat embryos. Tissues were enzymatically and mechanically dissociated to obtain a homogenous cell suspension, and cells were plated at 20000 per well of four 96 well plates in 200 µL neuronal medium.

Glutamate Induced Neurotoxicity:

Six (6) days after plating (DIV6) of primary cortical neurons in 200 µL of growth medium, test compounds were applied on neurons, by replacing half of the growth medium with 90 µL of medium containing a cytolysis probe which is a cell-impermeant and high affinity nuclei acid staining dye which is non-fluorescent in the absence of nuclei acids and exhibits a strong fluorescence upon binding to DNA. Then, 10 µL of 20× concentrated compounds in oil were added to the cells. The time lapse image acquisition was initiated 20 hours after the first treatment following a computer network problem that did not allow initiation of acquisitions from the time of the treatment. From that time to the end of the experiments, time lapse images (1 image every 4 hours) of the neuronal culture were taken in phase contrast and in fluorescence for cytolysis monitoring. This was performed in 4 different plates in parallel, each containing the test compounds and controls.

Nine (9) days after plating (DIV9), half of the growth medium was renewed with 90 µL of medium containing the cytolysis probe, and 10 µL of the same 20× concentrated compounds prepared at day 6 was added to the cells. At DIV10, half of the pretreated plates (2 plates) were treated with 100 µM glutamate/10 µM glycine to induce excitotoxicity, by addition of 10 µL of 21× concentrated glutamate solution. One glutamate treated plate and non-glutamate treated plate further received treatments with test compounds at DIV 11 and at DIV 14 following the same schedule (half medium renewal with addition of 10 µL concentrated compounds on cells). Cells were followed up to DIV 15, 24 hours after the last treatment. At the end of the experiments, all the cultures were permeabilized so the cytolysis probe labeled all the cells allowing total cell counting. Cytolysis over time was rationalized to total cell number to yield a percentage of cytolysed cells over time. All the experiments were performed in triplicate in the same experimental session.

Treatment Protocol:
Test compounds were tested with 2 treatment schedules:
 2 pre-treatments at −96 and −24 hours before glutamate treatments
 2 pre-treatments at −96 and −24 hours before glutamate treatments of other plates but no glutamate treatment.

Assay Endpoints/Analysis

Percentage of cytolyzed neurons over time (kinetics) from DIV 6 to DIV 15. As the monitoring period was very long, in some cases, the maximum cytolysis during this period exceeded the 100% that was measured at the end after cell permeabilization, because toxic treatments can induce dead cell detachments from the culture surface. In these cases, the maximum value that was reached during the monitoring (higher than the end 100% cytolysis value) was considered as 100%. In primary cultures, there is spontaneous neuronal loss over time. The first data point was considered at 0% cytolysis so only cell death appearing during the monitoring period was considered for homogeneity.

For specific glutamate effects assessments, some representations use the data point before glutamate application as the new 0% cytolysis to specifically assess glutamate effects without interference of former cytolysis events. Fixed time point graphs were also extracted from kinetic analyses, areas under curves (AUC) of the cytolysis kinetic curves were calculated from the 72 h time point to the end of the kinetics.

Figure 3A:
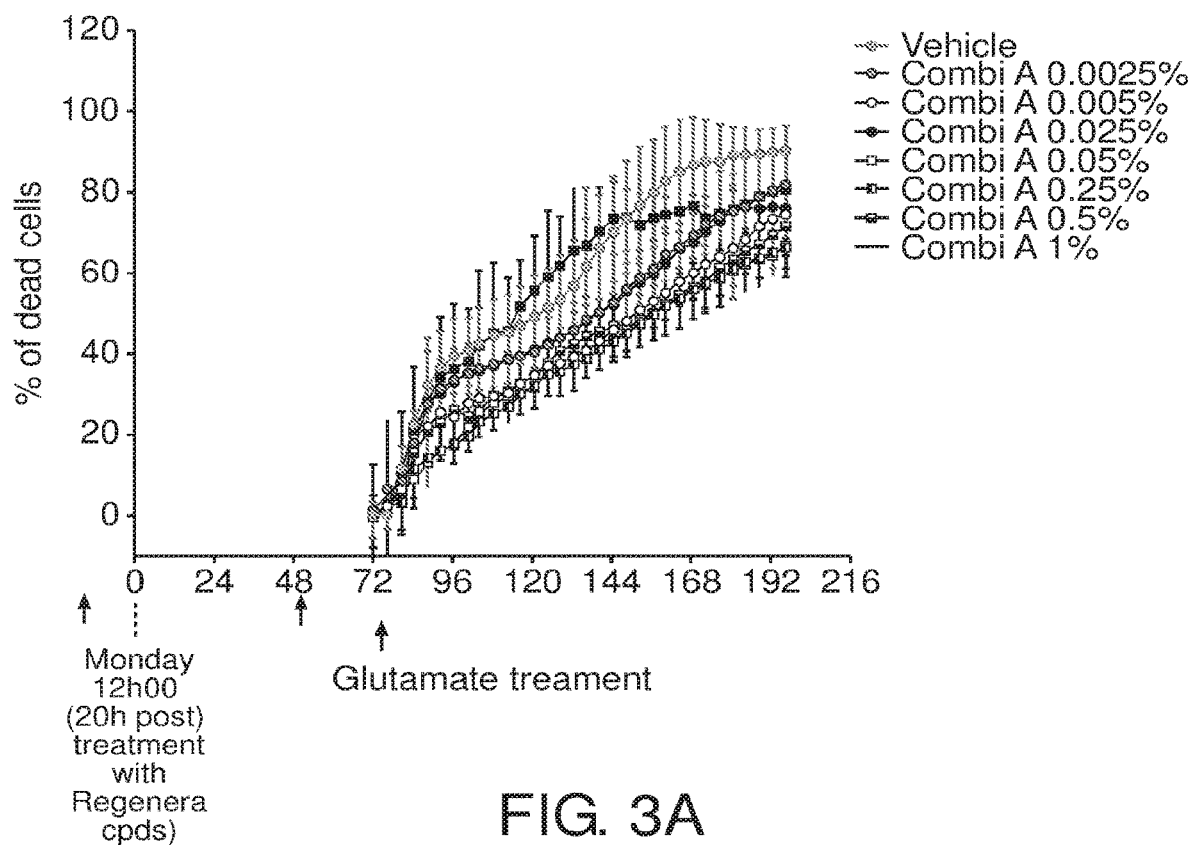
FIGS. 3A and 3B display graphs showing the effect of "Combination A" (Table 1A, Entry nr. 25) on cytolysis induced by glutamate treatment, normalized on the 72 hours data point.
Figure 3B:
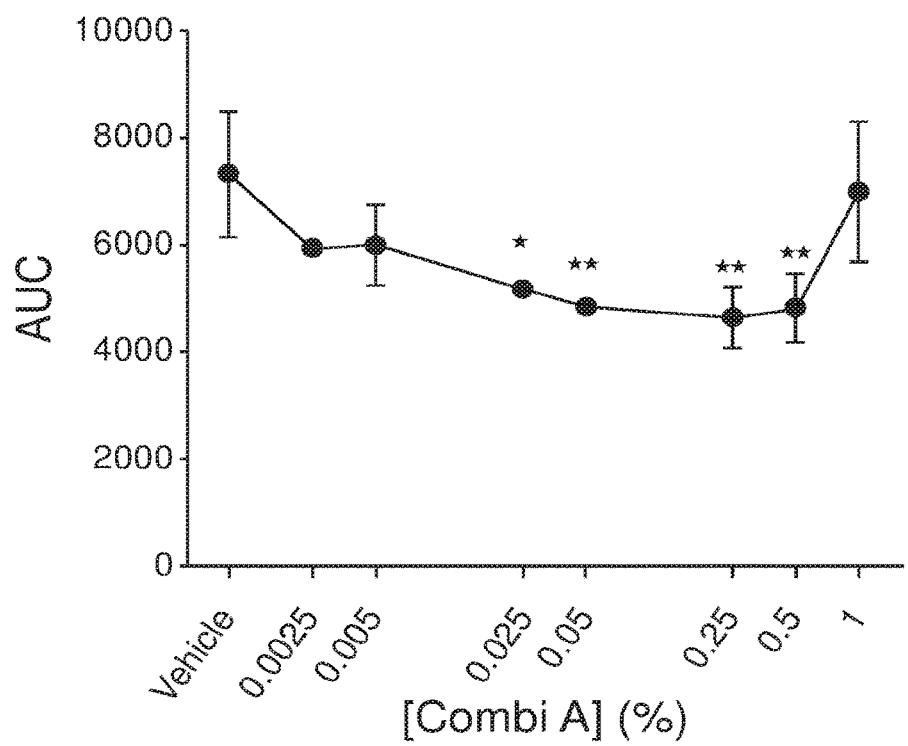

Results:
As shown in FIGS. 3A-3B, Combination A effectively decreased the excitotoxic effect of glutamate in a dose-dependent manner, from 0.025 to 0.5% (FIGS. 3A-B).

Figure 4A:
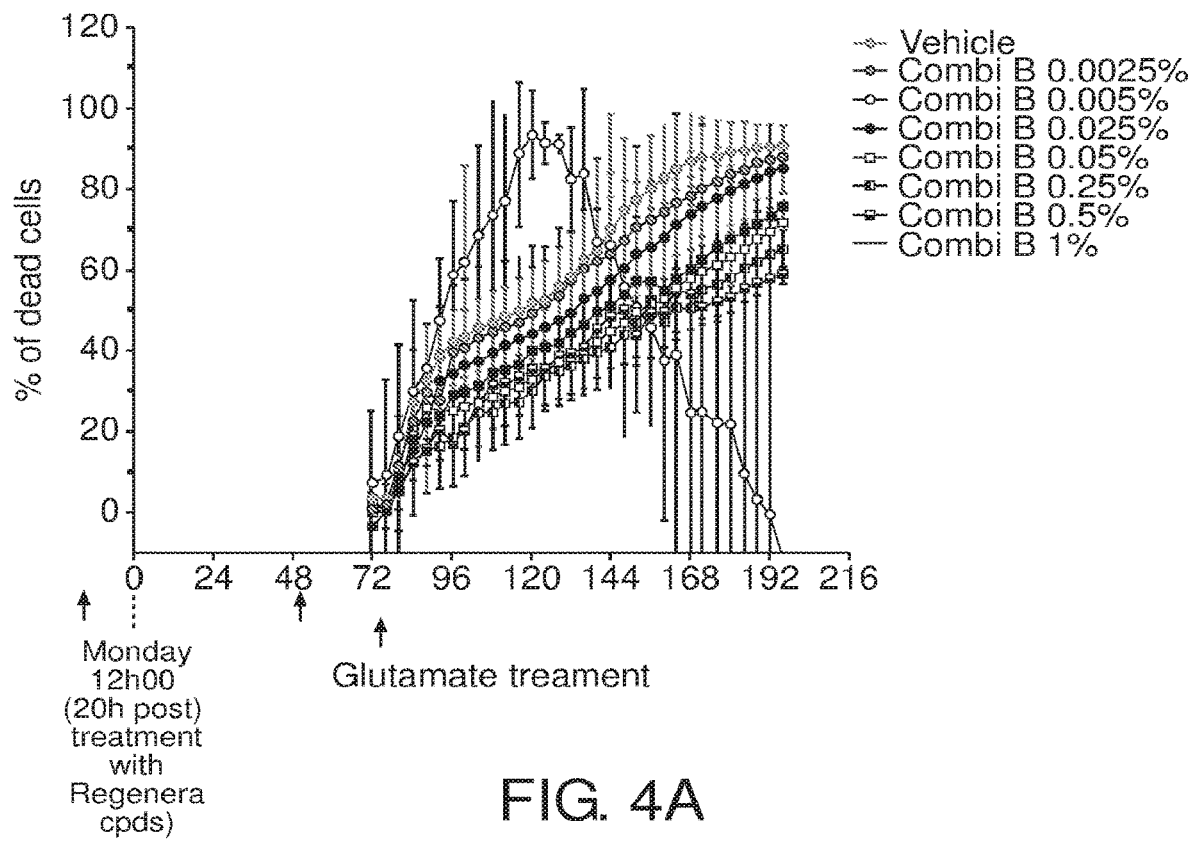
FIGS. 4A and 4B display graphs showing the effect of "Combination B" (Table 1A, Entry nr. 31) on cytolysis induced by glutamate treatment, normalization on the 72 hours data point.
Figure 4B:
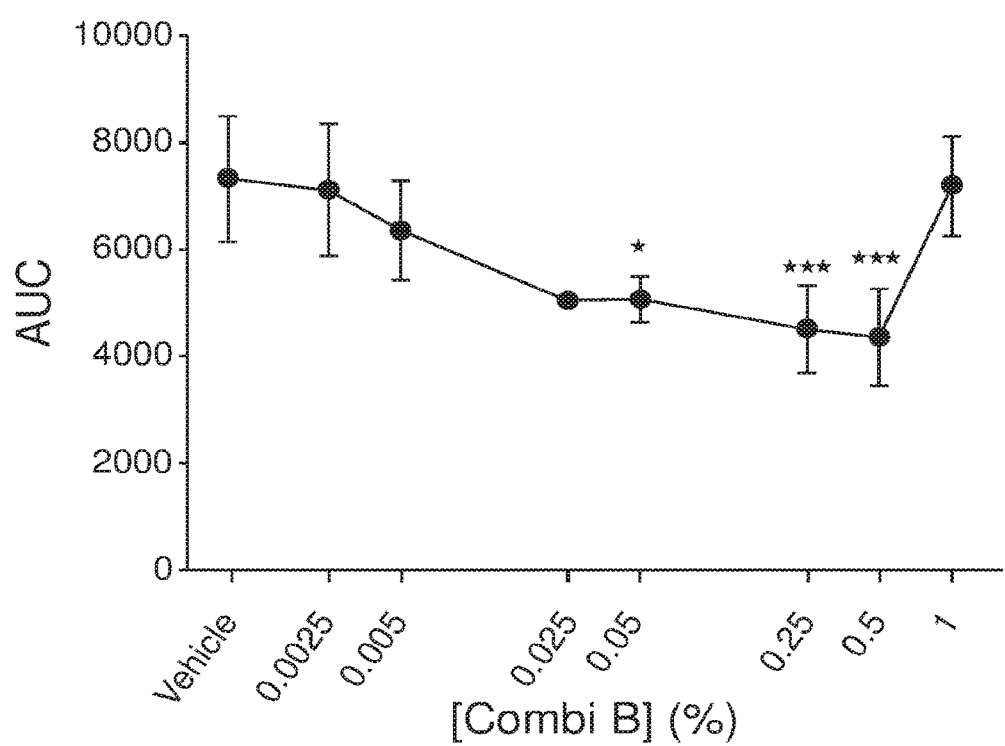

As shown in FIGS. 4A-B, Combination B also showed a dose-dependent decrease in glutamate excitotoxic effects from 0.05 to 0.5%.

Conclusions:
Excitotoxic insults elicited by 100 µM glutamate could be partially and significantly reversed by administration of Combination A or Combination B between concentrations of 0.025% (for combination A) and 0.05% (for combination B) to concentration 0.5% for both combinations.

Example 6—Tau-Hyperphosphorylation Assay—In-Vitro Model for Alzheimers Disease

Dementia is characterized by progressive deterioration of cognitive functioning, which means the loss of the ability to think, remember, or reason, as well as behavioral abilities. Various disorders and factors contribute to the development of dementia. Neurodegenerative disorders such as Alzheimer disease (AD), frontotemporal disorders, and Lewy body dementia result in a progressive and irreversible loss of neurons and brain functions. In some dementias, a protein called tau was shown to be hyper-phosphorylated and aggregates inside nerve cells in the brain, causing cell death. Disorders that are associated with an accumulation of tau are called tauopathies and Okadaic acid (OKA) is generally used to trigger tauopathies in animal models as it was shown to increase tau phosphorylation in cultured cells. Using OKA in combination with kinase inhibitors, is an established in vitro pharmacological model to identify compounds responsible for phosphorylating specific residues. In order to determine the therapeutic effect of the various combinations and formulations, in tau-related dementias, such Alzheimer disease, a model of Tau hyperphosphorylation induced by okadaic acid (OKA) on mature rat cortical neurons.

Experimental Procedure and Treatment Schedule
Compositions used:
Table 1A, Entry nr. 25, herein called "Combination A".
Table 1A, Entry nr. 31, herein called "Combination B:
Exerpt from Table 1A:

| Entry | A | B | C | D | E | F | G | H | I |
|---|---|---|---|---|---|---|---|---|---|
| 25 | MDA | IMDA | NF-1 | NF-2 | NF-3 | NF-4 | NF-A | NF-B | |
| 31 | MDA | IMDA | NF-1 | NF-2 | NF-3 | NF-4 | | | |

Cell Culture—
Cortices were harvested from E19 Sprague-Dawley rat embryos. Tissues were enzymatically and mechanically dissociated to obtain a homogenous cell suspension, and cells were plated in a 96 well plate.

Experimental Procedure—
After 9 days in vitro, for the 24-hour treatment wells, 10 µL of 20× concentrated compounds or vehicle were added to neurons. LiCl at 3 mM was added as a positive control. After 24 hours, 10 nM OA was added to the wells as a 11× concentrated solution (20 µL on 200 µL of medium). In the wells that were not pre-treated for 24 hours, test compounds or vehicle were added just before OKA addition (10 µL from the prepared 20× concentrated dose-responses). After 3 hours of OKA treatment in the cell incubator, half of the medium was discarded and 100 µL of 2% paraformaldehyde added to the wells for fixation. Cells were then processed for double immunofluorescent labeling of Neurons (MAP2 labeling) and Phospho-Tau (Phospho-PHF-tau pSer202+ Thr205 Antibody (AT8)). Nuclei were labeled using Hoechst 33342 10 µM in PBS.

Assay Endpoints/Analysis—
Percentage of neurons with high phospho-Tau intensity for each experimental condition. This percentage is calculated with a threshold above which significant Tau hyperphosphorylation is considered in neurons. This threshold is set up by comparing non-treated and okadaic acid treated conditions, between the negative and positive neuronal populations on a cell by cell scatterplot (cytometric analysis) in Fluofarma's CytoSurfer software.

Figure 5A:
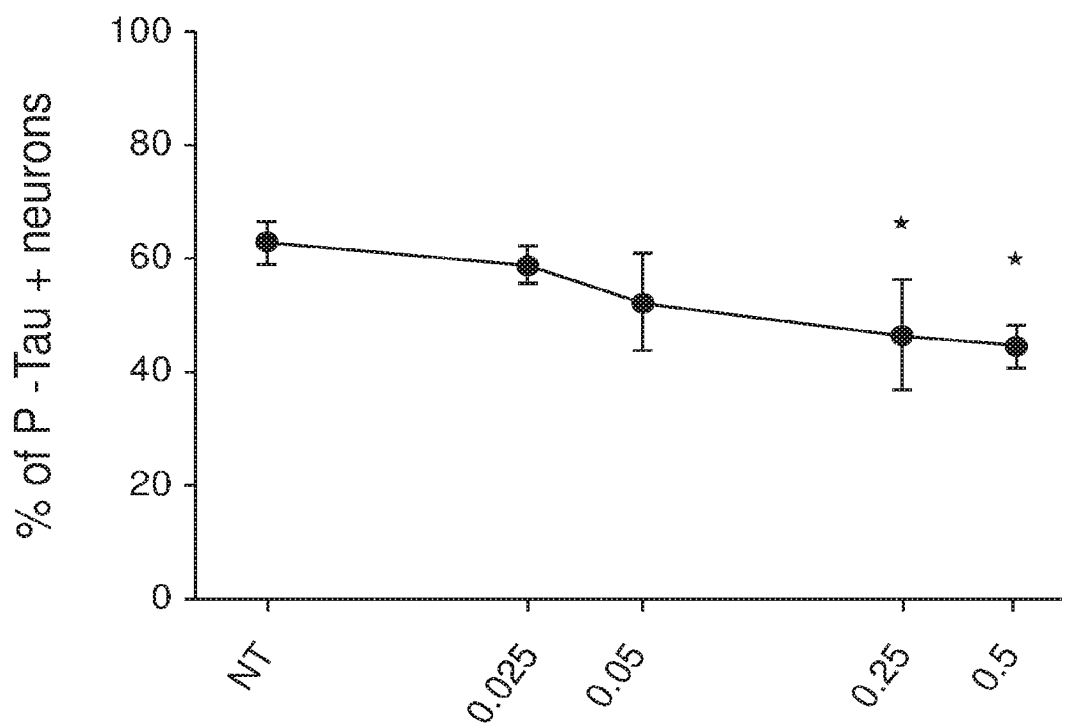
FIG. 5A shows line graph displaying the effect of "Combination A" (Table 1A, Entry nr. 25) on Okadaic acid (OKA) induced Tau hyperphosphorylation after a 24 hours pre-treatment. *: $p<0.05$ compared to the Non Treated condition (NT). One Way ANOVA followed by Dunnett's multiple comparison test.
Figure 5B:
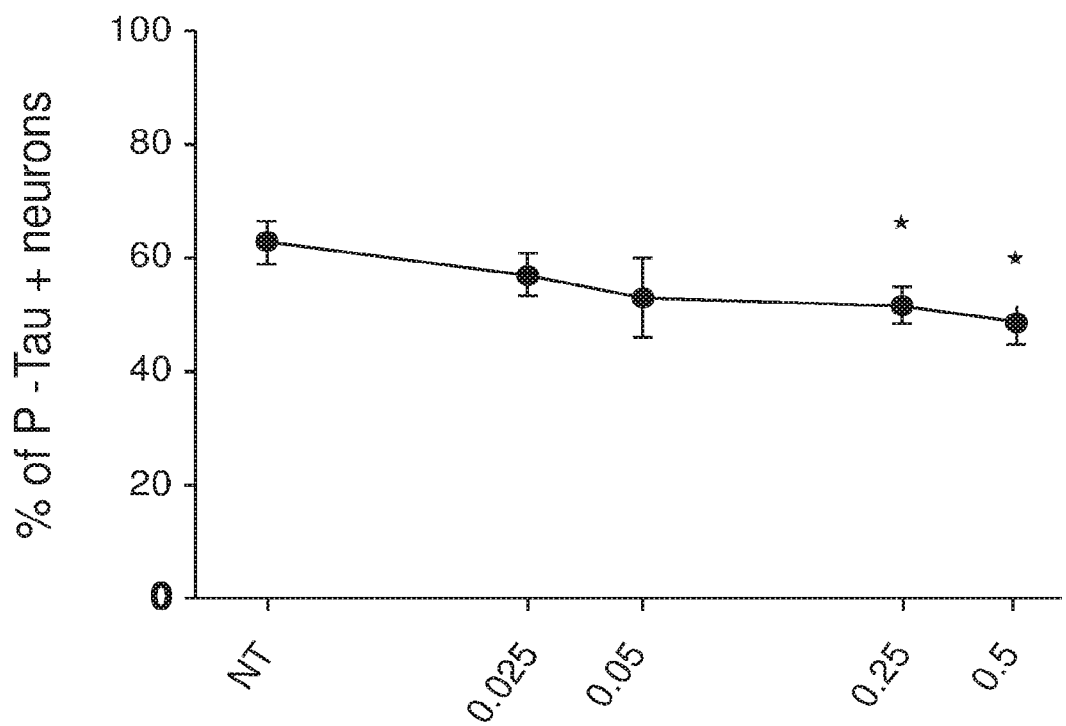
FIG. 5B shows line graph displaying the effect of "Combination B" (Table 1A, Entry nr. 31) on Okadaic acid (OKA) induced Tau hyperphosphorylation after a 24 hours pre-treatment or as a co-treatment. *: $p<0.05$ compared to the Non Treated condition (NT). One Way ANOVA followed by Dunnett's multiple comparison test.

Results: As demonstrated in FIG. 5A, the tested formulation (Combination A) is shown to dose dependently decrease Tau hyperphosphorylation with significant effects of the 0.25 and 0.5% concentrations applied as a 24 hour pre-treatment before Okadaic Acid treatment. As demonstrated in FIG. 5B, the tested formulation (Combination B) dose dependently decreased Tau hyperphosphorylation with significant effects of the 0.25 and 0.5% concentrations applied as a 24 hour pre-treatment before Okadaic Acid treatment.

Example 7—In-Vivo Models for Alzheimer's Disease

Dementia is characterized by progressive deterioration of cognitive functioning, which means the loss of the ability to think, remember, or reason, as well as behavioral abilities. Alzheimer's disease (AD) is the major cause of dementia whereas, vascular dementia, dementia with Lewy bodies, fronto-temporal dementia etc also lead to memory deficits. A reliable animal model of memory loss with certain characteristics have been established in multiple ways by exposing the animals to a predetermined brain injury or intracranial infusion of certain neurotoxins. An aged rat model for Alzheimer's with memory deficits demonstrate pathological features and complex behaviors common to AD, provides a natural model of aging and cognitive decline and is a useful choice for testing investigational therapies targeting mechanisms of neuroprotection, learning, and memory Many rodent behavioral tasks have been developed which are highly sensitive to the cognitive behavioral symptoms seen in AD, and these tests are extensively used as clinical diagnostic tools.

Among the numerous tasks designed for assessing distinct memory processes, the social recognition task in the rat offers the opportunity to evaluate a form of short-term working memory in the domain of social cognition, and its modification by pharmacological agents or physiopathological states, such as aging s. Social cognition in humans is obviously of great importance and its deficits, e.g., during aging and Alzheimer's dementia, often have dramatic consequences for the patient and their environment. Impairments in executive function are also a commonly observed cognitive impairments in neuropsychiatric disorders such as Schizophrenia, AD and Parkinson's disease. Cognitive decline and AD are closely related to aging within the human population. Aged rats and mice with memory deficits demonstrate pathological features and complex behaviors common to AD, providing an insightful alternative to traditional models. Aging is characterized by a progressive decline of cognitive performance, which has been partially attributed to structural and functional alterations of hippocampus. Cognitive decline and AD are closely related to aging within the human population. An aged rat model for AD with memory deficits demonstrate pathological features and complex behaviors common to AD, hence provides a natural model of aging and cognitive decline and are a useful choice for testing investigational therapies targeting mechanisms of neuroprotection, learning, and memory. In this study, the formulations were tested for potential cognition enhancing activity using the Social Recognition and Delayed Alternation Tests in the aged rat.

Experimental Procedure
Delayed Alternation Test in the Aged Rat (Acquisition)—
The experimental protocol is similar to that described in Porsolt et al (Drug Dev. Res., 35, 214-229, 1995).

Feeding Schedule—
5 days before starting the Delayed Alternation experiment, animals were submitted to restricted access to food (15 g per day) in order to habituate them to the food deprivation schedule used during the experiment. This food deprivation schedule continued throughout the experiment. Animals received the 15 g food ration in their home cages after the last animal is tested. Before the beginning of the lever-pressing, they were also given several 45 mg food pellets (those used in the Delayed Alternation) to habituate them to this novel food.

Delayed Alternation experiment—This experiment includes 2 consecutive phases:— Acquisition of lever-pressing (single lever); and Acquisition of delayed alternation (two levers).

Acquisition of Lever-Pressing—
The aim of this phase is to train animals to lever-press in order to receive a food pellet reward. The animals are submitted to about 10 lever-pressing acquisition sessions over 2 weeks (5 days per week) in the experimental chambers according to a fixed ratio (FR1) schedule of reinforcement. Reinforcement consists of a food pellet (45 mg)

delivered after each lever-press. Animals are first submitted to lever-pressing acquisition sessions where a response on either the right or the left lever resulted in the delivery of a food pellet. The levers are inserted in the chamber at the beginning of the session and are withdrawn at the end of the session. Afterwards, they are then subjected to several sessions in which the left or the right lever is pseudo-randomly presented every 5 seconds. A response on the lever results in the retraction of the lever and in the delivery of a food pellet. If the animals did not press the lever within 30 seconds, the lever was retracted without reinforcement and followed 5 seconds later by a new lever presentation. The house light comes on at the beginning of the session and is extinguished at the end of the session. Session terminate after 30 minutes or after the animal makes 50 lever responses. At the end of this phase between 80 and 100% of the animals acquire the lever-press response (i.e. they have made at least 20 responses during the final session). Animals which fail to learn are discarded from the experiment. If some animals are close to establishing steady lever-pressing behavior, they will be given extra training with the aim of having at least 12 animals per group.

Acquisition of Delayed Alternation (Drug Test)—

Subsequent to lever-pressing acquisition, animals were submitted to 10 delayed alternation sessions over 2 consecutive weeks (5 days per week). Each session consists of 36 trials separated by 10 seconds. Each trial consists of presenting the animal first with one lever (left or right). When the animal presses on the lever, the animal is given a food pellet, the lever is retracted and 2.5 seconds later both levers are presented. The animal has to learn to press on the lever opposite to that previously presented to gain a food reward (non-matching to sample). If the animal does not respond to a one- or two-lever presentation within 20 seconds, the lever(s) will be withdrawn without food reinforcement and the next trial starts 10 seconds later. The house light comes on at the beginning of the session and is extinguished at the end of the session. Sessions terminate after the animal has completed 36 trials, or after 30 minutes have elapsed.

Behavioral parameter analyzed was the choice reaction time. Choice reaction time is the reaction times to each two-lever presentation, expressed as the mean value per animal per session.

Statistical Analysis—

Data obtained during the delayed alternation acquisition will be analyzed by comparing aged control with young controls using unpaired Student's t tests at each session. Data obtained during the delayed alternation acquisition will be analyzed by comparing test substance-treated groups with aged controls using a two-way analysis of variance (with group and session as factor) with repeated measures at each session. The analysis will be followed by a one-way analysis of variance at each session in case of significant group or interaction effect and will be completed by Dunnett's t tests when group effect will be significant.

Social Recognition Test in the Aged Rat

The method, which detects facilitating effects of drugs on age-related memory deficits, follows that described by Lemaire et al (Psychopharmacology, 115, 435-440, 1994). The experiment was performed using unfamiliar open testing cage (46.5×26.5×18.5 cm) containing sawdust, one testing cage per experimental adult rat. Adult rat was allowed to habituate to the testing cage for at least 5 minutes. Then, an unfamiliar juvenile rat was placed in the testing cage with the adult rat for 5 min. Following this first contact (C1), the juvenile was removed and the adult rats was returned to its housing cage. 30 minutes after the adult was brought back to the same testing cage and the same juvenile (familiar) was then placed in the testing cage once again for a 5 minutes test session. The time the rat spends investigating (sniffing, grooming, licking, closely following) the juvenile at each contact was recorded. A recognition index (=C2/C1) was also calculated. Under such conditions, a mature adult rat normally recognizes the juvenile as familiar, as indicated by a reduction in the duration of social investigatory behavior at C2. Aged rats normally show amnesia in this task as indicated by the absence of a decrease in the duration of social investigatory behavior at C2. Data was analyzed by comparing the duration of social investigation at the second contact with the first contact for each group using paired Student's t tests. Data was analyzed by comparing aged controls with adult controls using unpaired Student's t tests. Data was analyzed by comparing test substances-treated groups with aged controls using one-way ANOVA followed by Dunnett's t tests in case of significant effects.

Drug Testing Procedure—

15 rats per group are included at the beginning of the experiments. Combination A, B and C were evaluated at 1 dose, administered s.c. twice weekly for 10 weeks before the delayed alternation experiment and then up to the end of the Social Recognition test (i.e. 13 weeks in total). During behavioural testing (social recognition, lever pressing stage and delayed alternation acquisition), administration is given after testing. The experiment includes an aged control and an adult/young control groups, receiving administrations of vehicle.

Results

Figure 6:
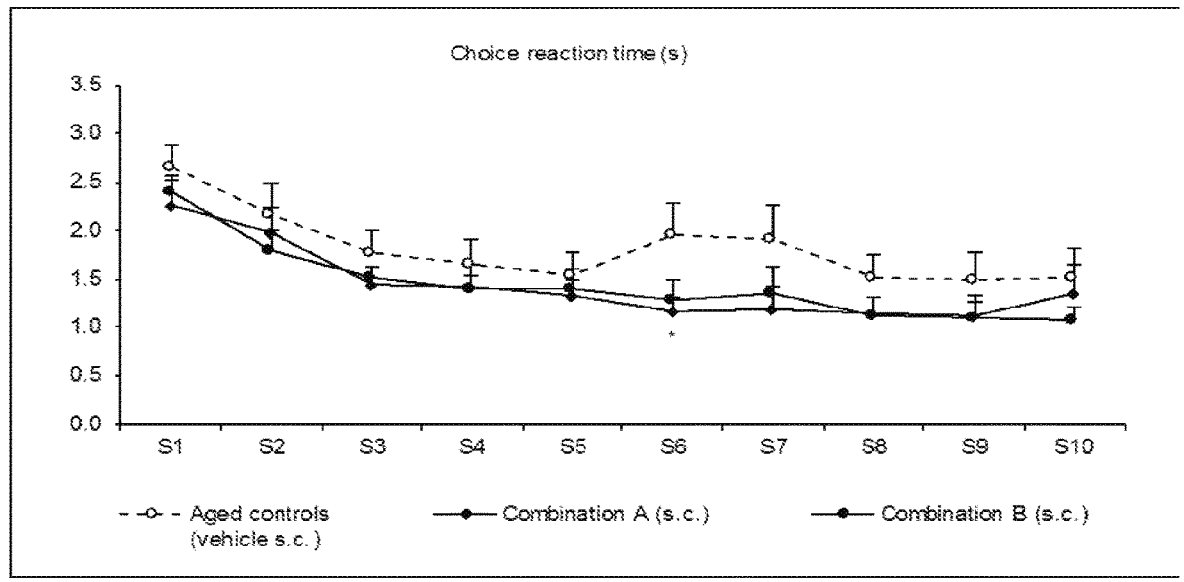
FIG. 6 displays the effect of "Combination A" (Table 1A, Entry nr. 25) and "Combination B" (Table 1A, Entry nr. 31) on choice reaction time. Reaction times to each two-lever presentation, expressed as the mean value per animal per session. Reaction times to each two-lever presentation, expressed as the mean value per animal per session. (*): compared with Aged controls (vehicle s.c.).

Delayed Alternation Test:

Combination A, administered s.c. twice weekly for 10 weeks, generally decreased choice reaction times significantly so at Session 6 (p<0.05), (FIG. 6). Combination B, administered s.c. twice weekly for 10 weeks, also showed a pronounced tendency to decreased choice reaction times, however without reaching statistical significance.

Social Recognition Experiment

Figure 7:
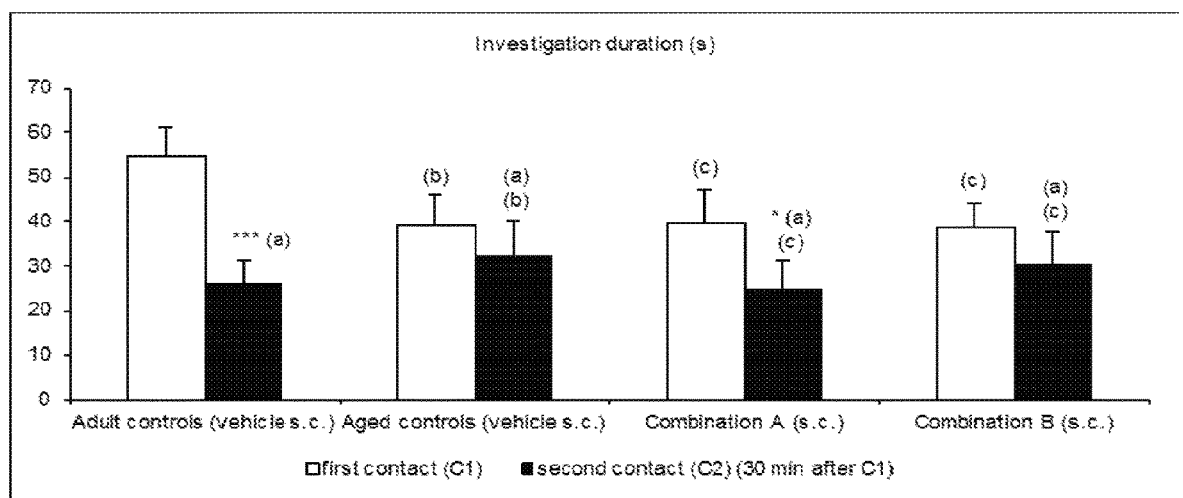
FIG. 7 displays the effect of "Combination A" (Table 1A, Entry nr. 25) and "Combination B" (Table 1A, Entry nr. 31) on the duration of social investigation at the second contact compared with the duration at the first contact for each group. The effect of combination A and B on the duration of social investigation at the second contact compared with the duration at the first contact for each group. (a): compared with first contact. (b): compared with Adult controls (vehicle s.c.). (c): compared with Aged controls (vehicle s.c.).
Figure 8:
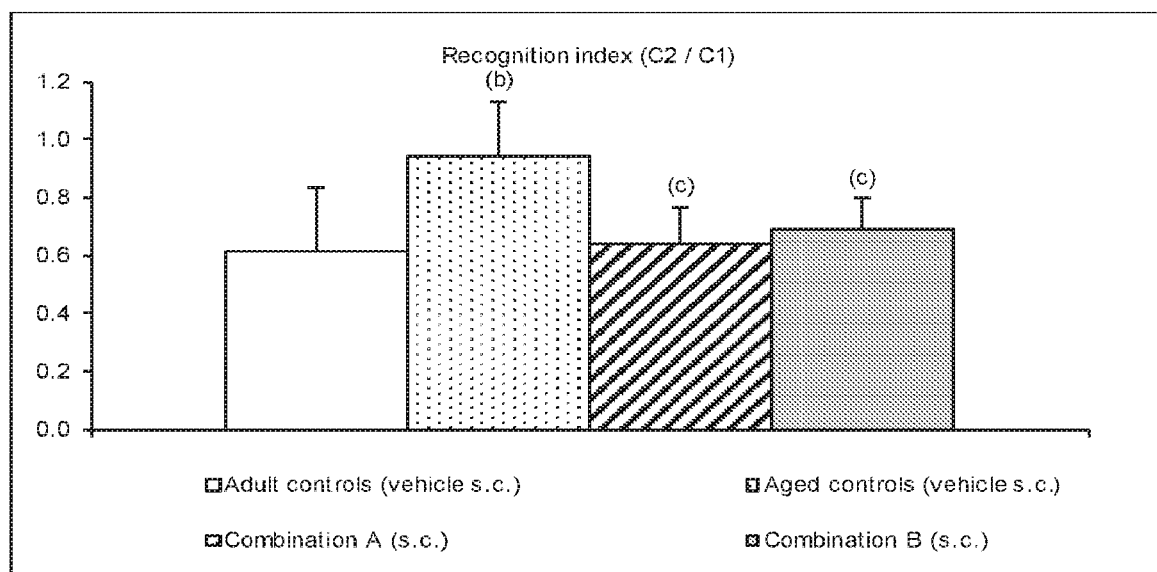
FIG. 8 displays the effect of "Combination A" (Table 1A, Entry nr. 25) and "Combination B" (Table 1A, Entry nr. 31) on the recognition index (=C2/C1). The effect of combination A and B on the recognition index (=C2/C1). (b): compared with Adult controls (vehicle s.c.). (c): compared with Aged controls (vehicle s.c.).

Combination A administered s.c. twice weekly over 12 weeks, significantly decreased the duration of investigation of the familiar juvenile at the second contact, as compared with the first contact (−39%, p<0.05). Combination B Showed a tendency to decrease the duration of investigation of the familiar juvenile at the second contact, as compared with the first contact (−21%, p=0.0675), (FIG. 7). Both combination A and B show a general trend to decrease the recognition index was not significantly modified as compared with aged controls (A: 0.64 versus 0.95, NS; B: 0.69 versus 0.95, NS), (FIG. 8).

Conclusions

The results show that repeated s.c. administration of Combinations A and B in aged rats have a beneficial effects on age-related processing speed deficits in the Delayed Alternation Test. In addition, the results suggest the presence of beneficial effects for Combination A, and Combination B administered s.c. twice weekly for 12 weeks on age-related deficits in the Social Recognition Test in the rat. Hence, taken together the results indicated the beneficial effects of the tested compositions in the Alzheimers model.

Example 8—Effect of Tested Formulations on 6-OHDA Induced Toxicity on Mesencephalic Primary Cultures and TH Positive Neurons Parkinson's disease (PD) is a debilitating neurodegenerative disorder characterized by the progressive loss of dopaminergic (DA) neurons in the substantia nigra pars compacta (SNc), leading to a marked dopamine (DA) depletion in striatum, the primary projection region, as well as extrastriatal nuclei of the basal ganglia. As tyrosine hydroxylase (TH) catalyses the formation of L-dihydroxyphenylalanine (L-DOPA), the rate-limiting step in the biosynthesis of DA, the disease can be considered as a TH-deficiency syndrome of the striatum. Problems related to PD usually build up when vesicular storage of DA is altered by the presence of either α-synuclein protofibrils or oxidative stress.

Neurotoxin induced-PD models are widely used to understand the mechanisms of neuronal degeneration in PD. 6-Hydroxydopamine (6-OHDA) is a selective catecholaminergic neurotoxin and is widely used both in vivo and in vitro studies to generate PD models.

The study was designed to examine the effects of the tested formulations in two different models. In the first part of the study, exposure of mesencephalic primary cultures with 6-OHDA was used as a model system to examine the cell viability and neuronal TH expression. In the second part of the study, a rat model of Parkinson Disease was induced by unilateral intra-striatum injection of the neurotoxin 6-OHDA. This injection produces DA neuron loss on the injected side while sparing the contralateral DA neurons. This model was used to evaluate the various formulations effect on motor function and TH expression in the rat brain.

Several behavioral tests have been developed or adapted from other neurological impairment models to elucidate the limb sensorimotor deficits associated with unilateral 6-OHDA-induced striatal dopamine depletion, and are correlated with the degree of dopaminergic degeneration. The affected limb functions can be compared with that of the intact limb, thereby increasing the sensitivity and repeatability of assessment across days.

Experimental Procedure:
Compositions used:
Table 1A, Entry nr. 25, herein called "Combination A".
Table 1A, Entry nr. 31, herein called "Combination B".
Table 1A, Entry nr. 34, herein called "Combination C".
Exerpt from Table 1A:

| Entry | A | B | C | D | E | F | G | H | I |
|---|---|---|---|---|---|---|---|---|---|
| 25 | MDA | IMDA | NF-1 | NF-2 | NF-3 | NF-4 | NF-A | NF-B | |
| 31 | MDA | IMDA | NF-1 | NF-2 | NF-3 | NF-4 | | | |
| 43 | MDA | IMDA | NF-1 | NF-2 | | | | | |

Cell Culture—
Primary culture of rat mesencephalic neurons from E14 rat embryos, treated with 6-hydroxy dopamine. Mesencephalons were harvested from E14 Sprague-Dawley rat embryos. Tissues were enzymatically and mechanically dissociated to obtain a homogenous cell suspension, and cells were plated at 100000 per well of a 96 well plate in 100 μL serum-containing neuronal medium.

6-OH DA Induced Neurotoxicity—
After mesencephalic neuron plating in 150 μL of medium, and after 3 hours, neurons were treated with test compounds by addition of 10 μL of 20× concentrated compounds in oil and with 10 μM 6-OH DA in growth medium (5× concentrated in 40 μL of growth medium). After 72 hours, the medium was removed and medium containing a fluorescent cytolysis marker was added to measure general cytolysis in the culture. Cells were then fixed and immunologically labelled with a Tyrosine Hydroxylase (TH) specific antibody for dopaminergic neuron counting and neurite length assessment of dopaminergic neurons. Images were acquired with a 10× objective, stitching 9 images per well, using a Pathway 855 platform and analyzed using the Neurite Outgrowth module of Metamorph software. All the experiments were performed in triplicate in the same experimental session.

Tested Formulations (Combinations)—
Test combinations dose responses were prepared in vehicle (Cottonseed oil) at 20 times (20×) the final tested concentrations by serial dilutions on the day of the first treatment. For treatments, 10 μL of each concentrated solution or vehicle was applied on 190 μL of neuronal growth medium. Test formulations were added just before 6-OH DA addition, from freshly prepared dose-responses in cottonseed oil.

Final Concentrations:
Combination A: 0.025%, 0.005%, 0.025%, 0.05%, 0.25%, 0.5%, 1%
Combination B: 0.025%, 0.005%, 0.025%, 0.05%, 0.25%, 0.5%, 1%
Combination C: 0.025%, 0.005%, 0.025%, 0.05%, 0.25%, 0.5%, 1%

Endpoints:
Number of cytolysed cells per well at endpoint and number of TH positive neurons. Results are shown as means+/− standard deviation (SD). Statistical analyses were performed using Student's t-tests for comparing two means or One Way ANOVA followed by Dunnett's multiple comparison test for comparing multiple means to the Vehicle treated group.

Figure 9A:
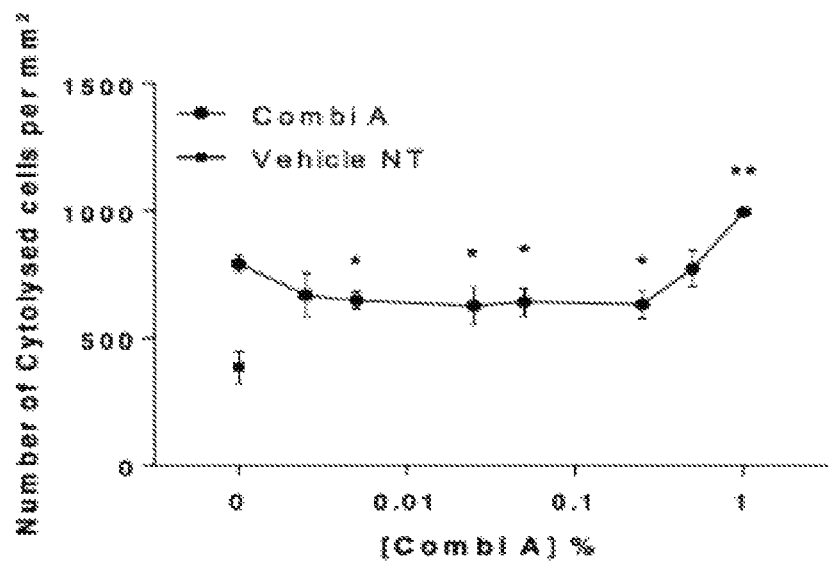
FIGS. 9A and 9B display effect of "Combination A" (Table 1A, Entry nr. 25) treatment on 6-OH DA induced toxicity on mesencephalic primary cultures and TH positive neurons.
Figure 9B:
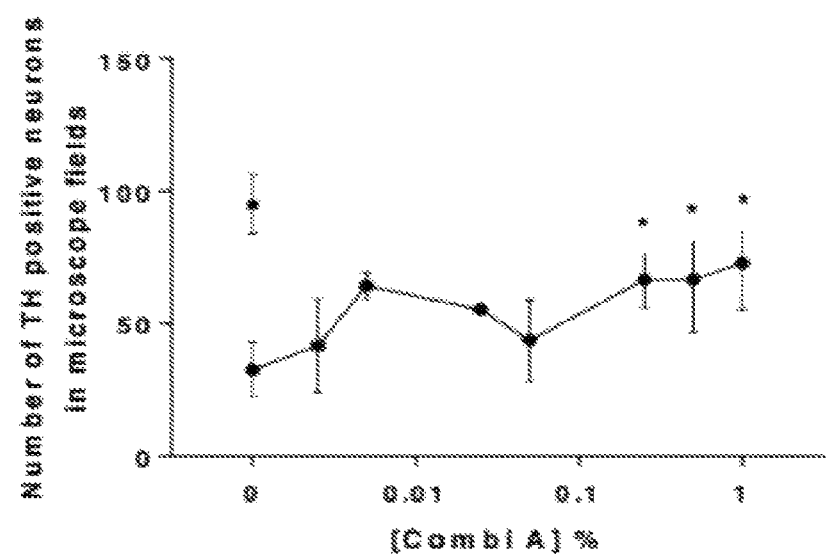

Results
Combination A—
As shown in FIG. 9A—Combination A at 0.005, 0.025, 0.05 and 0.25% significantly decreased the number of cytolyzed cells following 72 hours of 6-OH DA treatment.
As shown in FIG. 9B, The number of TH positive neurons was increased at 0.25, 0.5 and 1% compared to the 6-OH DA treated wells.

Figure 10A:
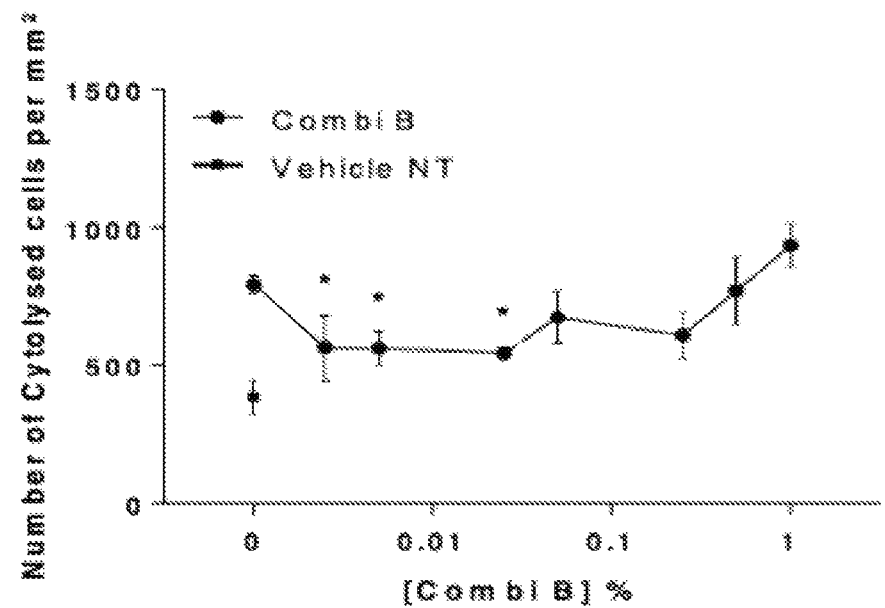
FIGS. 10A and 10B display the effect of "Combination B" (Table 1A, Entry nr. 31) treatment on 6-OH DA induced toxicity on mesencephalic primary cultures and TH positive neurons.
Figure 10B:
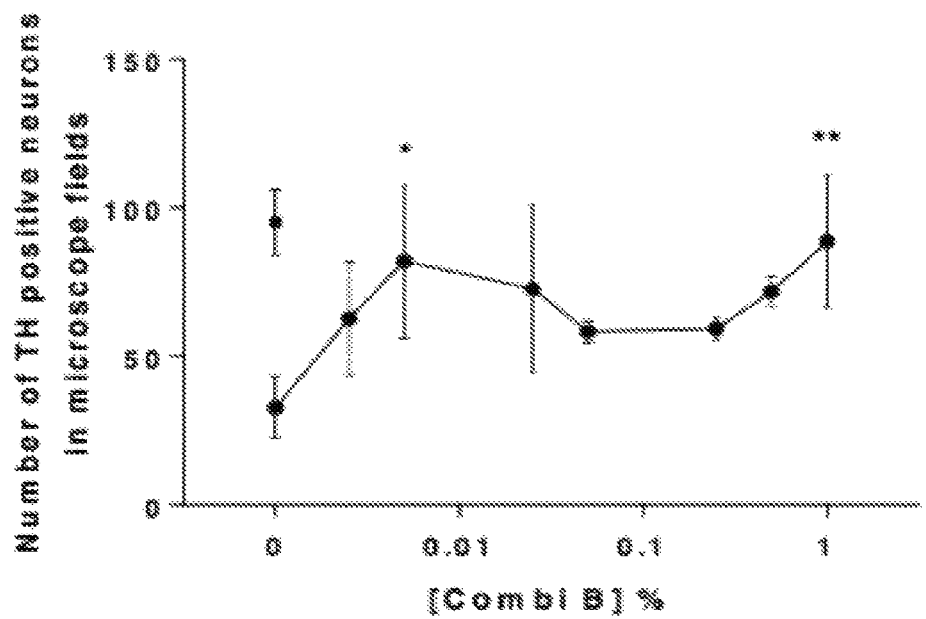

Combination B
As shown in FIG. 10A, Combination B at 0.0025, 0.005 and 0.025% significantly decreased the number of cytolyzed cells following 72 hours of 6-OH DA treatment.
As shown in FIG. 10B, the number of TH positive neurons was increased at 0.005 and 1% compared to the 6-OH DA treated wells.

Figure 11A:
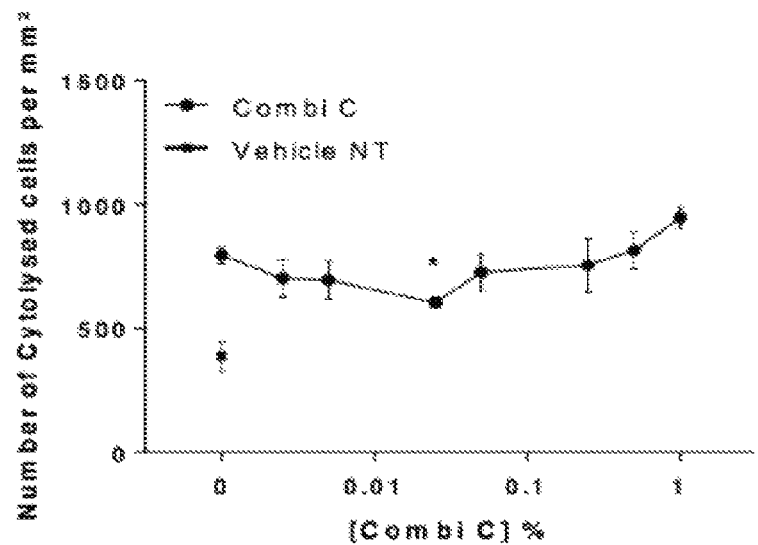
FIGS. 11A and 11B displays the effect of "Combination C" (Table 1A, Entry nr. 34) treatment on 6-OH DA induced toxicity on mesencephalic primary cultures and TH positive neurons.
Figure 11B:
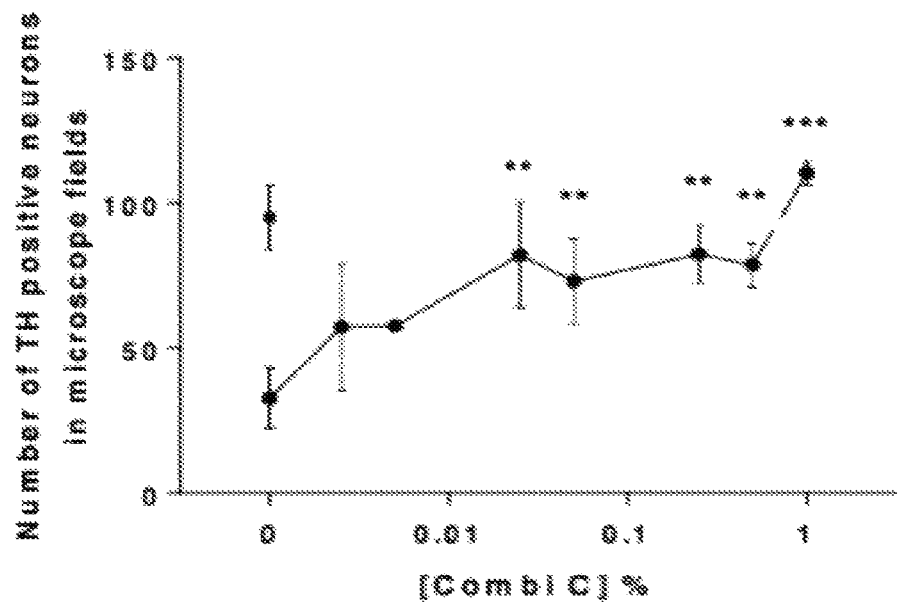

Combination C
As shown in FIG. 11A, Combination C at 0.025% significantly decreased the number of cytolyzed cells following 72 hours of 6-OH DA treatment.
As shown in FIG. 11B, The number of TH positive neurons was increased at 0.025, 0.05, 0.25, 0.5 and 1% compared to the 6-OH DA treated wells.

Conclusions
6-OHDA-induced neurodegeneration in vitro model was used to assess the potential protective effects of Combination A, Combination B and Combination C. Combination A, Combination B and combination C were shown to reduce cell death in mesencephalic neurons and increased the number of dopaminergic neurons after 72 hours of treatments, hence serve as protectants.

Example 9—Therapeutic Effect of Tested Combinations in the Rat 6-OHDA-Induced Parkinson Disease (PD) Model Rat model of Parkinson Disease was induced by unilateral intra-striatum injection of the neurotoxin 6-hydroxydopamine (6-OHDA). This injection produces dopaminergic (DA) neuron loss on the injected side while sparing the contralateral DA neurons.

Test Procedures:

Compositions used:

Table 1A, Entry nr. 25, herein called "Combination A".
Table 1A, Entry nr. 34, herein called "Combination C".
Exerpt from Table 1A:

| Entry | A | B | C | D | E | F | G | H | I |
|---|---|---|---|---|---|---|---|---|---|
| 25 | MDA | IMDA | NF-1 | NF-2 | NF-3 | NF-4 | NF-A | NF-B | |
| 34 | MDA | IMDA | NF-1 | NF-2 | | | | | |

Disease Induction:

Animals are anesthetized using ketamine (10%; 0.1 ml/kg body weight) and xylazine (2%; 0.01 ml/kg). The animals are then stereotactically injected into the right striatum with 2 μL of 6-OHDA at a concentration of 20 mg/ml in 0.02% ascorbic acid. Lesion coordinations are set according to bregma and dura in mm: L-3.5 mm; AP-1 mm; DV-5.5 mm. Following the injection (injection rate: 2 μl/5 min) the injecting needle is left for another 1 minute to avoid back flow and then slowly retracted.

Paw Placement Test (Cylinder Test)—

This test assesses a rat's independent forelimb use to support the body against the walls of a cylindrical enclosure. The test takes advantage of the animals' innate drive to explore a novel environment by standing on the hindlimbs and leaning towards the enclosing walls. To perform this test, rats are placed individually in a glass cylinder (21 cm diameter, 34 cm height) and wall exploration is recorded for 3 minutes. No habituation to the cylinder prior to recording is allowed. Wall exploration is expressed in terms of the ratio between the intact (R) and impaired legs (L) and calculated as the ratio of the intact leg (R)+½ of both forelimbs (½B) relative to the value of the intact leg (R)+the value of the impaired leg (L)+the value of both legs (B) was calculated. The paw placement test was conducted on Day −1 to obtain baseline data test was performed again 7 days after the injection of 6-OHDA, and animals with a ratio≥0.6 were included in the study. On study days 17, 24, 30, 43, 57 and 70 the animals were re-tested for their performance in the paw placement test.

Histological Analysis—Tyrosine Hydroxylase (TH)—

At the end of the study all animals are perfused with saline/heparin via the left heart ventricle, and then are perfused with 4% formalin. Organs are collected into vials containing 4% formalin for 24-48 hours. The tissues were then embedded in paraffin and 4 μm sections were cut from the Striatum region and Substantia Nigra (SNpc) region for IHC staining using anti-Tyrosine hydroxylase (TH) antibody and IHF staining using anti-alpha-Synuclein and anti-Glial fibrillary acidic protein (GFAP).

Figure 12A:
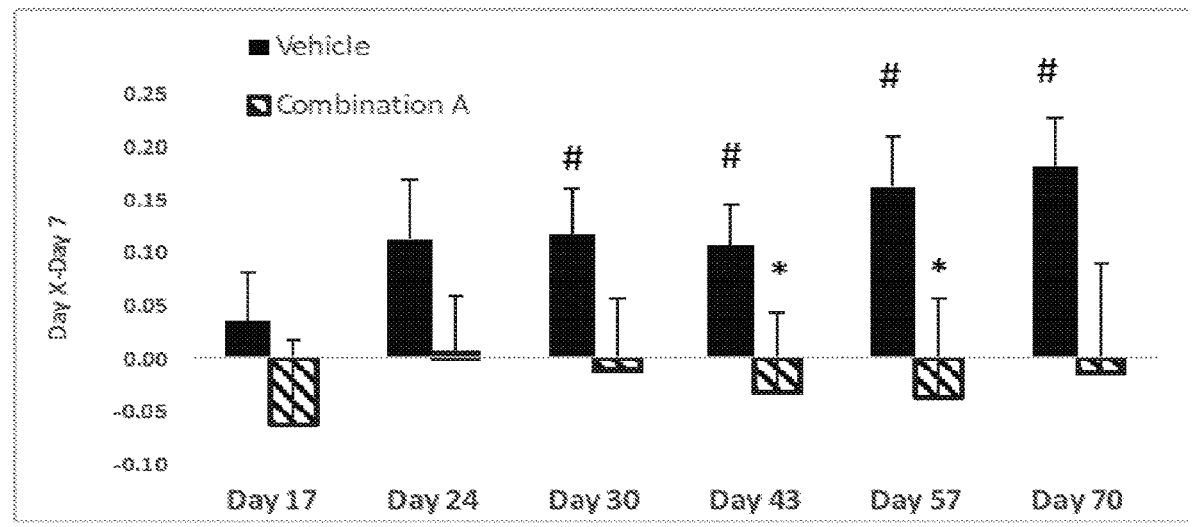
FIGS. 12A and 12B display the mean of "Combination A" (Table 1A, Entry nr. 25) and "Combination C" (Table 1A, Entry nr. 34) on Paw Placement differences (change from day 7).
Figure 12B:
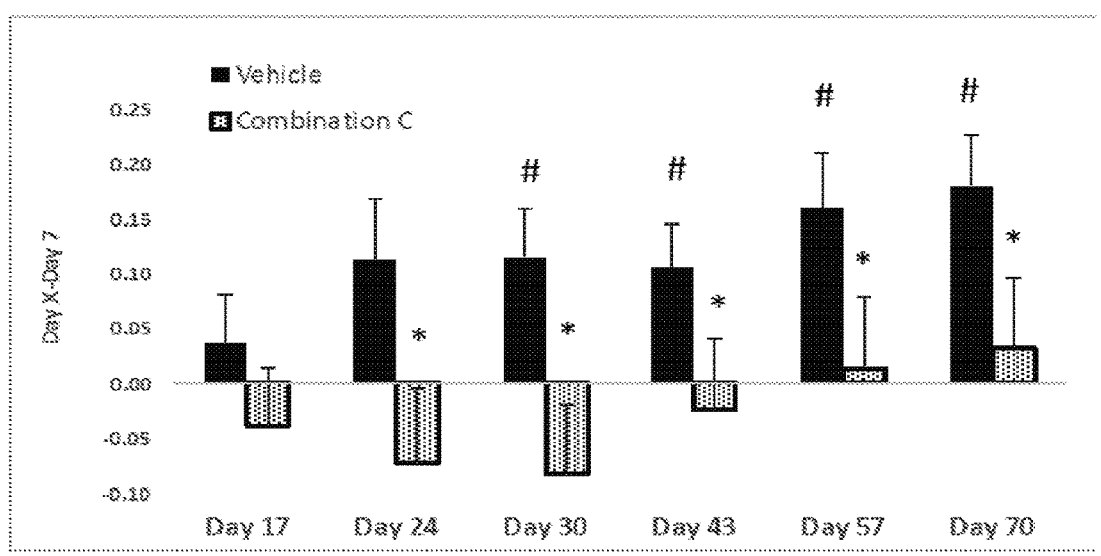

Results:

Paw placement test—In each examination day the average difference in ratio between that day to day 7 (day X-day 7) was calculated. Animals treated with a Vehicle showed an increase in the difference throughout the study. The increase in the difference ratio was found to be significantly higher from day 30 until the end of the study on day 70 and it is and indicator for time-dependent progression of the disease. Treatment with combination A and C generally showed a lower average of the differences from day 7 at all time points, as compared to the vehicle group. The difference reached statistically significance at day 43 and 57 for combination A. Differences for combination C were significantly lower from those of vehicle from day 24 to 70 (FIGS. 12A and 12B, respectively). This implies that combination A and C are able to significantly decrease disease progression.

Figure 13A:
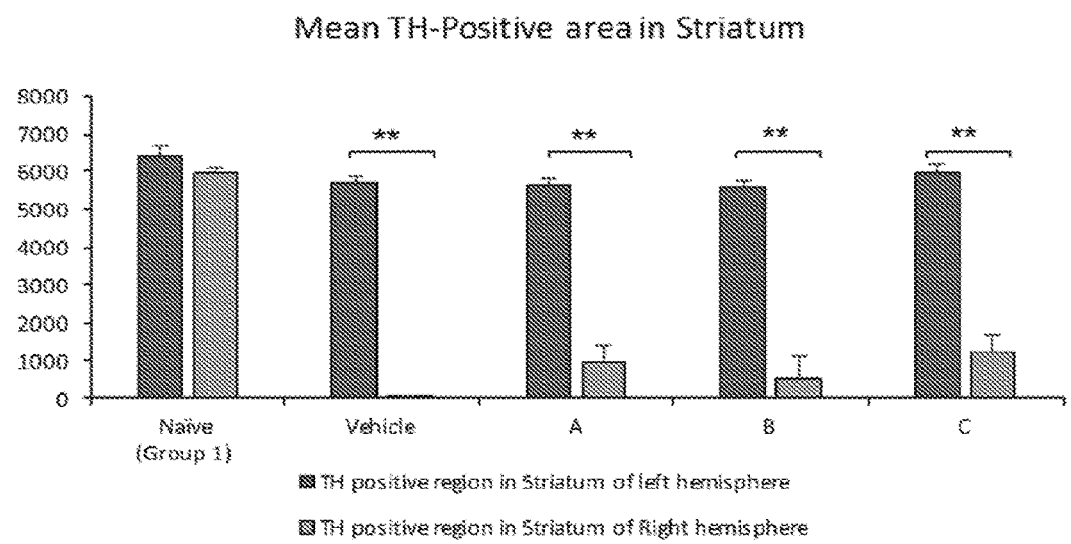
FIGS. 13A and 13B display respectively the mean TH-positive area in the striatum for "Combinations A, B and C" (Respective Entries 25, 31 and 34 in Table 1A); and the normalized mean TH-positive area in the striatum for "Combinations A, B and C" (Respective Entries 25, 31 and 34 in Table 1A).
Figure 13B:
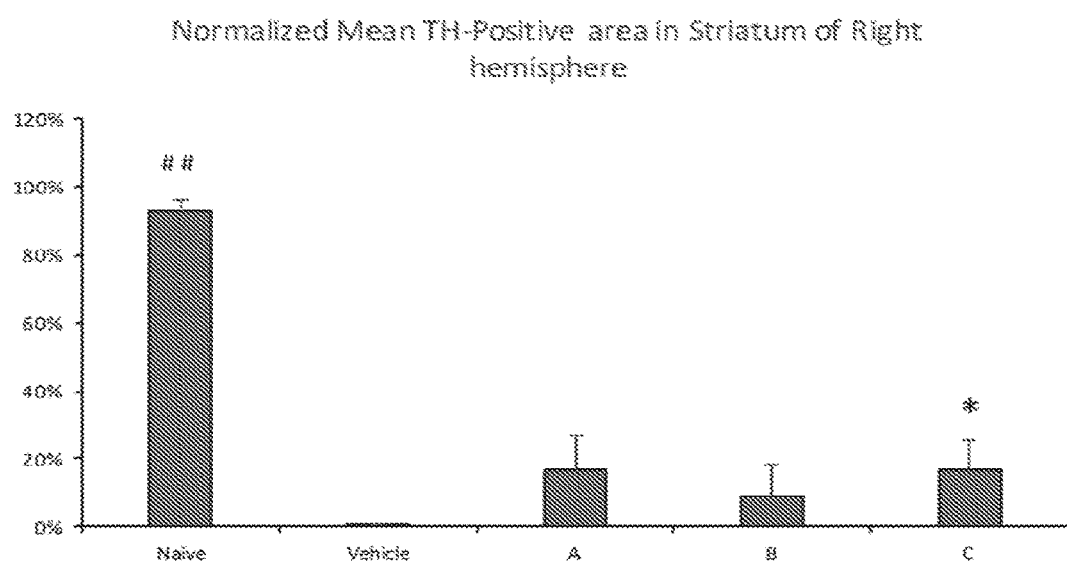

Histological Analysis—Tyrosine Hydroxylase (TH):

Analysis of TH positive cells in SNpc of animals treated with 6-OHDA showed statistically significant reduction in the number of TH-IR (immune-responsive) cells in the right hemisphere vs. the left hemisphere, indicating of the pronounced effect of the 6-OHDA in the. In addition, statistically significant reduction in TH-IR cells was found in the right hemisphere of the Vehicle group compared to the right hemisphere of the Naïve animals (FIG. 13A). Statistically significant increase was found in the number of TH positive cells in the right hemisphere of combination C-treated group compared to the vehicle group (17.05±8.16 vs. 0.48±0.48, $p<0.05$; T-TEST). A trend of increase in TH-IR cell number in SNpc of the right hemisphere was found in animals treated with Combination A in comparison to the Vehicle Group (17.1±9.1 vs. 0.48±0.48, for Group A vs. vehicle, respectively; $p=0.055$; T-test), (FIG. 13B).

Conclusions:

Treatment with combinations A and C starting 7 days after the administration of 6-OHDA, improved the mobility of the impaired forelimb, measured by using the paw placement test. Interestingly, the mean ratio of animals treated with combinations A and C was hardly changed throughout the study, relatively to day 7, in comparison to the gradual changes in the vehicle group, which indicates disease progression. Histological analysis of brains using anti-TH antibody showed the validity of the model as presented by reduction in the number of TH-IR cells in the SNpc of the 6-OHDA injected right hemisphere vs. the intact left hemisphere. Moreover, the TH-positively stained Striatum of the left hemisphere in comparison to the mostly unstained Striatum of the Right hemisphere, also highlights the extent of damage of 6-OHDA in the injection site. Combination C showed a statistically significant increase in the TH staining in the right hemisphere, compared to the vehicle group. Combination A showed a clear trend of activity in increasing the number of TH-IR cell in SNpc and the TH-positive area in the striatum of the 6-OHDA injected right hemisphere.

Example 10—Vascular Dimentia—Effect of Various Compostions in Reversing the Neurodegenerative Effects of Chronic Cerebral Hypoperfusion (Vascular Dementia) in a Rat Model Cerebral lesions can be experimentally induced in rat brains by permanent occlusion of both common carotid arteries which can affect cognitive function. This model is similar to vascular dementia and the experimental technique decrease the blood flow in the cerebral cortex and hippocampus by up to 40-80% for several months, inducing certain learning disorders. Thus this model is used to study the efficacy of the compositions of the current invention in reversing the deficiencies caused by vascular dementia lesions.

A total of 40 animals are randomized into 4 groups: an untreated sham control group, a vehicle control group and 2 groups with different compositions of the current invention (10-15 animals per group). They are randomized into 4 groups, an untreated sham control group, a vehicle control and 2 treated groups. Ten microliters of each composition (in cottonseed oil) or vehicle are administered subcutaneously twice weekly at equivalent intervals, with the first dose administered 14 days after induction of vascular dementia.

The Morris water maze (MWM) test is sensitive to hippocampal function. The water maze task is performed to evaluate two CCA-related learning deficits using the method described previously (Watanabe et al., Cilostazol Stroke. 2006; 37(6):1539-1545). In a 160-cm diameter circular pool filled with 20-cm deep water, a circular transparent acrylic platform is prepared, the top surface of which is 3 cm below the water. Rats are released facing the wall, and the time taken to escape to the platform is recorded as the escape latency. Tests are performed on day 3 before CCA occlusion and on days 14, 35, 56, 84 and 112 after CCA occlusion. On training days six training trials are conducted per day with an inter-trial interval of 2 min. Animals are placed in the pool at one of six starting positions. In each training trial, the time and path length required to escape onto the hidden platform are recorded. Results of six training trials are averaged to obtain a single representative value, and the averages are used for final statistical analyses. Animals that found the platform are allowed to remain on the platform for 30 sec. Animals that do not find the platform within 90 sec are softly guided to the platform for 30 sec at the end of the trial.

Performance of the various animal groups, treated with the compositions of the invention, vehicle treated animals and sham control animals are tested for frequency in platform location; the time spent in platform area; the latency to find the platform; the frequency in zone 1 location; the time spent in light part; the latency to find the platform; and the velocity Examples of Compositions Tested in the VD Model "Acidic Mixture 1" means the isolated acidic fraction of Mastic gum as prepared according to Example 1A. "Acidic Mixture 1" contains as main compounds the following:
  MA: Moronic acid (12-15%)
  OA: Oleanonic acid (18-20%)
  MDA: 24-Z-Masticadienonic acid (20-22%)
  IMDA: 24-Z-Isomasticadienonic acid (22-26%)
  3-beta-OAc-24-Z-masticadienolic acid (4-7%)
  3-beta-OAc-24-Z-isomasticadienolic acid (4-7%)

It further contains a number of other triterpenoic acids in small amounts, typically less than 5%. Possible triterpenoic acids that it may contain are:
  MLA: 3-beta-masticadienolic acid
  IMLA: 3-beta-isomasticadienolic acid
  Dihydromasticadienonic acid
  Dihydroisomasticadienonic acid "Acidic Mixture 2" contains the following compounds in % (w/w):
  MA: Moronic acid (15%)
  OA: Oleanonic acid (15%)
  MDA: 24-Z-Masticadienonic acid (25%)
  IMDA: 24-Z-Isomasticadienonic acid (30%)
  3-beta-OAc-24-Z-masticadienolic acid (8%)
  3-beta-OAc-24-Z-isomasticadienolic acid (7%)

In Table 4, "Acidic Mixture 1 (2.5%)" means a 2.5% (w/w) formulation of the acidic fraction as isolated in Example 1A in cottonseed oil. Likewise, "Acidic Mixture 2 (2.5%)" means a 2.5% (w/w) formulation of "Acidic Mixture 2" as defined above, "Neutral Mixture 1" is the neutral fraction as prepared according to Example 1A,B;

"Neutral Mixture 2" contains the following neutral triterpenoids:
NF-1: (8R)-3-beta, 8-dihydroxypolypoda-13E,17E,21-triene
NF-2: (8R)-3-Oxo-8-hydroxypolypoda-13E, 17E,21-triene
NF-3: Oleanonic aldehyde
NF-4: Tirucallol
NF-P: Dipterocarpol (20-hydroxydammar-24-en-3-one)
NF-A: (Betulon), 28-hydroxylup-20(29)-en-3-one
NF-B: Oleanonic alcohol; (28-hydroxy-beta-amyrone)
3-beta-hydroxy-13-alpha-malabarica-14(26), 17E,21-triene
20-hydroxy-lupan-3-one
28-Nor-17-hydroxylupen-3-one
28-oxo-lupen-3-one
28-nor-beta-amyrone
Isomasticadienonic aldehyde
Isomasticadienediol
Masticadienediol
Oleanolic aldehyde (28-oxo-beta-amyrin),
3-beta-20-dihydroxylupane
Masticadienonic aldehyde
3-oxo-malabarica-14(26), 17E,21-triene
Beta-amyrone
Beta-amyrin
Germanicol, The concentrations (in cottonseed oil) of each compound/fraction in the different compositions are presented in Table 4.

TABLE 4

| Group (nr. Entry in Table 1A) | Administered fraction/compound(s) | Concentrations (% w/w) |
|---|---|---|
| A (4) | Acidic Mixture 1 + NF-(1,2,3,4) | Acidic Mixture 1: 2.5% NF-(1,2,3): 0.5% each NF-4: 0.33% |
| B (27) | MDA + IMDA + NF-(1,2,3,4,P,A,B) + MLA + IMLA | MDA, IMDA: 1% each NF-(1,2,3): 0.5% each NF-(4,P): 0.33% each NF-(A,B): 0.25% each MLA, IMLA: 0.2% each |
| C (31) | MDA + IMDA + NF-(1,2,3,4) | MDA, IMDA: 1% each. NF-(1,2,3): 0.5% each NF-4: 0.33% |
| D (n.a.) | Placebo | Cottonseed oil (incl. BHT stabilizer) |
| E (2) | Acidic Mixture 1 + NF-(1,2,3,4,P,A,B) | Acidic Mixture 1: 2.5%; NF(1,2,3): 0.50% each. NF(4,P): 0.33% each. NF(A,B): 0.25% each |
| F (26) | MDA + IMDA + NF-(1,2,3,4,P,A,B) | MDA; IMDA 1% each NF-(1,2,3): 0.5% each NF-(4,P): 0.33% each NF-(A,B): 0.25% each |
| (25) | MDA + IMDA + NF-(1,2,3,4,A,B) | MDA; IMDA 1% each NF-(1,2,3): 0.5% each NF-4: 0.33%. NF-(A,B): 0.25% each |
| (43) | MDA + IMDA + NF-(1,2) | MDA; IMDA 1% each NF-(1,2): 0.5% each |

Example 11—Experimental Autoimmune Encephalomyelitis (EAE), a Model for Human Multiple Sclerosis (MS)

Experimental autoimmune encephalomyelitis (EAE) is a good model for human multiple sclerosis (MS) research. EAE IS induced by immunization of female Lewis rats with guinea pig MBP. This is an acute model of EAE. Lewis rats are immunized with myelin basic protein (MBP) in Freund's adjuvant by subcutaneous injection in the sub-planter region of hind paw. Clinical symptoms start developing around day 10 with loss of tail tone ("limp tail") and hind leg paralysis by day 14. The peak period is typically around day 14/15, after which time the animals start recovering.

Experimental Design:

Rats are treated with tested composition beginning on the day of immunization as "preventive treatment" to test the effect of test composition on the development of hind leg paralysis. Treatment may also be started at the onset of the first clinical sign of EAE to test the effect of test article on the recovery from paralysis.

Rats are dosed twice a week via SC route of administration. Eight rats are assigned to each of the groups (vehicle, treatment groups, as in Table 4, above) for a total of 48 animals. Animals are observed daily for body weight loss and clinical symptoms. Blood sample are taken for serum preparation and further investigation. The study takes approximately 21 days to complete.

Reagents:

*Mycobacterium tuberculosis* H37Ra (MT), Difco, Code 231141
Incomplete freund's adjuvant (IFA), Difco.
Lyophilized guinea pig spinal cord homogenate (MBP), Sigma (M2295)
Preparation of Encephalitogenic Emulsion
IFA is enriched with MT up to 4 mg/ml.
The MT powder will be crushed using pestle and mortar.
Lyophilized MBP will be weighed and suspended in PBS to yield 0.5 mg/mL
The 0.5 mg/ml homogenate of MBP will be mixed with equal amount of CFA (4 mg/mL MT)
Induction of EAE:

IFA is enriched with MT up to 4 mg/ml. The MT powder is crushed using pestle and mortar. Lyophilized MBP is weighed and suspended in PBS to yield 0.5 mg/mL. The 0.5 mg/ml homogenate of MBP is mixed with equal amount of CFA (4 mg/mL MT) and emulsified in two syringes connected with Leur lock.

Rats are anesthetized and emulsion is injected SC in the BT, each rat at a volume of 0.2 ml. Rats are scored for clinical signs of EAE and were weighed each other day up to 21 d post immunization (p.i.) The signs are scored as described below.

The emulsion is injected SC in the BT, each rat at a volume of 0.2 ml

Test Item ROA and doses:

Rats are treated with the indicated composition beginning on the day of immunization as "preventive treatment" to test the effect of tested composition on the development of hind leg paralysis.

Evaluation of the EAE Clinical Signs (Table 5):

TABLE 5

| Score | Clinical Signs | Description |
|---|---|---|
| 0 | Normal behavior | No clinical signs |
| 1 | Tail weakness | The tail is limp and droops. |
| 2 | Hind legs hypotonia and weakness. | Limb pareses, wobbly walk- when the rat walks the hind legs are unsteady or it drags one hind leg. |
| 3 | Hind legs paralysis, front legs normal | The rat can't move its hind legs and it drags them when it walks. Forelegs are normal. |
| 4 | Hind legs paralysis, front legs weak | The rat can't move its hind legs and it drags them when it walks. Forelegs are weak. |
| 5 | Full paralysis | The rat can't move at all. The rat is paralyzed. |
| 6 | Moribund/Death | |

Body Weights:

Body weights are recorded twice weekly throughout the entire study, on the days of dosing.

Clinical Signs:

Clinical Signs are Recorded Twice Weekly Throughout the Entire Study.

Blood Samples:

At the end of the study final bleeding is performed, blood samples are taken under full anesthesia from orbital sinus (as much as possible) and optionally, also from the heart. The blood is kept at room temperature for at least an hour for clotting. After, the blood is centrifuged at room temperature for 10 minutes at 1790 g (4000 RPM for centrifuge no. 060). The serum (supernatant) is separated from the blood cells using a suitable pipette and transferred to eppendorf marked according to the Study Protocol. Serum is stored in refrigerator (−70° C.) before sending to sponsor.

Tissue Collection:

After sacrificing, animals are dissected. Brain and sciatic nerve are collected from each animal and immediately placed into 4% PFA for further histopathological evaluation.

The invention claimed is:

1. A method of treating a condition selected from Multi System Atrophy (MSA), Progressive Supranuclear Palsy (PSP), Parkinson-plus syndrome, Parkinsonisms, tauopathic diseases and conditions and Pick's disease, comprising administering to a subject in need thereof a pharmaceutical composition comprising a combination of at least one triterpenoic acid and at least one neutral triterpenoid, and a pharmaceutically acceptable carrier, wherein the triterpenoic acid is selected from masticadienonic acid (MDA), isomasticadienonic acid (IMDA) or both, wherein the neutral triterpenoid is selected from (8R)-3-beta-8-dihydroxypolypoda-13 E,17E,21-triene (NF-1), (8R)-3-Oxo-8-hydroxypolypoda-13E,17E,21-triene (NF-2) or both.

2. The method of claim 1, wherein the pharmaceutical composition further comprises at least one additional triterpenoic acid selected from the group consisting of masticadienolic acid (MLA), isomasticadienolic acid (IMLA), 3-O-acetyl masticadienolic acid, 3-O-acetyl epimasticadienolic acid, 3-O-acetyl isomasticadienolic acid, 3-O-acetyl epi-isomasticadienolic acid, oleanonic acid (OA), moronic acid (MA) and combinations thereof.

3. The method of claim 1, wherein the pharmaceutical composition further comprises at least one additional neutral triterpenoid selected from the group consisting of oleanonic aldehyde (NF-3), tirucallol (NF-4), 28-hydroxylup-20(29)-en-3-one (NF-A), 28-hydroxy-beta-amyrone (NF-B).

4. The method of claim 3, wherein at least one of said neutral triterpenoids is selected from NF-3 and NF-4.

5. The method of claim 2, wherein the pharmaceutical composition comprises at least two additional triterpenoic acids.

6. The method of claim 3, wherein the pharmaceutical composition comprises at least two additional neutral triterpenoids.

7. The method of claim 1, wherein the pharmaceutical composition is substantially devoid of essential oils.

8. The method of claim 1, wherein at least one triterpenoic acid is obtained from a plant source.

9. The method of claim 1, wherein at least one triterpenoic acid is obtained via chemical synthesis.

10. The method of claim 1, wherein at least one neutral triterpenoid is obtained via chemical synthesis.

11. The method of claim 1, wherein at least one neutral triterpenoid is obtained from a plant source.

12. The method of claim 8, wherein said plant source comprises mastic gum.

13. The method of claim 1, wherein said pharmaceutically acceptable carrier comprises at least one oil.

14. The method of claim 1, wherein the pharmaceutical composition is in a form suitable for administration by a route selected from the group consisting of parenteral, transdermal, oral and topical.

15. The method according to claim 3, wherein the pharmaceutical composition comprises pharmaceutically active ingredients consisting essentially of: MA, OA, MDA, IMDA, 3-O-acetyl masticadienolic acid, 3-O-acetyl isomasticadienolic acid, NF-1, NF-2, NF-3, NF-4, NF-A and NF-B; and the pharmaceutically acceptable carrier.

16. The method according to claim 3, wherein the pharmaceutical composition comprises pharmaceutically active ingredients consisting essentially of: MA, OA, MDA, IMDA, 3-O-acetyl masticadienolic acid, 3-O-acetyl isomasticadienolic acid, NF-1, NF-2, NF-3 and NF-4; and the pharmaceutically acceptable carrier.

17. The method according to claim 3, wherein the pharmaceutical composition comprises pharmaceutically active ingredients consisting essentially of: OA, MDA, IMDA, 3-O-acetyl masticadienolic acid, 3-O-acetyl isomasticadienolic acid, NF-1, NF-2, NF-3, NF-4, NF-A and NF-B; and the pharmaceutically acceptable carrier.

18. The method according to claim 3, wherein the pharmaceutical composition comprises pharmaceutically active ingredients consisting essentially of: OA, MDA, IMDA, 3-O-acetyl masticadienolic acid, 3-O-acetyl isomasticadienolic acid, NF-1, NF-2, NF-3 and NF-4; and the pharmaceutically acceptable carrier.

19. The method according to claim 4, wherein the pharmaceutical composition comprises pharmaceutically active ingredients consisting essentially of: MDA, IMDA, MLA, IMLA, NF-1, NF-2, NF-3, NF-4, NF-P, NF-A and NF-B; and the pharmaceutically acceptable carrier.

20. The method according to claim 3, wherein the pharmaceutical composition comprises pharmaceutically active ingredients consisting essentially of: MDA, IMDA, NF-1, NF-2, NF-3 and NF-4; and the pharmaceutically acceptable carrier.

21. The method according to claim 1, comprising pharmaceutically active ingredients consisting essentially of: of MDA, IMDA, NF-1, NF-2; and the pharmaceutically acceptable carrier.

* * * * *